(12) United States Patent
Janson et al.

(10) Patent No.: US 7,253,260 B2
(45) Date of Patent: Aug. 7, 2007

(54) HUMAN IL-18 CRYSTAL STRUCTURE

(75) Inventors: Cheryl A. Janson, King of Prussia, PA (US); Nestor O. Concha, King of Prussia, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 565 days.

(21) Appl. No.: 10/414,774

(22) Filed: Apr. 16, 2003

(65) Prior Publication Data

US 2003/0232032 A1 Dec. 18, 2003

Related U.S. Application Data

(60) Provisional application No. 60/373,293, filed on Apr. 17, 2002.

(51) Int. Cl.
*C07K 14/00* (2006.01)
*G01N 33/53* (2006.01)
*G06F 19/00* (2006.01)

(52) U.S. Cl. .................. 530/351; 435/7.1; 702/19; 702/27

(58) Field of Classification Search .................. 514/12; 530/350
See application file for complete search history.

(56) References Cited

U.S. PATENT DOCUMENTS

| | | | |
|---|---|---|---|
| 5,192,324 A | 3/1993 | Kenna | 623/16 |
| 5,914,253 A | 6/1999 | Okamura et al. | 435/69.52 |
| 6,207,641 B1 | 3/2001 | Torigoe et al. | 514/12 |
| 6,214,584 B1 | 4/2001 | Ushio et al. | 435/69.52 |
| 6,268,486 B1 | 7/2001 | Kumikata et al. | 530/412 |
| 6,274,709 B1 | 8/2001 | Okamura et al. | 530/351 |
| 6,277,598 B1 | 8/2001 | Okamura et al. | 435/69.52 |
| 2003/0099607 A1 | 5/2003 | Okmura et al. | 424/85.1 |

FOREIGN PATENT DOCUMENTS

| | | |
|---|---|---|
| WO | WO92/13885 | 8/1992 |
| WO | WO01/58956 | 8/2001 |
| WO | WO03/057821 | 7/2003 |

OTHER PUBLICATIONS

Giege et al. Crystallogenesis of Biological Macromolecules: Facts and Perspectives. Acta Cryst., (1994) D50. pp. 339-350.*
Pechkova et al. Protein nanocrystallography: a new approach to structural proteomics. Trends in Biotechnology. 2003. vol. 22, No. 3, pp. 117-122.*
Drenth, J. "Principles of Protein X-Ray Crystallography", 2nd Edition, 1999 Springer-Verlag New York Inc., Chapter 1, pp. 1-19.*
Weber, P.C. Overview of Crystallization Methods. Methods in Enzymology, 1997, vol. 276, pp. 13-22.*
Ushio, et al., "Cloning of the cDNA for Human IFN-γ-Inducing Factor, Expression in *Escherichia coli*, and Studies on the Biologic Activities of the Protein," *The Journal of Immunology*, 156: 4274-4279 (1996).
Okamura, et al., "Cloning of a new cytokine that induces IFN-γ production by T Cells," *Nature*, 378: 88-91 (1995).
Mühlhahn, et al, "Structure of Interleukin 16 Resembles a PDZ Domain with an Occluded Peptide Binding Site," *Nature Structural Biology*, vol. 5, No. 8, pp. 682-686 (1998).

* cited by examiner

*Primary Examiner*—David J. Steadman
*Assistant Examiner*—Suzanne M. Noakes
(74) *Attorney, Agent, or Firm*—Elizabeth J. Hecht; Edward R. Gimmi; Charles M. Kinzig

(57) ABSTRACT

A novel human IL-18 native crystalline structure is identified.

4 Claims, 4 Drawing Sheets
(4 of 4 Drawing Sheet(s) Filed in Color)

HUMAN IL-18 CRYSTAL STRUCTURE

CROSS-REFERENCE TO RELATED APPLICATION

This application claims priority to the earlier provisional U.S. application Ser. No. 60/373,293, which was filed on Apr. 17, 2002, the contents of which are herein incorporated by reference in their entirety.

TECHNICAL FIELD OF THE INVENTION

The invention relates to the identification of a novel crystalline structure of the human IL-18 (hIL-18) cytokine, its mode of binding to its receptor, and methods enabling further design and selection of molecules with hIL-18-like activity.

BACKGROUND OF THE INVENTION

IL-18 is a type of cytokine or substance that mediates signal transduction in the immune system. As seen in Japanese Patent Kokai Nos.27,189/96 and 193,098/96 and Okamura et al., *Nature, Vol.* 378, No. 6,552, pp. 88-91 (1995), IL-18 was provisionally designated as "interferon-gamma inducing factor" immediately after its discovery. This designation was later changed into "IL-18" in accordance with the proposal in Ushio, et al., *Journal of Immunology*, Vol. 156, pp. 4,274-4,279 (1996). IL-18 in its mature form consists of 157 amino acids. It induces immunocompetent cells in the production of interferon-gamma (hereinafter abbreviated as "IFN-gamma."), which is a useful biologically-active protein capable of inducing and enhancing the generation and cytotoxicity of killer cells. Extensive research is currently underway to develop and explore the various utility of IL-18 in pharmaceuticals. These greatly expected applications include using IL-18 as antiviral, antimicrobial, antitumor and anti-immunopathic agents.

In nature, cytokines, including IL-18, are produced and secreted as substances responsible for signal transduction in the immune system. Therefore, when cytokines are administered to the body of mammals, they disturb the naturally existing equilibrium in the mammal's immune system. The surfaces of mammalian cells bear sites or "receptors" that are responsible for recognition of cytokines and secreted cytokines transduce no signal in cells until they are bound to the receptors. In a normal immune system, a definite equilibrium exists between respective cytokines and their receptors. There are currently unmet needs in finding and learning the biological and structural properties of IL-18 and its receptors and using such knowledge in designing drugs for treatment and ameliorating diseases and disorders such as viral and microbial infections, cancer, inflammation, etc.

SUMMARY OF THE INVENTION

In one aspect, the present invention relates to a human IL-18 protein molecule having the coordinates of Table I in an essentially pure native form or a homolog thereof.

In another aspect, the present invention provides a novel crystalline form of the human IL-18 molecule.

In yet another aspect, the present invention provides direct information on the specific role played by the residues responsible for the binding of human IL-18 to its receptor.

In a further aspect, the present invention includes machine-readable media encoded with data representing the coordinates of the three-dimensional structure of the IL-18 crystal.

BRIEF DESCRIPTION OF THE FIGURES

The patent or application file contains at least one drawing executed in color. Copies of this patent or patent application with color drawings will be provided by the Office upon request and payment of the necessary fee.

DETAILED DESCRIPTION OF THE INVENTION

Figure 1:
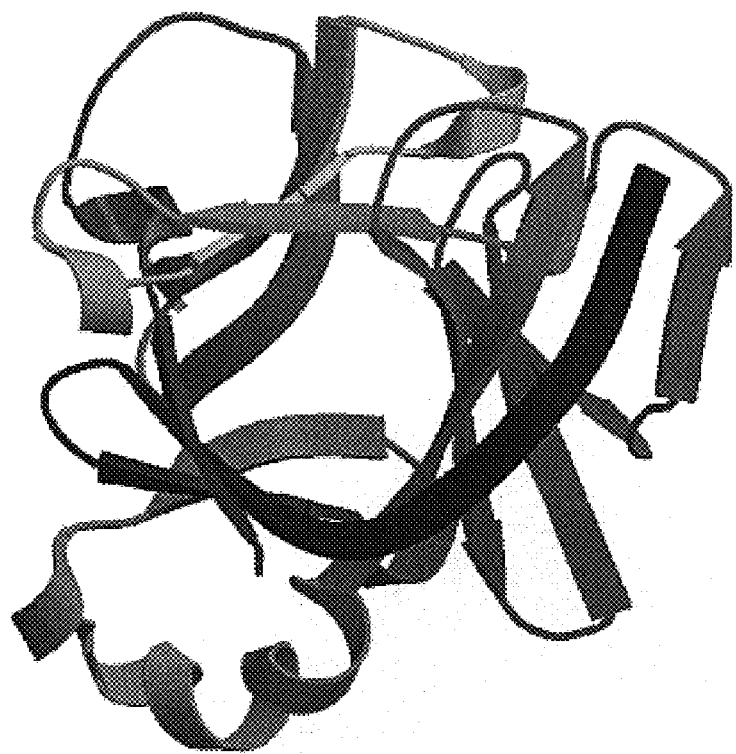
FIG. 1 provides a ribbon diagram of native human IL-18 (C38S) of this invention with the view taken down the axis of the β-barrel and the helical segments represented as ribbons and the β-sheets represented as arrows. The polypeptide chain is rainbow colored with the color blue at the N- and the color red at the C-terminus.
Figure 2:
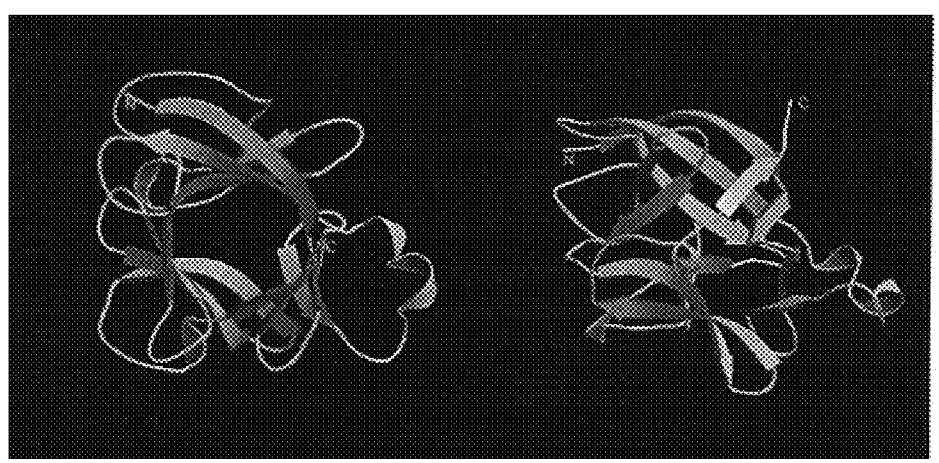
FIG. 2 provides a ribbon diagram of the secondary structure elements of human IL-18. These secondary structural elements of hIL-18 are: β1 2-14, β2 19-22, β3 28-31, α1 38-41, $3_{10}$ helix 42-44, β4 47-54, β5 60-67, β6 71-75, $β_{10}$ helix 77-79, β7 82-84, β8 91-92, β9 101-106, β10 109-117, β11 123-130, β12 133-140, $3_{10}$ helix 147-149, β13 151-154.
Figure 3:
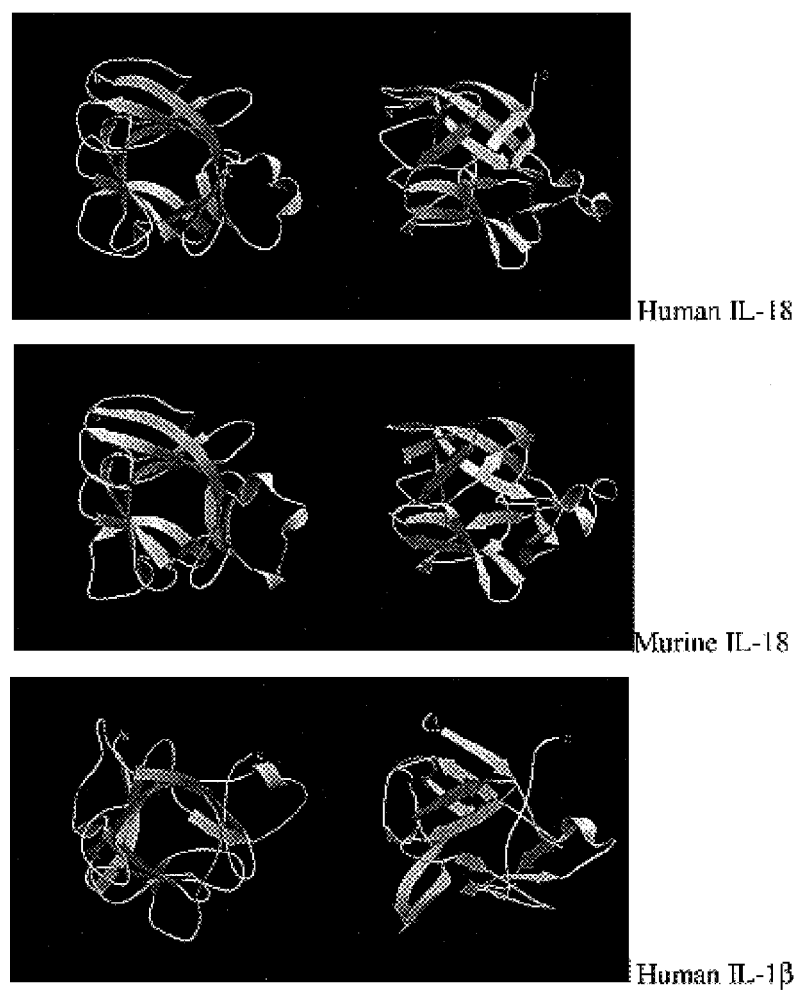
FIG. 3 provides diagrams of murine IL-18, human IL-1β, and human IL-18 structures. Side-by-side comparison of these structures shows the conformational similarities between these structurally related cytokines.
Figure 4:
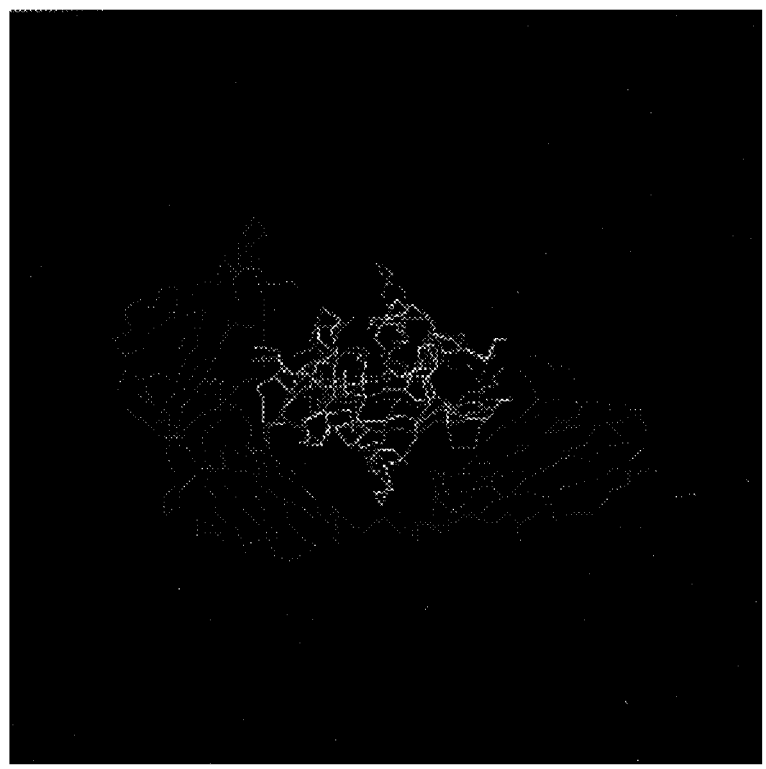
FIG. 4 provides a diagram where the hIL-18 model is superimposed on the IL1β-IL1 receptor complex. Human IL-18 is drawn in a thin yellow line and the IL1β-IL1 is drawn in a thin green line as the cytokine and a red line as the receptor. The diagram sheds light on the manner hIL-18 binds to its receptor, as well as the involvement of amino acid residues in receptor interactions and biological activity.

The present invention provides a novel human IL-18 crystalline structure of the native protein. Based on this structure and molecular models built using related proteins, it provides ways of determining the most likely places to modify the molecule of hIL-18 without compromising its biological activity and methods to use this crystalline form in identifying, improving or antagonizing the biological activity of hIL-18.

The Novel human IL-18 Crystalline Three-Dimensional Structure.

The crystal structure of the human IL-18 in its native form has been determined by molecular replacement and refined to 2.06 Å resolution. The novel human IL-18, like IL1β, is folded into a central, closed β-barrel with an overall β-trefoil fold. The following residues form the three parts of the clover-leaf: (i)10-47 and 150-156, (ii)103-149, and (iii) 47-102 and 1-9. The structure of human IL-18 is expected to be similar to that of the murine IL-18 since the sequences of these IL-18s are highly homologous (65% identity). The information derived from the structure of human IL-18 sheds light on how complexes with pharmacological agents may be formed that would alter the properties of human IL-18, such as half-life and immunogenicity, while maintaining its biological activity. In the absence of structural information of hIL-18-receptor complex, the hIL-18 structure and that of the IL1β-IL1β receptor complex are used as models for interactions between hIL-18 and its receptor and provide rational guidance as to where to place potential agents in the hIL18 molecule. IL1β and hIL-18 have similar overall fold and structures, but large differences in the two structures are apparent near and at the positions of loops. In the IL1β-receptor complex, the residues in the IL1β loops establish important interactions with the receptor, mainly through two surfaces. To identify the residues of IL-18 that may interact with IL-18 receptor, residues of IL-18 were mapped onto the IL1β structure by superimposing 153 Cα atoms of IL1β with IL-18 to achieve an overall root mean square, r.m.s. and deviation of 9 Å. Based on this superposition, hIL-18 is predicted to interact with its receptor via several surfaces. On one of the proposed interacting surfaces, the receptor-IL-18 interface is lined by IL-18 residues: 4-18, 30-37, 107-112, 128-135, and 145-148. On another proposed surface located on the other side of the molecule, the interface is lined by residues: 1-8, 50-55, 89-93, 103-105, and 155-156. This leaves residues 103-149 in hIL-18 free from any interaction with the receptor, and these residues are mostly solvent exposed. This is then proposed to be the best place to attach a derivatization agent (for example, a polyethyleneglycol molecule) that would not compromise hIL-18's receptor binding activity. This proposal is backed up by the observations by Kim, et al., where Glu42 and Lys89 are found to be critical for the interaction of human IL-18 with its receptor. *J. Biol Chem* 277(13):10998-1003 (2002). Glu42 and Lys89 are likewise positioned for interaction with the IL-18 receptor in our model, further validating the use of crystallography modeling in predicting the interacting surfaces and interactions between the cytokine and its receptor.

Table I provides the atomic coordinates of the native human IL-18 (C38S). These coordinates were obtained using a model encompassing residues 1 to 156 in the crystallographic asymmetric unit. The amino acid sequence of the native human IL-18 is provided in SEQ ID NO: 1. However, for the studies described herein, C38S mutant was used.

The atomic coordinates shown in Table I are expected to change upon refinement of the crystal structure, but the deviation that would incur as a result with regard to the Cα atoms is not expected to substantially exceed an r.m.s. of 1.0-1.5 Å. Similarly, bond angles and bond lengths will vary insignificantly as routinely observed with other proteins. Engh, et al. (1991) *Acta Crystallogr. A*47, 392-400. The inter-atomic interactions will remain unchanged, within experimental error. The relative conformation and orientation or the positioning of residues in the receptor binding site will likewise be unaffected.

Mutants and Derivatives

The invention further provides homologues, co-complexes, mutants and derivatives of the human IL-18 crystal structure of the invention.

The term "cytokine", as used herein, means a protein modulating the growth and functional activities of immune cells.

The term "homolog", as used herein, means a protein having at least 30% amino acid sequence identity with a functional domain of human IL-18. Preferably the percentage identity will be 40, or 50%, more preferably 60 or 70% and most preferably 80 or 90%. A 95% identity is most particularly preferred.

The term "co-complex", as used herein, means the human IL-18 or a mutant or homologue of the human IL-18 in covalent or non-covalent association with a chemical entity or compound.

The term "mutant", as used herein, means the Human IL-18 polypeptide, i.e., a polypeptide displaying the biological activity of wild-type Human IL-18 activity, characterized by the replacement of at least one amino acid from the wild-type IL-18 sequence. Such a mutant may be prepared, for example, by expression of the human IL-18 cDNA previously altered in its coding sequence by oligonucleotide-directed mutagenesis.

The term "r.m.s.", as used herein, means root mean square. It represents the standard deviation of the data collection.

The term "pro-IL18", as used herein, means the inactive, precursor form of mature IL18. Mature IL18 does not contain the "pro-fragment" and is biologically active.

The term "molecular replacement", as used herein, means a method of solving crystal structure using the atomic coordinates of a structurally related molecule.

Human IL-18 mutants may also be generated by site-specific incorporation of unnatural amino acids into the Human IL-18 protein using the general biosynthetic method of Noren, et al., *Science,* 244:182-188 (1989). In this method, the nucleotides encoding the amino acid of interest in wild-type Human IL-18 is replaced by a "blank" nonsense codon, TAG, using oligonucleotide-directed mutagenesis. A suppressor directed against this codon is then chemically aminoacylated in vitro with the desired unnatural amino acid. The aminoacylated residue is then added to an in vitro translation system to yield a mutant Human IL-18 enzyme with the site-specific incorporated unnatural amino acid.

Selenocysteine or selenomethionine may be incorporated into wild-type or mutant cytokine by expression of Human IL-18-encoding cDNAs in auxotrophic *E. coli* strains. Hendrickson, et al., *EMBO J.,* 9(5):1665-1672 (1990). In this embodiment, the wild-type or mutated cytokine cDNA may be expressed in a host organism on a growth medium depleted of either natural cysteine or methionine or both, but enriched with selenocysteine or selenomethionine or both.

The term "heavy atom derivative" refers to derivatives of Human IL-18 produced by chemically modifying a crystal of Human IL-18. In practice, a crystal is immersed in a solution containing the desired metal salt, or organometallic compound, e.g., lead chloride, gold thiomalate, thimerosal or uranyl acetate, which upon diffusion into the protein crystal can bind to the protein. The location of the bound heavy metal atom site(s) can be determined by X-ray diffraction analysis of the soaked crystal. This information, in turn, is used to generate the phase angle information needed to construct a three-dimensional electron density map from which a model of the atomic structure of the enzyme is derived Blundell, et al., *PROTEIN CRYSTALLOGRAPHY*, Academic Press (1976).

Methods of Identifying Agonist or Antagonists of the Novel Human IL-18

Crystalline Structure

Another aspect of this invention involves a method for identifying agonists or antagonists of a human IL-18 through the crystal structure described herein. The novel human IL-18 crystalline structure of the invention permits the identification of agonists or antagonists of its cytokine activity. Such agonist/antagonists may be competitive, binding to all or a portion of the receptor for the human IL-18; or non-competitive and bind to and inhibit IL-18 activity whether or not it is bound to the receptor.

One embodiment probes the human IL-18 crystal of the invention with a variety of different chemical molecules to determine optimal sites either for interactions between such candidate angonist/antagonist molecules and hIL-18, or alternatively, for cellular activities. For example, high resolution X-ray diffraction data collected from crystals saturated with solvent allows the determination of binding positions for solvent molecule. Small molecules that would bind tightly to those sites can then be designed, synthesized and tested for their human IL-18 agonist/antagonist activities.

Another embodiment screens computationally small molecule databases for chemical entities or compounds that can bind in whole, or in part, to human IL-18 or human IL-18 receptor, or both. This screening method and its utility is well known in the art. For example, such computer modeling techniques were described in a PCT application WO 97/16177, published on May 9, 1997.

Once identified by modeling, the agonist/antagonist may then be tested for biological activity. For example, the molecules identified may be introduced via standard screening formats into enzymatic activity assays to determine the inhibitory activity of the compounds, or alternatively, binding assays to determine binding. One particularly preferred assay format is the enzyme-linked immunosorbent assay (ELISA). This and other assay formats are well known in the art and thus are not limitations to the present invention.

The following examples illustrate various aspects of this invention. This invention is not to be limited in scope by the specific embodiments described below. Indeed, various modifications of the invention in addition to those described herein will become apparent to those skilled in the art from the foregoing description. Such modifications are intended to fall within the scope of the appended claims. The disclosures of patents, patent applications and publications cited herein are incorporated by reference in their entireties.

EXAMPLES

Biological Methods

Example 1

The Purification of the Human IL-18 C38S Mutant in *Escherichia coli*.

Human proIL-18 was expressed in *E. coli* as a soluble protein with an N-terminal hexa-His tag. ProIL-18 was purified with a Ni-NTA agarose column and mature IL-18 was obtained by cleaving the pro-domain with Caspase 5. The C38S mutant of IL-18 was engineered to prevent the usual occurrence of an intra-disulfide bond between C38 and C68 in wild type IL-18 at neutral pH.

*E. coli* cells were suspended (10 ml/g) in 50 mM Tris (pH 8), 500 mM NaCl, 5% Glycerol, 10 mM 2-mercaptoethanol (buffer A) containing 1 ug/mL pepstatin A and 0.4 mM phenylmethylsulfonyl flouride. Cells were homogenized and then lysed by two passes through a microfluidizer (M110-Y, Microfludics) at 12,000 psi. Cell debris was removed by centrifugation at 30,000 g for 30 min. The supernatant was applied to a Ni-NTA agarose column and washed with 3 column volumes of buffer A. The column was then washed with 3 column volumes of 30 mM imidazole in buffer A and proIL-18 was eluted with 300 mM imidazole in buffer A, which was then dialyzed into 25 mM HEPES (pH 7.5), 100 mM NaCl, 10 mM 2-mercaptoethanol. The hexa-His tagged "pro" domain was removed by cleavage with hexa-His tagged Caspase 5 at a proIL-18:Caspase 5 ratio of 50:1 by weight for 2 hours at room temperature. The salt concentration of the protein mixture was adjusted to 0.5M NaCl and the mixture was then applied to a Ni-NTA agarose column. Mature IL-18 flowed through the column, while trace amount of intact proIL-18, the "pro" domain, Caspase5 and other minor contaminants were bound to the Ni-NTA column. Mature hIL-18 in the Ni-NTA flow-through fraction was diluted 1:10 with 25 mM Tris (pH 7.5), 5 mM 2-mercaptoethanol (buffer B). The protein solution was then applied to a MonoQ column, and elution was carried out with a linear gradient of 0-0.3M NaCl in Buffer B, preferably in 20 column volumes. Fractions collected after the column containing IL-18 were pooled based on absorbance at 280 nm wavelength and results of SDS-PAGE. The pool was then applied to a HiLoad 26/60 Superdex 75 prep grade column, which was pre-equilibrated with 25 mM Tris (pH 8), 50 mM NaCl, 5 mM 2-mercaptoethanol, 0.1 mM EDTA, and the elution of the desired protein was carried out at a flow rate of 2.5 mL/min. IL-18 was eluted as a single symmetrical peak. Fractions corresponding to this peak were pooled and the protein in the pool was then concentrated to 10.2 mg/mL for crystallization. This resulting product was greater than 95% pure by SDS-PAGE and has the desired activity. N-terminal amino acid analysis was used to confirm its identity.

The invention described herein provides a method for defining ligand interactions with IL-18 and its receptor:

1.A. Effects of ligand binding upon enzyme intrinsicfluorescence generated by tryptophan residues. Binding of either a natural ligand or a derivatized molecule may result in conformational changes that alter protein intrinsic fluorescence. Using stopped-flow fluorescence technology, one can use this change in intrinsic fluorescence to define the microscopic rate constants that are associated with ligand binding. Alternatively, one can use steady-state fluorescence titration methods to generate the overall dissociation constant for binding. Standard methods are applied in assessing the acquired parameters.

Example 2

Crystallization, Structure Determination and Refinement of the Crystal Structure of the Human IL-18

2.A. Crystallization

The human IL-18 C38S crystals grew as hexagonal rods from sitting drops equilibrated through the vapor phase at room temperature against a reservoir of 500 µL solution containing 20% polyethylene glycol (PEG), 0.07 mM sodium citrate at pH 5.6, and 0.133 M ammonium acetate for 2-3 weeks in Cryschem plates. The drops contained 2 ul of protein at 10 mg/ml in 50 mM NaCl, 25 mM tris at pH 8, 0.1 mM EDTA and 5 mM·-mercaptoethanol. The crystals belong to the space group P6(1) with unit cell dimensions a=71.4 Å, b=71.4 Å, c=88.7 Å, $\alpha=\beta=90°$, $\gamma 120°$, and one copy of the Human IL-18 in the asymmetric unit.

2.B. X-ray Diffraction Data Collection

We collected the x-ray diffraction data through a single human IL-18 (C38S) crystal suspended by a nylon loop and flash frozen under the cold stream of nitrogen gas. The diffraction parameters were generated by an ADSC Quantum 210 charge-coupled device at the 171D beamline at the Advanced Photon Source, Argonne National Laboratory, Illinois. The wavelength of the monochromatic x-ray beam was set at 1.000 Å. The reciprocal space was sampled at 1.0° oscillation steps around the φ goniostat's axis. The data were processed with HKL2000. Otwinowski, Z. in *Proceedings of the CCP4 Study Weekend: "Data Collection and Processing"*, 29-30 January, SERC Daresbury Laboratory, England (1993).

2.C. Structure Determination

The crystal structure of human IL-18 was determined by molecular replacement with the program package AMoRe

[Navaza, *J. Acta Cryst.* A50, 157-163 (1994)] using the crystal structure of murine IL-18 stripped of solvent molecules as search model as the murine and the human IL-18 proteins share 65% amino acid sequence identity. The search molecule was placed in an orthogonal cell of dimensions 100 Å×100 Å×100 Å. The cross rotation and translation searches were carried out using data from 20 Å to 4 Å resolutions and a radius of integration of 25 Å. The top solution of the cross rotation function corresponded to the IL-18 molecule in the asymmetric unit and was unambiguously discriminated from the noise peaks. The search for correct translation yielded a solution with an R-factor of 0.45 and a correlation coefficient of 0.47 after rigid body refinement in AMoRe.

2.D. Model Building and Refinement

The native hIL-18 structure was built from the rotation and translation operations found by molecular replacement using the murine IL-18 structure. The human IL-18 structure was built following the 2Fo-Fc and Fo-Fc electron density maps. According to these maps, one can establish the human IL-18 rough model by replacing the amino acids present in the murine structure with those in the human protein, as well as by adding or deleting residues. We used the interactive computer graphics program XTALVIEW to perform these manipulations. McRee *J. Structural Biology* 125, 156-165 (1999). This rough model was then subjected to rounds of simulated annealing, positional and B-factor refinement using CNX [Brunger, et al., *Science,* 235, 458-460 (1987)] and REFMAC [Murshudov, et al. *Acta Crystallographica* D5, 240-255 (1997)] followed by manual intervention. The refinement and manual rebuilding was monitored by the quality of the 2Fo-Fc and Fo-Fc electron density maps, as well as the value of the crystallographic R and $R_{free}$. Throughout the refinement, reflection data from infinity to 2.06 Å were used, when necessary, accounting for the bulk solvent inside the crystal, which may contribute to the diffraction intensity. The final model of the human IL-18 (C38S) encompasses residues 1 to 156 [SEQ ID NO: 1], and 208 water molecules. The R-factor of the model is 0.16 and the $R_{free}$ is 0.19 for 15,011 reflections. The r.m.s. deviations from the standard geometry [Engh, et al., *Acta Cryst.* A47, 392-400 (1991)] are 0.013 Å for bond lengths, and 1.5° for bond angles.

TABLE I

The atomic coordinates of an altered human IL-18 structure; SEQ ID No: 1 with a C38S substitution.
($P6_1$)a = 71.4°, b = 71.4°, c = 88.7°, $\alpha,\beta$ = 90° and $\gamma$ = 120°

| ATOM | 1 | N | TYR | A | 1 | 8.630 | 49.746 | −20.359 | 1.00 | 14.94 | N |
|---|---|---|---|---|---|---|---|---|---|---|---|
| ATOM | 3 | CA | TYR | A | 1 | 7.622 | 50.752 | −19.957 | 1.00 | 14.81 | C |
| ATOM | 5 | CB | TYR | A | 1 | 7.014 | 51.448 | −21.187 | 1.00 | 15.67 | C |
| ATOM | 8 | CG | TYR | A | 1 | 6.353 | 50.513 | −22.163 | 1.00 | 15.20 | C |
| ATOM | 9 | CD1 | TYR | A | 1 | 5.018 | 50.210 | −22.052 | 1.00 | 16.18 | C |
| ATOM | 11 | CE1 | TYR | A | 1 | 4.398 | 49.361 | −22.952 | 1.00 | 15.83 | C |
| ATOM | 13 | CZ | TYR | A | 1 | 5.131 | 48.807 | −23.970 | 1.00 | 17.36 | C |
| ATOM | 14 | OH | TYR | A | 1 | 4.512 | 47.958 | −24.847 | 1.00 | 18.90 | O |
| ATOM | 16 | CE2 | TYR | A | 1 | 6.473 | 49.093 | −24.104 | 1.00 | 17.52 | C |
| ATOM | 18 | CD2 | TYR | A | 1 | 7.071 | 49.951 | −23.208 | 1.00 | 17.35 | C |
| ATOM | 20 | C | TYR | A | 1 | 6.532 | 50.086 | −19.120 | 1.00 | 14.70 | C |
| ATOM | 21 | O | TYR | A | 1 | 6.242 | 48.889 | −19.271 | 1.00 | 16.08 | O |
| ATOM | 24 | N | PHE | A | 2 | 6.032 | 50.833 | −18.155 | 1.00 | 14.03 | N |
| ATOM | 26 | CA | PHE | A | 2 | 4.963 | 50.411 | −17.278 | 1.00 | 13.54 | C |
| ATOM | 28 | CB | PHE | A | 2 | 5.378 | 50.722 | −15.844 | 1.00 | 13.04 | C |
| ATOM | 31 | CG | PHE | A | 2 | 6.744 | 50.244 | −15.468 | 1.00 | 12.18 | C |
| ATOM | 32 | CD1 | PHE | A | 2 | 6.915 | 49.016 | −14.847 | 1.00 | 13.65 | C |
| ATOM | 34 | CE1 | PHE | A | 2 | 8.160 | 48.576 | −14.433 | 1.00 | 12.75 | C |
| ATOM | 36 | CZ | PHE | A | 2 | 9.269 | 49.381 | −14.620 | 1.00 | 14.76 | C |
| ATOM | 38 | CE2 | PHE | A | 2 | 9.127 | 50.623 | −15.241 | 1.00 | 13.52 | C |
| ATOM | 40 | CD2 | PHE | A | 2 | 7.854 | 51.057 | −15.649 | 1.00 | 12.68 | C |
| ATOM | 42 | C | PHE | A | 2 | 3.606 | 51.076 | −17.477 | 1.00 | 14.09 | C |
| ATOM | 43 | O | PHE | A | 2 | 3.511 | 52.287 | −17.726 | 1.00 | 13.42 | O |
| ATOM | 44 | N | GLY | A | 3 | 2.547 | 50.290 | −17.294 | 1.00 | 14.44 | N |
| ATOM | 46 | CA | GLY | A | 3 | 1.187 | 50.806 | −17.348 | 1.00 | 14.64 | C |
| ATOM | 49 | C | GLY | A | 3 | 0.397 | 50.402 | −16.119 | 1.00 | 14.74 | C |
| ATOM | 50 | O | GLY | A | 3 | 0.292 | 49.232 | −15.795 | 1.00 | 14.03 | O |
| ATOM | 51 | N | LYS | A | 4 | −0.204 | 51.371 | −15.444 | 1.00 | 15.75 | N |
| ATOM | 53 | CA | LYS | A | 4 | −0.942 | 51.083 | −14.222 | 1.00 | 17.05 | C |
| ATOM | 55 | CB | LYS | A | 4 | −1.367 | 52.366 | −13.504 | 1.00 | 17.49 | C |
| ATOM | 58 | CG | LYS | A | 4 | −1.976 | 52.087 | −12.151 | 1.00 | 19.63 | C |
| ATOM | 61 | CD | LYS | A | 4 | −2.051 | 53.336 | −11.284 | 1.00 | 24.07 | C |
| ATOM | 64 | CE | LYS | A | 4 | −3.193 | 54.244 | −11.670 | 1.00 | 26.40 | C |
| ATOM | 67 | NZ | LYS | A | 4 | −3.087 | 55.505 | −10.873 | 1.00 | 31.21 | N |
| ATOM | 71 | C | LYS | A | 4 | −2.157 | 50.208 | −14.457 | 1.00 | 17.39 | C |
| ATOM | 72 | O | LYS | A | 4 | −2.955 | 50.480 | −15.345 | 1.00 | 16.52 | O |
| ATOM | 73 | N | LEU | A | 5 | −2.298 | 49.173 | −13.627 | 1.00 | 17.66 | N |
| ATOM | 75 | CA | LEU | A | 5 | −3.398 | 48.220 | −13.739 | 1.00 | 19.03 | C |
| ATOM | 77 | CB | LEU | A | 5 | −2.855 | 46.800 | −13.671 | 1.00 | 19.09 | C |
| ATOM | 80 | CG | LEU | A | 5 | −2.134 | 46.301 | −14.916 | 1.00 | 19.65 | C |
| ATOM | 82 | CD1 | LEU | A | 5 | −1.691 | 44.853 | −14.704 | 1.00 | 21.62 | C |
| ATOM | 86 | CD2 | LEU | A | 5 | −3.046 | 46.419 | −16.101 | 1.00 | 19.89 | C |
| ATOM | 90 | C | LEU | A | 5 | −4.497 | 48.348 | −12.678 | 1.00 | 20.37 | C |
| ATOM | 91 | O | LEU | A | 5 | −5.690 | 48.249 | −12.987 | 1.00 | 21.59 | O |
| ATOM | 92 | N | GLU | A | 6 | −4.097 | 48.516 | −11.436 | 1.00 | 20.59 | N |
| ATOM | 94 | CA | GLU | A | 6 | −5.034 | 48.628 | −10.325 | 1.00 | 21.77 | C |

TABLE I-continued

The atomic coordinates of an altered human IL-18 structure; SEQ
ID No: 1 with a C38S substitution.
(P6$_1$)a = 71.4°, b = 71.4°, c = 88.7°, α,β = 90° and γ = 120°

| ATOM | 96 | CB | GLU | A | 6 | −5.712 | 47.296 | −10.065 | 1.00 | 22.73 | C |
|---|---|---|---|---|---|---|---|---|---|---|---|
| ATOM | 99 | CG | GLU | A | 6 | −4.724 | 46.187 | −9.798 | 1.00 | 26.49 | C |
| ATOM | 102 | CD | GLU | A | 6 | −5.382 | 44.911 | −9.318 | 1.00 | 31.62 | C |
| ATOM | 103 | OE1 | GLU | A | 6 | −4.684 | 43.887 | −9.245 | 1.00 | 32.77 | O |
| ATOM | 104 | OE2 | GLU | A | 6 | −6.595 | 44.930 | −9.000 | 1.00 | 36.73 | O |
| ATOM | 105 | C | GLU | A | 6 | −4.268 | 49.047 | −9.080 | 1.00 | 20.79 | C |
| ATOM | 106 | O | GLU | A | 6 | −3.034 | 48.979 | −9.040 | 1.00 | 20.65 | O |
| ATOM | 107 | N | SER | A | 7 | −5.017 | 49.490 | −8.086 | 1.00 | 20.46 | N |
| ATOM | 109 | CA | SER | A | 7 | −4.492 | 49.930 | −6.811 | 1.00 | 20.67 | C |
| ATOM | 111 | CB | SER | A | 7 | −4.672 | 51.438 | −6.642 | 1.00 | 20.28 | C |
| ATOM | 114 | OG | SER | A | 7 | −3.791 | 52.137 | −7.506 | 1.00 | 24.79 | O |
| ATOM | 116 | C | SER | A | 7 | −5.276 | 49.228 | −5.710 | 1.00 | 20.43 | C |
| ATOM | 117 | O | SER | A | 7 | −6.474 | 49.004 | −5.856 | 1.00 | 19.94 | O |
| ATOM | 118 | N | LYS | A | 8 | −4.587 | 48.889 | −4.624 | 1.00 | 19.55 | N |
| ATOM | 120 | CA | LYS | A | 8 | −5.213 | 48.272 | −3.458 | 1.00 | 19.39 | C |
| ATOM | 122 | CB | LYS | A | 8 | −4.888 | 46.787 | −3.412 | 1.00 | 20.02 | C |
| ATOM | 125 | CG | LYS | A | 8 | −5.493 | 45.978 | −4.540 | 1.00 | 21.94 | C |
| ATOM | 128 | CD | LYS | A | 8 | −5.161 | 44.528 | −4.333 | 1.00 | 24.93 | C |
| ATOM | 131 | CE | LYS | A | 8 | −5.776 | 43.657 | −5.419 | 1.00 | 26.32 | C |
| ATOM | 134 | NZ | LYS | A | 8 | −5.403 | 42.241 | −5.206 | 1.00 | 27.21 | N |
| ATOM | 138 | C | LYS | A | 8 | −4.701 | 48.922 | −2.174 | 1.00 | 18.17 | C |
| ATOM | 139 | O | LYS | A | 8 | −3.485 | 49.106 | −2.006 | 1.00 | 16.83 | O |
| ATOM | 140 | N | LEU | A | 9 | −5.629 | 49.254 | −1.278 | 1.00 | 17.07 | N |
| ATOM | 142 | CA | LEU | A | 9 | −5.296 | 49.794 | 0.032 | 1.00 | 16.73 | C |
| ATOM | 144 | CB | LEU | A | 9 | −6.529 | 50.363 | 0.704 | 1.00 | 17.11 | C |
| ATOM | 147 | CG | LEU | A | 9 | −7.184 | 51.496 | −0.085 | 1.00 | 19.58 | C |
| ATOM | 149 | CD1 | LEU | A | 9 | −8.444 | 52.030 | 0.604 | 1.00 | 22.37 | C |
| ATOM | 153 | CD2 | LEU | A | 9 | −6.196 | 52.621 | −0.295 | 1.00 | 20.80 | C |
| ATOM | 157 | C | LEU | A | 9 | −4.749 | 48.596 | 0.821 | 1.00 | 15.48 | C |
| ATOM | 158 | O | LEU | A | 9 | −5.378 | 47.536 | 0.889 | 1.00 | 15.33 | O |
| ATOM | 159 | N | SER | A | 10 | −3.583 | 48.802 | 1.401 | 1.00 | 13.41 | N |
| ATOM | 161 | CA | SER | A | 10 | −2.827 | 47.716 | 1.965 | 1.00 | 13.59 | C |
| ATOM | 163 | CB | SER | A | 10 | −1.726 | 47.297 | 0.989 | 1.00 | 13.55 | C |
| ATOM | 166 | OG | SER | A | 10 | −2.220 | 47.028 | −0.310 | 1.00 | 14.09 | O |
| ATOM | 168 | C | SER | A | 10 | −2.140 | 48.081 | 3.251 | 1.00 | 12.56 | C |
| ATOM | 169 | O | SER | A | 10 | −1.846 | 49.255 | 3.499 | 1.00 | 12.15 | O |
| ATOM | 170 | N | VAL | A | 11 | −1.897 | 47.050 | 4.050 | 1.00 | 11.93 | N |
| ATOM | 172 | CA | VAL | A | 11 | −1.124 | 47.153 | 5.279 | 1.00 | 12.46 | C |
| ATOM | 174 | CB | VAL | A | 11 | −1.925 | 46.668 | 6.502 | 1.00 | 12.74 | C |
| ATOM | 176 | CG1 | VAL | A | 11 | −1.025 | 46.547 | 7.736 | 1.00 | 13.13 | C |
| ATOM | 180 | CG2 | VAL | A | 11 | −3.047 | 47.635 | 6.788 | 1.00 | 13.37 | C |
| ATOM | 184 | C | VAL | A | 11 | 0.124 | 46.292 | 5.120 | 1.00 | 12.52 | C |
| ATOM | 185 | O | VAL | A | 11 | 0.050 | 45.111 | 4.755 | 1.00 | 12.52 | O |
| ATOM | 186 | N | ILE | A | 12 | 1.275 | 46.880 | 5.395 | 1.00 | 12.68 | N |
| ATOM | 188 | CA | ILE | A | 12 | 2.537 | 46.173 | 5.242 | 1.00 | 12.62 | C |
| ATOM | 190 | CB | ILE | A | 12 | 3.509 | 47.034 | 4.439 | 1.00 | 12.98 | C |
| ATOM | 192 | CG1 | ILE | A | 12 | 2.979 | 47.227 | 3.022 | 1.00 | 13.10 | C |
| ATOM | 195 | CD1 | ILE | A | 12 | 3.709 | 48.301 | 2.231 | 1.00 | 14.66 | C |
| ATOM | 199 | CG2 | ILE | A | 12 | 4.890 | 46.401 | 4.443 | 1.00 | 13.83 | C |
| ATOM | 203 | C | ILE | A | 12 | 3.120 | 45.900 | 6.625 | 1.00 | 12.91 | C |
| ATOM | 204 | O | ILE | A | 12 | 3.212 | 46.819 | 7.446 | 1.00 | 12.37 | O |
| ATOM | 205 | N | ARG | A | 13 | 3.520 | 44.657 | 6.869 | 1.00 | 12.43 | N |
| ATOM | 207 | CA | ARG | A | 13 | 4.105 | 44.265 | 8.153 | 1.00 | 13.04 | C |
| ATOM | 209 | CB | ARG | A | 13 | 3.184 | 43.292 | 8.899 | 1.00 | 13.05 | C |
| ATOM | 212 | CG | ARG | A | 13 | 1.818 | 43.843 | 9.322 | 1.00 | 14.08 | C |
| ATOM | 215 | CD | ARG | A | 13 | 0.904 | 42.765 | 9.928 | 1.00 | 13.91 | C |
| ATOM | 218 | NE | ARG | A | 13 | −0.351 | 43.276 | 10.454 | 1.00 | 13.75 | N |
| ATOM | 220 | CZ | ARG | A | 13 | −1.458 | 43.447 | 9.737 | 1.00 | 15.14 | C |
| ATOM | 221 | NH1 | ARG | A | 13 | −1.462 | 43.161 | 8.440 | 1.00 | 14.09 | N |
| ATOM | 224 | NH2 | ARG | A | 13 | −2.567 | 43.901 | 10.321 | 1.00 | 13.65 | N |
| ATOM | 227 | C | ARG | A | 13 | 5.447 | 43.569 | 7.954 | 1.00 | 13.59 | C |
| ATOM | 228 | O | ARG | A | 13 | 5.634 | 42.851 | 6.975 | 1.00 | 12.69 | O |
| ATOM | 229 | N | ASN | A | 14 | 6.379 | 43.792 | 8.880 | 1.00 | 15.35 | N |
| ATOM | 231 | CA | ASN | A | 14 | 7.633 | 43.049 | 8.867 | 1.00 | 16.85 | C |
| ATOM | 233 | CB | ASN | A | 14 | 8.780 | 43.805 | 9.553 | 1.00 | 16.93 | C |
| ATOM | 236 | CG | ASN | A | 14 | 8.556 | 44.042 | 11.034 | 1.00 | 16.46 | C |
| ATOM | 237 | OD1 | ASN | A | 14 | 7.799 | 43.336 | 11.697 | 1.00 | 13.43 | O |
| ATOM | 238 | ND2 | ASN | A | 14 | 9.263 | 45.048 | 11.568 | 1.00 | 16.09 | N |
| ATOM | 241 | C | ASN | A | 14 | 7.368 | 41.676 | 9.499 | 1.00 | 18.25 | C |
| ATOM | 242 | O | ASN | A | 14 | 6.252 | 41.390 | 9.918 | 1.00 | 18.18 | O |
| ATOM | 243 | N | LEU | A | 15 | 8.375 | 40.826 | 9.576 | 1.00 | 20.32 | N |
| ATOM | 245 | CA | LEU | A | 15 | 8.124 | 39.467 | 10.062 | 1.00 | 21.88 | C |
| ATOM | 247 | CB | LEU | A | 15 | 9.234 | 38.507 | 9.627 | 1.00 | 22.23 | C |
| ATOM | 250 | CG | LEU | A | 15 | 9.353 | 38.222 | 8.114 | 1.00 | 22.83 | C |
| ATOM | 252 | CD1 | LEU | A | 15 | 9.887 | 36.778 | 7.890 | 1.00 | 22.15 | C |

TABLE I-continued

The atomic coordinates of an altered human IL-18 structure; SEQ ID No: 1 with a C38S substitution.
(P6₁) a = 71.4°, b = 71.4°, c = 88.7°, α,β = 90° and γ = 120°

| ATOM | 256 | CD2 | LEU | A | 15 | 8.051 | 38.413 | 7.366 | 1.00 | 22.19 | C |
|---|---|---|---|---|---|---|---|---|---|---|---|
| ATOM | 260 | C | LEU | A | 15 | 7.895 | 39.420 | 11.582 | 1.00 | 22.33 | C |
| ATOM | 261 | O | LEU | A | 15 | 7.426 | 38.423 | 12.109 | 1.00 | 23.76 | O |
| ATOM | 262 | N | ASN | A | 16 | 8.195 | 40.504 | 12.278 | 1.00 | 22.29 | N |
| ATOM | 264 | CA | ASN | A | 16 | 7.878 | 40.564 | 13.697 | 1.00 | 21.75 | C |
| ATOM | 266 | CB | ASN | A | 16 | 8.905 | 41.415 | 14.418 | 1.00 | 21.71 | C |
| ATOM | 269 | CG | ASN | A | 16 | 10.266 | 40.727 | 14.533 | 1.00 | 22.48 | C |
| ATOM | 270 | OD1 | ASN | A | 16 | 11.306 | 41.387 | 14.586 | 1.00 | 22.21 | O |
| ATOM | 271 | ND2 | ASN | A | 16 | 10.252 | 39.402 | 14.596 | 1.00 | 21.88 | N |
| ATOM | 274 | C | ASN | A | 16 | 6.480 | 41.133 | 13.903 | 1.00 | 21.33 | C |
| ATOM | 275 | O | ASN | A | 16 | 6.118 | 41.509 | 14.999 | 1.00 | 20.43 | O |
| ATOM | 276 | N | ASP | A | 17 | 5.705 | 41.215 | 12.832 | 1.00 | 20.83 | N |
| ATOM | 278 | CA | ASP | A | 17 | 4.334 | 41.740 | 12.884 | 1.00 | 20.97 | C |
| ATOM | 280 | CB | ASP | A | 17 | 3.430 | 40.834 | 13.697 | 1.00 | 22.16 | C |
| ATOM | 283 | CG | ASP | A | 17 | 3.011 | 39.651 | 12.901 | 1.00 | 26.40 | C |
| ATOM | 284 | OD1 | ASP | A | 17 | 2.402 | 39.847 | 11.812 | 1.00 | 32.51 | O |
| ATOM | 285 | OD2 | ASP | A | 17 | 3.303 | 38.496 | 13.221 | 1.00 | 30.36 | O |
| ATOM | 286 | C | ASP | A | 17 | 4.186 | 43.207 | 13.315 | 1.00 | 18.94 | C |
| ATOM | 287 | O | ASP | A | 17 | 3.136 | 43.632 | 13.802 | 1.00 | 18.69 | O |
| ATOM | 288 | N | GLN | A | 18 | 5.247 | 43.964 | 13.108 | 1.00 | 17.49 | N |
| ATOM | 290 | CA | GLN | A | 18 | 5.198 | 45.399 | 13.285 | 1.00 | 16.92 | C |
| ATOM | 292 | CB | GLN | A | 18 | 6.590 | 45.923 | 13.586 | 1.00 | 16.50 | C |
| ATOM | 295 | CG | GLN | A | 18 | 7.108 | 45.430 | 14.943 | 1.00 | 17.24 | C |
| ATOM | 298 | CD | GLN | A | 18 | 8.544 | 45.802 | 15.159 | 1.00 | 19.07 | C |
| ATOM | 299 | OE1 | GLN | A | 18 | 9.351 | 45.673 | 14.238 | 1.00 | 19.30 | O |
| ATOM | 300 | NE2 | GLN | A | 18 | 8.874 | 46.289 | 16.354 | 1.00 | 20.48 | N |
| ATOM | 303 | C | GLN | A | 18 | 4.626 | 46.021 | 12.013 | 1.00 | 16.02 | C |
| ATOM | 304 | O | GLN | A | 18 | 4.992 | 45.613 | 10.904 | 1.00 | 16.32 | O |
| ATOM | 305 | N | VAL | A | 19 | 3.750 | 47.011 | 12.178 | 1.00 | 15.43 | N |
| ATOM | 307 | CA | VAL | A | 19 | 3.060 | 47.647 | 11.055 | 1.00 | 14.72 | C |
| ATOM | 309 | CB | VAL | A | 19 | 1.563 | 48.003 | 11.380 | 1.00 | 14.93 | C |
| ATOM | 311 | CG1A | VAL | A | 19 | 0.810 | 48.788 | 10.288 | 0.50 | 14.38 | C |
| ATOM | 312 | CG1B | VAL | A | 19 | 1.347 | 48.282 | 12.814 | 0.50 | 15.70 | C |
| ATOM | 319 | CG2A | VAL | A | 19 | 0.845 | 47.018 | 12.321 | 0.50 | 14.75 | C |
| ATOM | 320 | CG2B | VAL | A | 19 | 1.068 | 49.159 | 10.542 | 0.50 | 14.36 | C |
| ATOM | 327 | C | VAL | A | 19 | 3.779 | 48.896 | 10.566 | 1.00 | 14.47 | C |
| ATOM | 328 | O | VAL | A | 19 | 4.161 | 49.761 | 11.354 | 1.00 | 13.42 | O |
| ATOM | 329 | N | LEU | A | 20 | 3.964 | 48.963 | 9.259 | 1.00 | 14.08 | N |
| ATOM | 331 | CA | LEU | A | 20 | 4.587 | 50.111 | 8.636 | 1.00 | 14.51 | C |
| ATOM | 333 | CB | LEU | A | 20 | 4.888 | 49.830 | 7.170 | 1.00 | 14.38 | C |
| ATOM | 336 | CG | LEU | A | 20 | 5.474 | 51.015 | 6.388 | 1.00 | 14.85 | C |
| ATOM | 338 | CD1 | LEU | A | 20 | 6.883 | 51.390 | 6.861 | 1.00 | 14.80 | C |
| ATOM | 342 | CD2 | LEU | A | 20 | 5.491 | 50.702 | 4.932 | 1.00 | 14.95 | C |
| ATOM | 346 | C | LEU | A | 20 | 3.655 | 51.306 | 8.766 | 1.00 | 15.20 | C |
| ATOM | 347 | O | LEU | A | 20 | 2.445 | 51.191 | 8.524 | 1.00 | 15.29 | O |
| ATOM | 348 | N | PHE | A | 21 | 4.212 | 52.444 | 9.169 | 1.00 | 15.37 | N |
| ATOM | 350 | CA | PHE | A | 21 | 3.454 | 53.695 | 9.231 | 1.00 | 16.45 | C |
| ATOM | 352 | CB | PHE | A | 21 | 2.786 | 53.894 | 10.604 | 1.00 | 16.28 | C |
| ATOM | 355 | CG | PHE | A | 21 | 3.720 | 54.366 | 11.701 | 1.00 | 16.48 | C |
| ATOM | 356 | CD1 | PHE | A | 21 | 4.552 | 53.483 | 12.370 | 1.00 | 17.40 | C |
| ATOM | 358 | CE1 | PHE | A | 21 | 5.419 | 53.941 | 13.411 | 1.00 | 18.30 | C |
| ATOM | 360 | CZ | PHE | A | 21 | 5.412 | 55.294 | 13.771 | 1.00 | 18.26 | C |
| ATOM | 362 | CE2 | PHE | A | 21 | 4.593 | 56.183 | 13.086 | 1.00 | 18.61 | C |
| ATOM | 364 | CD2 | PHE | A | 21 | 3.738 | 55.711 | 12.078 | 1.00 | 19.14 | C |
| ATOM | 366 | C | PHE | A | 21 | 4.352 | 54.889 | 8.909 | 1.00 | 17.19 | C |
| ATOM | 367 | O | PHE | A | 21 | 5.582 | 54.794 | 8.984 | 1.00 | 17.08 | O |
| ATOM | 368 | N | ILE | A | 22 | 3.735 | 56.006 | 8.551 | 1.00 | 18.19 | N |
| ATOM | 370 | CA | ILE | A | 22 | 4.473 | 57.247 | 8.310 | 1.00 | 19.74 | C |
| ATOM | 372 | CB | ILE | A | 22 | 3.975 | 57.931 | 7.039 | 1.00 | 20.03 | C |
| ATOM | 374 | CG1 | ILE | A | 22 | 4.374 | 57.152 | 5.775 | 1.00 | 21.05 | C |
| ATOM | 377 | CD1 | ILE | A | 22 | 5.115 | 55.901 | 5.962 | 1.00 | 22.97 | C |
| ATOM | 381 | CG2 | ILE | A | 22 | 4.606 | 59.310 | 6.897 | 1.00 | 20.32 | C |
| ATOM | 385 | C | ILE | A | 22 | 4.289 | 58.164 | 9.527 | 1.00 | 20.68 | C |
| ATOM | 386 | O | ILE | A | 22 | 3.165 | 58.487 | 9.894 | 1.00 | 20.48 | O |
| ATOM | 387 | N | ASP | A | 23 | 5.374 | 58.570 | 10.174 | 1.00 | 21.90 | N |
| ATOM | 389 | CA | ASP | A | 23 | 5.210 | 59.413 | 11.345 | 1.00 | 23.59 | C |
| ATOM | 391 | CB | ASP | A | 23 | 6.371 | 59.282 | 12.290 | 1.00 | 23.31 | C |
| ATOM | 394 | CG | ASP | A | 23 | 7.588 | 60.112 | 11.860 | 1.00 | 23.99 | C |
| ATOM | 395 | OD1 | ASP | A | 23 | 7.524 | 60.875 | 10.853 | 1.00 | 20.95 | O |
| ATOM | 396 | OD2 | ASP | A | 23 | 8.660 | 60.019 | 12.484 | 1.00 | 22.12 | O |
| ATOM | 397 | C | ASP | A | 23 | 5.022 | 60.863 | 10.988 | 1.00 | 25.67 | C |
| ATOM | 398 | O | ASP | A | 23 | 4.902 | 61.241 | 9.819 | 1.00 | 25.35 | O |
| ATOM | 399 | N | GLN | A | 24 | 5.013 | 61.682 | 12.023 | 1.00 | 28.27 | N |
| ATOM | 401 | CA | GLN | A | 24 | 4.730 | 63.084 | 11.851 | 1.00 | 30.16 | C |
| ATOM | 403 | CB | GLN | A | 24 | 4.695 | 63.768 | 13.193 | 1.00 | 31.23 | C |

TABLE I-continued

The atomic coordinates of an altered human IL-18 structure; SEQ
ID No: 1 with a C38S substitution.
(P6$_1$)a = 71.4°, b = 71.4°, c = 88.7°, α,β = 90° and γ = 120°

| ATOM | 406 | CG | GLN | A | 24 | 3.617 | 64.750 | 13.185 | 1.00 | 34.46 | C |
|---|---|---|---|---|---|---|---|---|---|---|---|
| ATOM | 409 | CD | GLN | A | 24 | 2.313 | 64.046 | 13.001 | 1.00 | 38.96 | C |
| ATOM | 410 | OE1 | GLN | A | 24 | 2.017 | 63.133 | 13.772 | 1.00 | 43.16 | O |
| ATOM | 411 | NE2 | GLN | A | 24 | 1.537 | 64.425 | 11.978 | 1.00 | 40.28 | N |
| ATOM | 414 | C | GLN | A | 24 | 5.715 | 63.792 | 10.963 | 1.00 | 30.13 | C |
| ATOM | 415 | O | GLN | A | 24 | 5.349 | 64.732 | 10.259 | 1.00 | 31.25 | O |
| ATOM | 416 | N | GLY | A | 25 | 6.962 | 63.353 | 10.998 | 1.00 | 30.11 | N |
| ATOM | 418 | CA | GLY | A | 25 | 7.996 | 63.952 | 10.180 | 1.00 | 29.92 | C |
| ATOM | 421 | C | GLY | A | 25 | 8.146 | 63.264 | 8.843 | 1.00 | 29.87 | C |
| ATOM | 422 | O | GLY | A | 25 | 9.175 | 63.397 | 8.183 | 1.00 | 29.58 | O |
| ATOM | 423 | N | ASN | A | 26 | 7.118 | 62.522 | 8.442 | 1.00 | 29.58 | N |
| ATOM | 425 | CA | ASN | A | 26 | 7.136 | 61.802 | 7.178 | 1.00 | 29.55 | C |
| ATOM | 427 | CB | ASN | A | 26 | 7.384 | 62.756 | 6.012 | 1.00 | 30.28 | C |
| ATOM | 430 | CG | ASN | A | 26 | 6.170 | 63.575 | 5.684 | 1.00 | 33.62 | C |
| ATOM | 431 | OD1 | ASN | A | 26 | 5.067 | 63.042 | 5.573 | 1.00 | 37.65 | O |
| ATOM | 432 | ND2 | ASN | A | 26 | 6.357 | 64.886 | 5.532 | 1.00 | 38.42 | N |
| ATOM | 435 | C | ASN | A | 26 | 8.143 | 60.675 | 7.118 | 1.00 | 28.05 | C |
| ATOM | 436 | O | ASN | A | 26 | 8.494 | 60.248 | 6.033 | 1.00 | 28.17 | O |
| ATOM | 437 | N | ARG | A | 27 | 8.618 | 60.200 | 8.262 | 1.00 | 26.49 | N |
| ATOM | 439 | CA | ARG | A | 27 | 9.525 | 59.062 | 8.268 | 1.00 | 25.79 | C |
| ATOM | 441 | CB | ARG | A | 27 | 10.450 | 59.084 | 9.483 | 1.00 | 26.33 | C |
| ATOM | 444 | CG | ARG | A | 27 | 11.225 | 60.360 | 9.668 | 1.00 | 30.28 | C |
| ATOM | 447 | CD | ARG | A | 27 | 12.200 | 60.298 | 10.846 | 1.00 | 34.79 | C |
| ATOM | 450 | NE | ARG | A | 27 | 11.489 | 60.110 | 12.114 | 1.00 | 38.56 | N |
| ATOM | 452 | CZ | ARG | A | 27 | 12.070 | 59.977 | 13.308 | 1.00 | 40.76 | C |
| ATOM | 453 | NH1 | ARG | A | 27 | 13.398 | 59.987 | 13.428 | 1.00 | 41.30 | N |
| ATOM | 456 | NH2 | ARG | A | 27 | 11.307 | 59.835 | 14.388 | 1.00 | 41.91 | N |
| ATOM | 459 | C | ARG | A | 27 | 8.710 | 57.765 | 8.315 | 1.00 | 23.60 | C |
| ATOM | 460 | O | ARG | A | 27 | 7.772 | 57.651 | 9.103 | 1.00 | 22.10 | O |
| ATOM | 461 | N | PRO | A | 28 | 9.058 | 56.812 | 7.456 | 1.00 | 21.49 | N |
| ATOM | 462 | CA | PRO | A | 28 | 8.430 | 55.488 | 7.468 | 1.00 | 20.18 | C |
| ATOM | 464 | CB | PRO | A | 28 | 8.748 | 54.928 | 6.085 | 1.00 | 20.54 | C |
| ATOM | 467 | CG | PRO | A | 28 | 10.020 | 55.613 | 5.664 | 1.00 | 21.03 | C |
| ATOM | 470 | CD | PRO | A | 28 | 10.067 | 56.940 | 6.389 | 1.00 | 22.11 | C |
| ATOM | 473 | C | PRO | A | 28 | 9.069 | 54.647 | 8.556 | 1.00 | 18.85 | C |
| ATOM | 474 | O | PRO | A | 28 | 10.279 | 54.417 | 8.523 | 1.00 | 17.72 | O |
| ATOM | 475 | N | LEU | A | 29 | 8.258 | 54.232 | 9.522 | 1.00 | 17.18 | N |
| ATOM | 477 | CA | LEU | A | 29 | 8.709 | 53.458 | 10.666 | 1.00 | 16.68 | C |
| ATOM | 479 | CB | LEU | A | 29 | 8.681 | 54.327 | 11.923 | 1.00 | 16.73 | C |
| ATOM | 482 | CG | LEU | A | 29 | 9.498 | 55.626 | 11.931 | 1.00 | 18.13 | C |
| ATOM | 484 | CD1 | LEU | A | 29 | 9.300 | 56.348 | 13.249 | 1.00 | 19.44 | C |
| ATOM | 488 | CD2 | LEU | A | 29 | 10.967 | 55.328 | 11.726 | 1.00 | 20.09 | C |
| ATOM | 492 | C | LEU | A | 29 | 7.768 | 52.268 | 10.876 | 1.00 | 16.01 | C |
| ATOM | 493 | O | LEU | A | 29 | 6.731 | 52.174 | 10.233 | 1.00 | 15.65 | O |
| ATOM | 494 | N | PHE | A | 30 | 8.134 | 51.365 | 11.775 | 1.00 | 15.25 | N |
| ATOM | 496 | CA | PHE | A | 30 | 7.296 | 50.224 | 12.086 | 1.00 | 15.64 | C |
| ATOM | 498 | CB | PHE | A | 30 | 8.053 | 48.932 | 11.839 | 1.00 | 15.29 | C |
| ATOM | 501 | CG | PHE | A | 30 | 8.347 | 48.671 | 10.393 | 1.00 | 16.95 | C |
| ATOM | 502 | CD1 | PHE | A | 30 | 7.470 | 47.944 | 9.628 | 1.00 | 16.18 | C |
| ATOM | 504 | CE1 | PHE | A | 30 | 7.743 | 47.696 | 8.310 | 1.00 | 17.73 | C |
| ATOM | 506 | CZ | PHE | A | 30 | 8.916 | 48.173 | 7.741 | 1.00 | 15.84 | C |
| ATOM | 508 | CE2 | PHE | A | 30 | 9.786 | 48.907 | 8.498 | 1.00 | 17.01 | C |
| ATOM | 510 | CD2 | PHE | A | 30 | 9.506 | 49.158 | 9.803 | 1.00 | 17.48 | C |
| ATOM | 512 | C | PHE | A | 30 | 6.890 | 50.292 | 13.542 | 1.00 | 15.79 | C |
| ATOM | 513 | O | PHE | A | 30 | 7.754 | 50.559 | 14.411 | 1.00 | 15.41 | O |
| ATOM | 514 | N | GLU | A | 31 | 5.604 | 50.046 | 13.824 | 1.00 | 15.45 | N |
| ATOM | 516 | CA | GLU | A | 31 | 5.104 | 50.071 | 15.198 | 1.00 | 15.66 | C |
| ATOM | 518 | CB | GLU | A | 31 | 3.888 | 51.010 | 15.305 | 1.00 | 15.53 | C |
| ATOM | 521 | CG | GLU | A | 31 | 2.754 | 50.570 | 14.412 | 1.00 | 15.41 | C |
| ATOM | 524 | CD | GLU | A | 31 | 1.442 | 51.322 | 14.572 | 1.00 | 16.44 | C |
| ATOM | 525 | OE1 | GLU | A | 31 | 1.359 | 52.266 | 15.387 | 1.00 | 13.75 | O |
| ATOM | 526 | OE2 | GLU | A | 31 | 0.479 | 50.938 | 13.843 | 1.00 | 14.63 | O |
| ATOM | 527 | C | GLU | A | 31 | 4.678 | 48.693 | 15.726 | 1.00 | 15.83 | C |
| ATOM | 528 | O | GLU | A | 31 | 4.139 | 47.873 | 14.994 | 1.00 | 15.40 | O |
| ATOM | 529 | N | ASP | A | 32 | 4.941 | 48.435 | 16.999 | 1.00 | 16.09 | N |
| ATOM | 531 | CA | ASP | A | 32 | 4.344 | 47.287 | 17.662 | 1.00 | 17.04 | C |
| ATOM | 533 | CB | ASP | A | 32 | 5.025 | 47.017 | 18.992 | 1.00 | 17.47 | C |
| ATOM | 536 | CG | ASP | A | 32 | 6.428 | 46.518 | 18.810 | 1.00 | 19.12 | C |
| ATOM | 537 | OD1 | ASP | A | 32 | 6.606 | 45.401 | 18.291 | 1.00 | 21.41 | O |
| ATOM | 538 | OD2 | ASP | A | 32 | 7.406 | 47.198 | 19.108 | 1.00 | 25.01 | O |
| ATOM | 539 | C | ASP | A | 32 | 2.895 | 47.694 | 17.876 | 1.00 | 16.81 | C |
| ATOM | 540 | O | ASP | A | 32 | 2.629 | 48.861 | 18.102 | 1.00 | 16.58 | O |
| ATOM | 541 | N | MET | A | 33 | 1.954 | 46.762 | 17.800 | 1.00 | 17.50 | N |
| ATOM | 543 | CA | MET | A | 33 | 0.554 | 47.168 | 17.893 | 1.00 | 17.48 | C |
| ATOM | 545 | CB | MET | A | 33 | −0.393 | 46.143 | 17.275 | 1.00 | 18.16 | C |

TABLE I-continued

The atomic coordinates of an altered human IL-18 structure; SEQ ID No: 1 with a C38S substitution.
(P6₁)a = 71.4°, b = 71.4°, c = 88.7°, α,β = 90° and γ = 120°

| ATOM | 548 | CG | MET | A | 33 | −0.360 | 46.163 | 15.700 | 1.00 | 18.54 | C |
|------|-----|-----|------|---|----|--------|--------|--------|------|-------|---|
| ATOM | 551 | SD | MET | A | 33 | −0.191 | 47.820 | 14.901 | 1.00 | 18.88 | S |
| ATOM | 552 | CE | MET | A | 33 | −1.646 | 48.558 | 15.544 | 1.00 | 18.31 | C |
| ATOM | 556 | C | MET | A | 33 | 0.124 | 47.608 | 19.291 | 1.00 | 17.13 | C |
| ATOM | 557 | O | MET | A | 33 | −0.888 | 48.290 | 19.406 | 1.00 | 16.82 | O |
| ATOM | 558 | N | THR | A | 34 | 0.888 | 47.277 | 20.334 | 1.00 | 16.03 | N |
| ATOM | 560 | CA | THR | A | 34 | 0.594 | 47.843 | 21.661 | 1.00 | 16.95 | C |
| ATOM | 562 | CB | THR | A | 34 | 1.067 | 46.922 | 22.810 | 1.00 | 17.06 | C |
| ATOM | 564 | OG1 | THR | A | 34 | 2.437 | 46.535 | 22.601 | 1.00 | 17.60 | O |
| ATOM | 566 | CG2 | THR | A | 34 | 0.295 | 45.631 | 22.830 | 1.00 | 17.37 | C |
| ATOM | 570 | C | THR | A | 34 | 1.226 | 49.233 | 21.892 | 1.00 | 16.97 | C |
| ATOM | 571 | O | THR | A | 34 | 1.063 | 49.809 | 22.967 | 1.00 | 16.35 | O |
| ATOM | 572 | N | ASP | A | 35 | 1.959 | 49.764 | 20.913 | 1.00 | 17.24 | N |
| ATOM | 574 | CA | ASP | A | 35 | 2.607 | 51.077 | 21.085 | 1.00 | 17.24 | C |
| ATOM | 576 | CB | AASP | A | 35 | 3.396 | 51.495 | 19.826 | 0.65 | 18.25 | C |
| ATOM | 577 | CB | BASP | A | 35 | 3.292 | 51.498 | 19.791 | 0.35 | 17.62 | C |
| ATOM | 582 | CG | AASP | A | 35 | 4.768 | 50.803 | 19.725 | 0.65 | 19.33 | C |
| ATOM | 583 | CG | BASP | A | 35 | 4.269 | 52.628 | 19.991 | 0.35 | 16.99 | C |
| ATOM | 584 | OD1 | AASP | A | 35 | 5.171 | 50.175 | 20.724 | 0.65 | 21.32 | O |
| ATOM | 585 | OD1 | BASP | A | 35 | 3.849 | 53.771 | 20.278 | 0.35 | 17.45 | O |
| ATOM | 586 | OD2 | AASP | A | 35 | 5.517 | 50.829 | 18.704 | 0.65 | 18.98 | O |
| ATOM | 587 | OD2 | BASP | A | 35 | 5.489 | 52.452 | 19.877 | 0.35 | 18.50 | O |
| ATOM | 588 | C | ASP | A | 35 | 1.568 | 52.125 | 21.447 | 1.00 | 16.93 | C |
| ATOM | 589 | O | ASP | A | 35 | 0.458 | 52.119 | 20.920 | 1.00 | 15.87 | O |
| ATOM | 590 | N | SER | A | 36 | 1.916 | 53.014 | 22.368 | 1.00 | 16.95 | N |
| ATOM | 592 | CA | SER | A | 36 | 0.993 | 54.048 | 22.803 | 1.00 | 17.78 | C |
| ATOM | 594 | CB | SER | A | 36 | 1.609 | 54.870 | 23.941 | 1.00 | 18.53 | C |
| ATOM | 597 | OG | SER | A | 36 | 2.790 | 55.507 | 23.522 | 1.00 | 17.91 | O |
| ATOM | 599 | C | SER | A | 36 | 0.592 | 54.969 | 21.660 | 1.00 | 18.33 | C |
| ATOM | 600 | O | SER | A | 36 | −0.480 | 55.563 | 21.689 | 1.00 | 18.76 | O |
| ATOM | 601 | N | ASP | A | 37 | 1.430 | 55.078 | 20.638 | 1.00 | 18.42 | N |
| ATOM | 603 | CA | ASP | A | 37 | 1.096 | 55.940 | 19.497 | 1.00 | 18.89 | C |
| ATOM | 605 | CB | ASP | A | 37 | 2.360 | 56.489 | 18.847 | 1.00 | 19.65 | C |
| ATOM | 608 | CG | ASP | A | 37 | 3.039 | 57.516 | 19.707 | 1.00 | 22.76 | C |
| ATOM | 609 | OD1 | ASP | A | 37 | 4.262 | 57.695 | 19.544 | 1.00 | 27.47 | O |
| ATOM | 610 | OD2 | ASP | A | 37 | 2.422 | 58.204 | 20.552 | 1.00 | 26.72 | O |
| ATOM | 611 | C | ASP | A | 37 | 0.281 | 55.266 | 18.423 | 1.00 | 17.96 | C |
| ATOM | 612 | O | ASP | A | 37 | −0.019 | 55.885 | 17.402 | 1.00 | 17.62 | O |
| ATOM | 613 | N | SER | A | 38 | −0.086 | 54.008 | 18.648 | 1.00 | 17.23 | N |
| ATOM | 615 | CA | SER | A | 38 | −0.855 | 53.253 | 17.663 | 1.00 | 16.77 | C |
| ATOM | 617 | CB | SER | A | 38 | −1.110 | 51.809 | 18.147 | 1.00 | 16.61 | C |
| ATOM | 620 | OG | SER | A | 38 | −1.901 | 51.787 | 19.318 | 1.00 | 15.78 | O |
| ATOM | 622 | C | SER | A | 38 | −2.158 | 53.959 | 17.301 | 1.00 | 16.78 | C |
| ATOM | 623 | O | SER | A | 38 | −2.576 | 53.934 | 16.147 | 1.00 | 15.87 | O |
| ATOM | 624 | N | ARG | A | 39 | −2.785 | 54.616 | 18.275 | 1.00 | 17.65 | N |
| ATOM | 626 | CA | ARG | A | 39 | −4.044 | 55.326 | 18.024 | 1.00 | 18.06 | C |
| ATOM | 628 | CB | ARG | A | 39 | −4.640 | 55.883 | 19.328 | 1.00 | 18.14 | C |
| ATOM | 631 | CG | ARG | A | 39 | −6.006 | 56.571 | 19.182 | 1.00 | 18.93 | C |
| ATOM | 634 | CD | ARG | A | 39 | −6.551 | 57.235 | 20.488 | 1.00 | 19.91 | C |
| ATOM | 637 | NE | ARG | A | 39 | −6.722 | 56.293 | 21.606 | 1.00 | 18.54 | N |
| ATOM | 639 | CZ | ARG | A | 39 | −5.807 | 56.072 | 22.546 | 1.00 | 19.94 | C |
| ATOM | 640 | NH1 | ARG | A | 39 | −4.664 | 56.729 | 22.529 | 1.00 | 20.80 | N |
| ATOM | 643 | NH2 | ARG | A | 39 | −6.022 | 55.189 | 23.516 | 1.00 | 20.49 | N |
| ATOM | 646 | C | ARG | A | 39 | −3.819 | 56.465 | 17.038 | 1.00 | 18.21 | C |
| ATOM | 647 | O | ARG | A | 39 | −4.537 | 56.602 | 16.072 | 1.00 | 17.63 | O |
| ATOM | 648 | N | ASP | A | 40 | −2.822 | 57.288 | 17.317 | 1.00 | 19.30 | N |
| ATOM | 650 | CA | ASP | A | 40 | −2.525 | 58.434 | 16.480 | 1.00 | 20.14 | C |
| ATOM | 652 | CB | ASP | A | 40 | −1.552 | 59.372 | 17.182 | 1.00 | 21.06 | C |
| ATOM | 655 | CG | ASP | A | 40 | −2.177 | 60.106 | 18.356 | 1.00 | 24.15 | C |
| ATOM | 656 | OD1 | ASP | A | 40 | −3.412 | 60.293 | 18.387 | 1.00 | 28.34 | O |
| ATOM | 657 | OD2 | ASP | A | 40 | −1.484 | 60.523 | 19.302 | 1.00 | 29.23 | O |
| ATOM | 658 | C | ASP | A | 40 | −1.914 | 58.004 | 15.150 | 1.00 | 19.89 | C |
| ATOM | 659 | O | ASP | A | 40 | −2.141 | 58.647 | 14.152 | 1.00 | 20.00 | O |
| ATOM | 660 | N | ASN | A | 41 | −1.128 | 56.933 | 15.132 | 1.00 | 19.31 | N |
| ATOM | 662 | CA | ASN | A | 41 | −0.520 | 56.462 | 13.870 | 1.00 | 19.51 | C |
| ATOM | 664 | CB | ASN | A | 41 | 0.592 | 55.445 | 14.159 | 1.00 | 19.05 | C |
| ATOM | 667 | CG | ASN | A | 41 | 1.764 | 56.052 | 14.898 | 1.00 | 21.10 | C |
| ATOM | 668 | OD1 | ASN | A | 41 | 1.961 | 57.255 | 14.870 | 1.00 | 20.31 | O |
| ATOM | 669 | ND2 | ASN | A | 41 | 2.560 | 55.214 | 15.550 | 1.00 | 24.49 | N |
| ATOM | 672 | C | ASN | A | 41 | −1.505 | 55.855 | 12.864 | 1.00 | 19.21 | C |
| ATOM | 673 | O | ASN | A | 41 | −1.174 | 55.753 | 11.682 | 1.00 | 19.13 | O |
| ATOM | 674 | N | ALA | A | 42 | −2.695 | 55.457 | 13.319 | 1.00 | 19.36 | N |
| ATOM | 676 | CA | ALA | A | 42 | −3.618 | 54.653 | 12.509 | 1.00 | 19.44 | C |
| ATOM | 678 | CB | ALA | A | 42 | −4.903 | 54.387 | 13.256 | 1.00 | 19.48 | C |
| ATOM | 682 | C | ALA | A | 42 | −3.915 | 55.138 | 11.103 | 1.00 | 19.95 | C |

TABLE I-continued

The atomic coordinates of an altered human IL-18 structure; SEQ
ID No: 1 with a C38S substitution.
(P6₁)a = 71.4°, b = 71.4°, c = 88.7°, α,β = 90° and γ = 120°

| ATOM | 683 | O | ALA | A | 42 | −3.876 | 54.353 | 10.154 | 1.00 | 19.84 | O |
| --- | --- | --- | --- | --- | --- | --- | --- | --- | --- | --- | --- |
| ATOM | 684 | N | PRO | A | 43 | −4.203 | 56.417 | 10.955 | 1.00 | 20.71 | N |
| ATOM | 685 | CA | PRO | A | 43 | −4.505 | 56.971 | 9.637 | 1.00 | 21.20 | C |
| ATOM | 687 | CB | PRO | A | 43 | −4.759 | 58.460 | 9.927 | 1.00 | 21.84 | C |
| ATOM | 690 | CG | PRO | A | 43 | −5.037 | 58.543 | 11.381 | 1.00 | 22.39 | C |
| ATOM | 693 | CD | PRO | A | 43 | −4.254 | 57.436 | 12.019 | 1.00 | 21.04 | C |
| ATOM | 696 | C | PRO | A | 43 | −3.333 | 56.841 | 8.672 | 1.00 | 21.53 | C |
| ATOM | 697 | O | PRO | A | 43 | −3.550 | 56.857 | 7.469 | 1.00 | 22.82 | O |
| ATOM | 698 | N | ARG | A | 44 | −2.118 | 56.686 | 9.179 | 1.00 | 20.57 | N |
| ATOM | 700 | CA | ARG | A | 44 | −0.959 | 56.606 | 8.304 | 1.00 | 20.37 | C |
| ATOM | 702 | CB | ARG | A | 44 | 0.087 | 57.576 | 8.814 | 1.00 | 21.51 | C |
| ATOM | 705 | CG | ARG | A | 44 | −0.541 | 58.875 | 9.220 | 1.00 | 26.78 | C |
| ATOM | 708 | CD | ARG | A | 44 | −0.279 | 59.996 | 8.301 | 1.00 | 33.29 | C |
| ATOM | 711 | NE | ARG | A | 44 | 0.915 | 60.767 | 8.640 | 1.00 | 38.91 | N |
| ATOM | 713 | CZ | ARG | A | 44 | 1.625 | 60.674 | 9.768 | 1.00 | 43.23 | C |
| ATOM | 714 | NH1 | ARG | A | 44 | 1.303 | 59.841 | 10.755 | 1.00 | 44.56 | N |
| ATOM | 717 | NH2 | ARG | A | 44 | 2.695 | 61.448 | 9.914 | 1.00 | 46.10 | N |
| ATOM | 720 | C | ARG | A | 44 | −0.353 | 55.215 | 8.205 | 1.00 | 18.39 | C |
| ATOM | 721 | O | ARG | A | 44 | 0.863 | 55.074 | 7.974 | 1.00 | 16.70 | O |
| ATOM | 722 | N | THR | A | 45 | −1.190 | 54.197 | 8.389 | 1.00 | 17.18 | N |
| ATOM | 724 | CA | THR | A | 45 | −0.753 | 52.810 | 8.223 | 1.00 | 15.95 | C |
| ATOM | 726 | CB | THR | A | 45 | −1.224 | 51.926 | 9.383 | 1.00 | 15.81 | C |
| ATOM | 728 | OG1 | THR | A | 45 | −2.651 | 51.973 | 9.481 | 1.00 | 13.66 | O |
| ATOM | 730 | CG2 | THR | A | 45 | −0.714 | 52.419 | 10.721 | 1.00 | 15.45 | C |
| ATOM | 734 | C | THR | A | 45 | −1.324 | 52.214 | 6.943 | 1.00 | 16.30 | C |
| ATOM | 735 | O | THR | A | 45 | −1.043 | 51.068 | 6.625 | 1.00 | 15.65 | O |
| ATOM | 736 | N | ILE | A | 46 | −2.133 | 52.979 | 6.215 | 1.00 | 16.29 | N |
| ATOM | 738 | CA | ILE | A | 46 | −2.794 | 52.459 | 5.022 | 1.00 | 16.92 | C |
| ATOM | 740 | CB | ILE | A | 46 | −4.253 | 52.921 | 4.967 | 1.00 | 17.44 | C |
| ATOM | 742 | CG1 | ILE | A | 46 | −5.014 | 52.549 | 6.245 | 1.00 | 19.36 | C |
| ATOM | 745 | CD1 | ILE | A | 46 | −5.026 | 51.072 | 6.561 | 1.00 | 19.22 | C |
| ATOM | 749 | CG2 | ILE | A | 46 | −4.961 | 52.323 | 3.734 | 1.00 | 19.55 | C |
| ATOM | 753 | C | ILE | A | 46 | −2.057 | 52.941 | 3.778 | 1.00 | 16.31 | C |
| ATOM | 754 | O | ILE | A | 46 | −1.936 | 54.137 | 3.553 | 1.00 | 16.76 | O |
| ATOM | 755 | N | PHE | A | 47 | −1.542 | 52.008 | 2.987 | 1.00 | 15.89 | N |
| ATOM | 757 | CA | PHE | A | 47 | −0.780 | 52.356 | 1.806 | 1.00 | 15.36 | C |
| ATOM | 759 | CB | PHE | A | 47 | 0.605 | 51.716 | 1.847 | 1.00 | 15.78 | C |
| ATOM | 762 | CG | PHE | A | 47 | 1.456 | 52.253 | 2.948 | 1.00 | 15.47 | C |
| ATOM | 763 | CD1 | PHE | A | 47 | 1.353 | 51.733 | 4.223 | 1.00 | 15.36 | C |
| ATOM | 765 | CE1 | PHE | A | 47 | 2.082 | 52.258 | 5.268 | 1.00 | 15.99 | C |
| ATOM | 767 | CZ | PHE | A | 47 | 2.933 | 53.336 | 5.052 | 1.00 | 17.18 | C |
| ATOM | 769 | CE2 | PHE | A | 47 | 3.034 | 53.890 | 3.787 | 1.00 | 17.05 | C |
| ATOM | 771 | CD2 | PHE | A | 47 | 2.284 | 53.349 | 2.736 | 1.00 | 16.13 | C |
| ATOM | 773 | C | PHE | A | 47 | −1.512 | 51.974 | 0.554 | 1.00 | 15.47 | C |
| ATOM | 774 | O | PHE | A | 47 | −2.258 | 50.995 | 0.523 | 1.00 | 15.63 | O |
| ATOM | 775 | N | ILE | A | 48 | −1.328 | 52.799 | −0.471 | 1.00 | 14.27 | N |
| ATOM | 777 | CA | ILE | A | 48 | −1.888 | 52.544 | −1.758 | 1.00 | 14.07 | C |
| ATOM | 779 | CB | ILE | A | 48 | −2.283 | 53.858 | −2.449 | 1.00 | 14.65 | C |
| ATOM | 781 | CG1 | ILE | A | 48 | −3.246 | 54.684 | −1.591 | 1.00 | 16.00 | C |
| ATOM | 784 | CD1 | ILE | A | 48 | −3.418 | 56.115 | −2.067 | 1.00 | 17.30 | C |
| ATOM | 788 | CG2 | ILE | A | 48 | −2.936 | 53.550 | −3.782 | 1.00 | 14.34 | C |
| ATOM | 792 | C | ILE | A | 48 | −0.803 | 51.829 | −2.572 | 1.00 | 14.12 | C |
| ATOM | 793 | O | ILE | A | 48 | 0.228 | 52.414 | −2.907 | 1.00 | 14.11 | O |
| ATOM | 794 | N | ILE | A | 49 | −1.003 | 50.544 | −2.823 | 1.00 | 13.76 | N |
| ATOM | 796 | CA | ILE | A | 49 | −0.071 | 49.790 | −3.630 | 1.00 | 13.76 | C |
| ATOM | 798 | CB | ILE | A | 49 | 0.212 | 48.405 | −3.032 | 1.00 | 13.61 | C |
| ATOM | 800 | CG1 | ILE | A | 49 | 0.795 | 48.551 | −1.629 | 1.00 | 15.49 | C |
| ATOM | 803 | CD1 | ILE | A | 49 | 1.141 | 47.218 | −0.962 | 1.00 | 15.57 | C |
| ATOM | 807 | CG2 | ILE | A | 49 | 1.205 | 47.659 | −3.897 | 1.00 | 14.76 | C |
| ATOM | 811 | C | ILE | A | 49 | −0.676 | 49.689 | −5.023 | 1.00 | 13.36 | C |
| ATOM | 812 | O | ILE | A | 49 | −1.755 | 49.116 | −5.193 | 1.00 | 12.10 | O |
| ATOM | 813 | N | SER | A | 50 | 0.010 | 50.290 | −5.997 | 1.00 | 13.17 | N |
| ATOM | 815 | CA | SER | A | 50 | −0.438 | 50.256 | −7.379 | 1.00 | 13.46 | C |
| ATOM | 817 | CB | SER | A | 50 | −0.349 | 51.637 | −8.025 | 1.00 | 13.51 | C |
| ATOM | 820 | OG | SER | A | 50 | −1.083 | 52.599 | −7.278 | 1.00 | 12.74 | O |
| ATOM | 822 | C | SER | A | 50 | 0.401 | 49.255 | −8.159 | 1.00 | 14.11 | C |
| ATOM | 823 | O | SER | A | 50 | 1.622 | 49.267 | −8.079 | 1.00 | 14.03 | O |
| ATOM | 824 | N | MET | A | 51 | −0.282 | 48.374 | −8.883 | 1.00 | 14.13 | N |
| ATOM | 826 | CA | MET | A | 51 | 0.361 | 47.339 | −9.693 | 1.00 | 15.12 | C |
| ATOM | 828 | CB | BMET | A | 51 | −0.394 | 46.000 | −9.589 | 0.35 | 15.12 | C |
| ATOM | 829 | CB | AMET | A | 51 | −0.407 | 46.029 | −9.572 | 0.65 | 14.93 | C |
| ATOM | 834 | CG | BMET | A | 51 | −0.328 | 45.128 | −10.870 | 0.35 | 17.73 | C |
| ATOM | 835 | CG | AMET | A | 51 | −0.029 | 45.207 | −8.357 | 0.65 | 18.28 | C |
| ATOM | 840 | SD | BMET | A | 51 | −0.785 | 43.365 | −10.693 | 0.35 | 22.63 | S |
| ATOM | 841 | SD | AMET | A | 51 | −0.357 | 45.980 | −6.772 | 0.65 | 23.51 | S |

TABLE I-continued

The atomic coordinates of an altered human IL-18 structure; SEQ ID No: 1 with a C38S substitution.
(P6₁) a = 71.4°, b = 71.4°, c = 88.7°, α,β = 90° and γ = 120°

| ATOM | 842 | CE | BMET | A | 51 | −2.496 | 43.412 | −10.740 | 0.35 | 21.88 | C |
|---|---|---|---|---|---|---|---|---|---|---|---|
| ATOM | 843 | CE | AMET | A | 51 | −2.160 | 45.935 | −6.666 | 0.65 | 22.29 | C |
| ATOM | 850 | C | MET | A | 51 | 0.440 | 47.780 | −11.150 | 1.00 | 14.22 | C |
| ATOM | 851 | O | MET | A | 51 | −0.516 | 48.340 | −11.679 | 1.00 | 13.92 | O |
| ATOM | 852 | N | TYR | A | 52 | 1.568 | 47.499 | −11.782 | 1.00 | 13.17 | N |
| ATOM | 854 | CA | TYR | A | 52 | 1.818 | 47.908 | −13.159 | 1.00 | 13.42 | C |
| ATOM | 856 | CB | TYR | A | 52 | 2.991 | 48.887 | −13.227 | 1.00 | 13.08 | C |
| ATOM | 859 | CG | TYR | A | 52 | 2.700 | 50.250 | −12.644 | 1.00 | 13.49 | C |
| ATOM | 860 | CD1 | TYR | A | 52 | 2.618 | 50.434 | −11.278 | 1.00 | 13.31 | C |
| ATOM | 862 | CE1 | TYR | A | 52 | 2.336 | 51.673 | −10.734 | 1.00 | 11.89 | C |
| ATOM | 864 | CZ | TYR | A | 52 | 2.114 | 52.740 | −11.574 | 1.00 | 13.12 | C |
| ATOM | 865 | OH | TYR | A | 52 | 1.820 | 53.970 | −11.049 | 1.00 | 13.72 | O |
| ATOM | 867 | CE2 | TYR | A | 52 | 2.206 | 52.580 | −12.949 | 1.00 | 13.05 | C |
| ATOM | 869 | CD2 | TYR | A | 52 | 2.485 | 51.351 | −13.470 | 1.00 | 13.56 | C |
| ATOM | 871 | C | TYR | A | 52 | 2.138 | 46.726 | −14.073 | 1.00 | 13.83 | C |
| ATOM | 872 | O | TYR | A | 52 | 2.813 | 45.794 | −13.691 | 1.00 | 12.81 | O |
| ATOM | 873 | N | LYS | A | 53 | 1.606 | 46.775 | −15.284 | 1.00 | 14.14 | N |
| ATOM | 875 | CA | LYS | A | 53 | 2.012 | 45.888 | −16.327 | 1.00 | 14.63 | C |
| ATOM | 877 | CB | LYS | A | 53 | 1.015 | 45.980 | −17.481 | 1.00 | 15.35 | C |
| ATOM | 880 | CG | LYS | A | 53 | 1.249 | 45.010 | −18.641 | 1.00 | 17.12 | C |
| ATOM | 883 | CD | LYS | A | 53 | 0.183 | 45.252 | −19.745 | 1.00 | 20.65 | C |
| ATOM | 886 | CE | LYS | A | 53 | 0.117 | 44.118 | −20.741 | 1.00 | 23.88 | C |
| ATOM | 889 | NZ | LYS | A | 53 | −0.805 | 44.414 | −21.904 | 1.00 | 26.89 | N |
| ATOM | 893 | C | LYS | A | 53 | 3.370 | 46.409 | −16.802 | 1.00 | 14.60 | C |
| ATOM | 894 | O | LYS | A | 53 | 3.528 | 47.608 | −17.031 | 1.00 | 15.32 | O |
| ATOM | 895 | N | ASP | A | 54 | 4.327 | 45.505 | −16.987 | 1.00 | 13.67 | N |
| ATOM | 897 | CA | ASP | A | 54 | 5.660 | 45.844 | −17.389 | 1.00 | 13.60 | C |
| ATOM | 899 | CB | ASP | A | 54 | 6.586 | 45.322 | −16.301 | 1.00 | 13.42 | C |
| ATOM | 902 | CG | ASP | A | 54 | 8.012 | 45.758 | −16.450 | 1.00 | 13.39 | C |
| ATOM | 903 | OD1 | ASP | A | 54 | 8.430 | 46.291 | −17.496 | 1.00 | 11.84 | O |
| ATOM | 904 | OD2 | ASP | A | 54 | 8.810 | 45.564 | −15.494 | 1.00 | 12.26 | O |
| ATOM | 905 | C | ASP | A | 54 | 5.965 | 45.175 | −18.720 | 1.00 | 13.35 | C |
| ATOM | 906 | O | ASP | A | 54 | 5.737 | 43.979 | −18.883 | 1.00 | 12.28 | O |
| ATOM | 907 | N | SER | A | 55 | 6.488 | 45.946 | −19.663 | 1.00 | 13.06 | N |
| ATOM | 909 | CA | SER | A | 55 | 6.871 | 45.407 | −20.972 | 1.00 | 13.70 | C |
| ATOM | 911 | CB | SER | A | 55 | 7.161 | 46.546 | −21.957 | 1.00 | 13.57 | C |
| ATOM | 914 | OG | SER | A | 55 | 8.241 | 47.346 | −21.501 | 1.00 | 14.01 | O |
| ATOM | 916 | C | SER | A | 55 | 8.077 | 44.473 | −20.899 | 1.00 | 14.21 | C |
| ATOM | 917 | O | SER | A | 55 | 8.327 | 43.730 | −21.849 | 1.00 | 14.21 | O |
| ATOM | 918 | N | GLN | A | 56 | 8.811 | 44.520 | −19.774 | 1.00 | 14.99 | N |
| ATOM | 920 | CA | GLN | A | 56 | 9.955 | 43.652 | −19.499 | 1.00 | 15.58 | C |
| ATOM | 922 | CB | GLN | A | 56 | 11.228 | 44.475 | −19.426 | 1.00 | 16.60 | C |
| ATOM | 925 | CG | GLN | A | 56 | 12.032 | 44.503 | −20.712 | 1.00 | 21.81 | C |
| ATOM | 928 | CD | GLN | A | 56 | 13.223 | 45.462 | −20.632 | 1.00 | 25.90 | C |
| ATOM | 929 | OE1 | GLN | A | 56 | 13.952 | 45.472 | −19.632 | 1.00 | 29.00 | O |
| ATOM | 930 | NE2 | GLN | A | 56 | 13.385 | 46.295 | −21.660 | 1.00 | 27.25 | N |
| ATOM | 933 | C | GLN | A | 56 | 9.762 | 42.947 | −18.145 | 1.00 | 14.96 | C |
| ATOM | 934 | O | GLN | A | 56 | 10.292 | 43.378 | −17.100 | 1.00 | 13.21 | O |
| ATOM | 935 | N | PRO | A | 57 | 8.975 | 41.886 | −18.148 | 1.00 | 14.87 | N |
| ATOM | 936 | CA | PRO | A | 57 | 8.604 | 41.230 | −16.897 | 1.00 | 14.94 | C |
| ATOM | 938 | CB | PRO | A | 57 | 7.687 | 40.101 | −17.344 | 1.00 | 15.26 | C |
| ATOM | 941 | CG | PRO | A | 57 | 7.246 | 40.492 | −18.701 | 1.00 | 15.17 | C |
| ATOM | 944 | CD | PRO | A | 57 | 8.347 | 41.253 | −19.314 | 1.00 | 15.02 | C |
| ATOM | 947 | C | PRO | A | 57 | 9.791 | 40.716 | −16.104 | 1.00 | 14.55 | C |
| ATOM | 948 | O | PRO | A | 57 | 10.569 | 39.897 | −16.593 | 1.00 | 15.16 | O |
| ATOM | 949 | N | ARG | A | 58 | 9.916 | 41.208 | −14.886 | 1.00 | 14.38 | N |
| ATOM | 951 | CA | ARG | A | 58 | 11.049 | 40.887 | −13.989 | 1.00 | 14.78 | C |
| ATOM | 953 | CB | ARG | A | 58 | 11.992 | 42.094 | −13.898 | 1.00 | 14.70 | C |
| ATOM | 956 | CG | ARG | A | 58 | 12.872 | 42.266 | −15.132 | 1.00 | 15.88 | C |
| ATOM | 959 | CD | ARG | A | 58 | 13.405 | 43.701 | −15.364 | 1.00 | 16.69 | C |
| ATOM | 962 | NE | ARG | A | 58 | 12.345 | 44.611 | −15.778 | 1.00 | 16.02 | N |
| ATOM | 964 | CZ | ARG | A | 58 | 12.481 | 45.919 | −15.872 | 1.00 | 14.64 | C |
| ATOM | 965 | NH1 | ARG | A | 58 | 13.640 | 46.506 | −15.574 | 1.00 | 13.09 | N |
| ATOM | 968 | NH2 | ARG | A | 58 | 11.448 | 46.655 | −16.227 | 1.00 | 14.67 | N |
| ATOM | 971 | C | ARG | A | 58 | 10.583 | 40.491 | −12.584 | 1.00 | 15.27 | C |
| ATOM | 972 | O | ARG | A | 58 | 11.339 | 39.871 | −11.826 | 1.00 | 15.40 | O |
| ATOM | 973 | N | GLY | A | 59 | 9.337 | 40.849 | −12.260 | 1.00 | 15.27 | N |
| ATOM | 975 | CA | GLY | A | 59 | 8.726 | 40.598 | −10.967 | 1.00 | 15.75 | C |
| ATOM | 978 | C | GLY | A | 59 | 7.481 | 41.472 | −10.915 | 1.00 | 15.07 | C |
| ATOM | 979 | O | GLY | A | 59 | 7.238 | 42.193 | −11.866 | 1.00 | 16.33 | O |
| ATOM | 980 | N | MET | A | 60 | 6.676 | 41.430 | −9.860 | 1.00 | 14.19 | N |
| ATOM | 982 | CA | MET | A | 60 | 5.465 | 42.255 | −9.869 | 1.00 | 13.82 | C |
| ATOM | 984 | CB | MET | A | 60 | 4.438 | 41.778 | −8.854 | 1.00 | 14.80 | C |
| ATOM | 987 | CG | MET | A | 60 | 3.062 | 42.458 | −9.063 | 1.00 | 16.06 | C |
| ATOM | 990 | SD | MET | A | 60 | 1.705 | 41.789 | −8.055 | 1.00 | 22.71 | S |

TABLE I-continued

The atomic coordinates of an altered human IL-18 structure; SEQ
ID No: 1 with a C38S substitution.
(P6$_1$)a = 71.4°, b = 71.4°, c = 88.7°, α,β = 90° and γ = 120°

| ATOM | 991 | CE | MET | A | 60 | 2.266 | 42.118 | −6.460 | 1.00 | 21.67 | C |
|---|---|---|---|---|---|---|---|---|---|---|---|
| ATOM | 995 | C | MET | A | 60 | 5.800 | 43.733 | −9.628 | 1.00 | 13.15 | C |
| ATOM | 996 | O | MET | A | 60 | 6.228 | 44.119 | −8.540 | 1.00 | 11.40 | O |
| ATOM | 997 | N | ALA | A | 61 | 5.611 | 44.550 | −10.657 | 1.00 | 12.27 | N |
| ATOM | 999 | CA | ALA | A | 61 | 5.946 | 45.978 | −10.568 | 1.00 | 12.12 | C |
| ATOM | 1001 | CB | ALA | A | 61 | 6.105 | 46.548 | −11.936 | 1.00 | 12.34 | C |
| ATOM | 1005 | C | ALA | A | 61 | 4.912 | 46.759 | −9.786 | 1.00 | 11.69 | C |
| ATOM | 1006 | O | ALA | A | 61 | 3.730 | 46.743 | −10.119 | 1.00 | 12.80 | O |
| ATOM | 1007 | N | VAL | A | 62 | 5.355 | 47.442 | −8.743 | 1.00 | 11.59 | N |
| ATOM | 1009 | CA | VAL | A | 62 | 4.457 | 48.216 | −7.909 | 1.00 | 10.97 | C |
| ATOM | 1011 | CB | VAL | A | 62 | 4.101 | 47.489 | −6.601 | 1.00 | 10.99 | C |
| ATOM | 1013 | CG1 | VAL | A | 62 | 3.420 | 46.138 | −6.868 | 1.00 | 11.40 | C |
| ATOM | 1017 | CG2 | VAL | A | 62 | 5.345 | 47.293 | −5.711 | 1.00 | 11.11 | C |
| ATOM | 1021 | C | VAL | A | 62 | 5.045 | 49.527 | −7.480 | 1.00 | 11.09 | C |
| ATOM | 1022 | O | VAL | A | 62 | 6.253 | 49.684 | −7.435 | 1.00 | 10.73 | O |
| ATOM | 1023 | N | THR | A | 63 | 4.156 | 50.473 | −7.177 | 1.00 | 11.51 | N |
| ATOM | 1025 | CA | THR | A | 63 | 4.528 | 51.692 | −6.489 | 1.00 | 11.73 | C |
| ATOM | 1027 | CB | THR | A | 63 | 4.070 | 52.961 | −7.236 | 1.00 | 12.36 | C |
| ATOM | 1029 | OG1 | THR | A | 63 | 2.651 | 52.917 | −7.436 | 1.00 | 10.48 | O |
| ATOM | 1031 | CG2 | THR | A | 63 | 4.673 | 53.040 | −8.603 | 1.00 | 11.83 | C |
| ATOM | 1035 | C | THR | A | 63 | 3.792 | 51.642 | −5.152 | 1.00 | 12.38 | C |
| ATOM | 1036 | O | THR | A | 63 | 2.739 | 51.010 | −5.034 | 1.00 | 12.60 | O |
| ATOM | 1037 | N | ILE | A | 64 | 4.345 | 52.328 | −4.167 | 1.00 | 12.32 | N |
| ATOM | 1039 | CA | ILE | A | 64 | 3.781 | 52.380 | −2.843 | 1.00 | 13.31 | C |
| ATOM | 1041 | CB | ILE | A | 64 | 4.742 | 51.754 | −1.844 | 1.00 | 13.48 | C |
| ATOM | 1043 | CG1 | ILE | A | 64 | 4.912 | 50.271 | −2.133 | 1.00 | 14.30 | C |
| ATOM | 1046 | CD1 | ILE | A | 64 | 6.089 | 49.643 | −1.370 | 1.00 | 15.77 | C |
| ATOM | 1050 | CG2 | ILE | A | 64 | 4.223 | 51.942 | −0.437 | 1.00 | 15.38 | C |
| ATOM | 1054 | C | ILE | A | 64 | 3.557 | 53.836 | −2.498 | 1.00 | 13.39 | C |
| ATOM | 1055 | O | ILE | A | 64 | 4.521 | 54.617 | −2.404 | 1.00 | 13.39 | O |
| ATOM | 1056 | N | SER | A | 65 | 2.295 | 54.188 | −2.290 | 1.00 | 14.03 | N |
| ATOM | 1058 | CA | SER | A | 65 | 1.895 | 55.560 | −1.996 | 1.00 | 15.17 | C |
| ATOM | 1060 | CB | SER | A | 65 | 1.114 | 56.167 | −3.180 | 1.00 | 14.68 | C |
| ATOM | 1063 | OG | SER | A | 65 | 1.783 | 55.984 | −4.419 | 1.00 | 13.32 | O |
| ATOM | 1065 | C | SER | A | 65 | 1.061 | 55.674 | −0.704 | 1.00 | 17.01 | C |
| ATOM | 1066 | O | SER | A | 65 | 0.544 | 54.663 | −0.129 | 1.00 | 15.87 | O |
| ATOM | 1067 | N | VAL | A | 66 | 0.979 | 56.923 | −0.241 | 1.00 | 19.37 | N |
| ATOM | 1069 | CA | VAL | A | 66 | 0.260 | 57.284 | 0.981 | 1.00 | 22.27 | C |
| ATOM | 1071 | CB | VAL | A | 66 | 1.175 | 57.628 | 2.159 | 1.00 | 22.39 | C |
| ATOM | 1073 | CG1 | AVAL | A | 66 | 1.651 | 56.424 | 2.895 | 0.50 | 22.78 | C |
| ATOM | 1074 | CG1 | BVAL | A | 66 | 0.554 | 56.963 | 3.366 | 0.50 | 22.35 | C |
| ATOM | 1081 | CG2 | AVAL | A | 66 | 2.427 | 58.300 | 1.646 | 0.50 | 22.51 | C |
| ATOM | 1082 | CG2 | BVAL | A | 66 | 2.559 | 57.082 | 1.990 | 0.50 | 23.29 | C |
| ATOM | 1089 | C | VAL | A | 66 | −0.520 | 58.555 | 0.802 | 1.00 | 24.38 | C |
| ATOM | 1090 | O | VAL | A | 66 | −0.009 | 59.513 | 0.227 | 1.00 | 24.82 | O |
| ATOM | 1091 | N | LYS | A | 67 | −1.739 | 58.547 | 1.310 | 1.00 | 27.09 | N |
| ATOM | 1093 | CA | LYS | A | 67 | −2.602 | 59.711 | 1.263 | 1.00 | 29.97 | C |
| ATOM | 1095 | CB | LYS | A | 67 | −4.034 | 59.347 | 0.890 | 1.00 | 30.64 | C |
| ATOM | 1098 | CG | LYS | A | 67 | −4.957 | 60.580 | 0.889 | 1.00 | 32.37 | C |
| ATOM | 1101 | CD | LYS | A | 67 | −6.037 | 60.470 | −0.187 | 1.00 | 34.82 | C |
| ATOM | 1104 | CE | LYS | A | 67 | −6.613 | 61.848 | −0.555 | 1.00 | 36.52 | C |
| ATOM | 1107 | NZ | LYS | A | 67 | −7.719 | 61.705 | −1.551 | 1.00 | 38.38 | N |
| ATOM | 1111 | C | LYS | A | 67 | −2.642 | 60.443 | 2.591 | 1.00 | 31.87 | C |
| ATOM | 1112 | O | LYS | A | 67 | −3.165 | 59.931 | 3.580 | 1.00 | 31.42 | O |
| ATOM | 1113 | N | CYS | A | 68 | −2.049 | 61.630 | 2.609 | 1.00 | 34.05 | N |
| ATOM | 1115 | CA | CYS | A | 68 | −2.145 | 62.515 | 3.757 | 1.00 | 35.95 | C |
| ATOM | 1117 | CB | CYS | A | 68 | −0.777 | 63.070 | 4.139 | 1.00 | 36.35 | C |
| ATOM | 1120 | SG | CYS | A | 68 | 0.401 | 61.820 | 4.732 | 1.00 | 42.65 | S |
| ATOM | 1121 | C | CYS | A | 68 | −3.095 | 63.597 | 3.257 | 1.00 | 35.69 | C |
| ATOM | 1122 | O | CYS | A | 68 | −4.222 | 63.307 | 2.849 | 1.00 | 36.11 | O |
| ATOM | 1123 | N | GLU | A | 69 | −2.651 | 64.840 | 3.246 | 1.00 | 35.99 | N |
| ATOM | 1125 | CA | GLU | A | 69 | −3.469 | 65.883 | 2.655 | 1.00 | 35.80 | C |
| ATOM | 1127 | CB | GLU | A | 69 | −2.783 | 67.240 | 2.774 | 1.00 | 36.43 | C |
| ATOM | 1130 | CG | GLU | A | 69 | −3.624 | 68.392 | 2.242 | 1.00 | 37.99 | C |
| ATOM | 1133 | CD | GLU | A | 69 | −2.977 | 69.746 | 2.479 | 0.50 | 39.45 | C |
| ATOM | 1134 | OE1 | GLU | A | 69 | −3.573 | 70.763 | 2.067 | 0.50 | 40.45 | O |
| ATOM | 1135 | OE2 | GLU | A | 69 | −1.878 | 69.794 | 3.076 | 0.50 | 41.24 | O |
| ATOM | 1136 | C | GLU | A | 69 | −3.583 | 65.494 | 1.197 | 1.00 | 34.78 | C |
| ATOM | 1137 | O | GLU | A | 69 | −4.668 | 65.399 | 0.630 | 1.00 | 35.20 | O |
| ATOM | 1138 | N | LYS | A | 70 | −2.425 | 65.248 | 0.603 | 1.00 | 33.25 | N |
| ATOM | 1140 | CA | LYS | A | 70 | −2.327 | 64.860 | −0.795 | 1.00 | 31.85 | C |
| ATOM | 1142 | CB | LYS | A | 70 | −1.452 | 65.863 | −1.542 | 1.00 | 32.57 | C |
| ATOM | 1145 | CG | LYS | A | 70 | −1.667 | 67.317 | −1.129 | 1.00 | 35.54 | C |
| ATOM | 1148 | CD | LYS | A | 70 | −2.766 | 67.951 | −1.952 | 1.00 | 39.46 | C |
| ATOM | 1151 | CE | LYS | A | 70 | −2.263 | 68.396 | −3.324 | 1.00 | 41.73 | C |

TABLE I-continued

The atomic coordinates of an altered human IL-18 structure; SEQ
ID No: 1 with a C38S substitution.
(P6₁)a = 71.4°, b = 71.4°, c = 88.7°, α,β = 90° and γ = 120°

| ATOM | 1154 | NZ | LYS | A | 70 | −1.410 | 69.623 | −3.249 | 1.00 | 44.57 | N |
|---|---|---|---|---|---|---|---|---|---|---|---|
| ATOM | 1158 | C | LYS | A | 70 | −1.642 | 63.499 | −0.844 | 1.00 | 29.20 | C |
| ATOM | 1159 | O | LYS | A | 70 | −1.165 | 63.017 | 0.169 | 1.00 | 28.17 | O |
| ATOM | 1160 | N | ILE | A | 71 | −1.562 | 62.912 | −2.032 | 1.00 | 26.34 | N |
| ATOM | 1162 | CA | ILE | A | 71 | −0.890 | 61.626 | −2.197 | 1.00 | 24.51 | C |
| ATOM | 1164 | CB | ILE | A | 71 | −1.541 | 60.822 | −3.321 | 1.00 | 24.58 | C |
| ATOM | 1166 | CG1 | ILE | A | 71 | −2.990 | 60.475 | −2.937 | 1.00 | 25.08 | C |
| ATOM | 1169 | CD1 | ILE | A | 71 | −3.836 | 59.945 | −4.074 | 1.00 | 25.58 | C |
| ATOM | 1173 | CG2 | ILE | A | 71 | −0.731 | 59.562 | −3.608 | 1.00 | 24.28 | C |
| ATOM | 1177 | C | ILE | A | 71 | 0.586 | 61.808 | −2.496 | 1.00 | 23.04 | C |
| ATOM | 1178 | O | ILE | A | 71 | 0.980 | 62.620 | −3.354 | 1.00 | 21.98 | O |
| ATOM | 1179 | N | SER | A | 72 | 1.400 | 61.060 | −1.770 | 1.00 | 20.97 | N |
| ATOM | 1181 | CA | SER | A | 72 | 2.820 | 61.012 | −2.013 | 1.00 | 20.47 | C |
| ATOM | 1183 | CB | ASER | A | 72 | 3.558 | 61.588 | −0.814 | 0.50 | 20.49 | C |
| ATOM | 1184 | CB | BSER | A | 72 | 3.581 | 61.584 | −0.825 | 0.50 | 20.51 | C |
| ATOM | 1189 | OG | ASER | A | 72 | 3.373 | 62.994 | −0.777 | 0.50 | 22.61 | O |
| ATOM | 1190 | OG | BSER | A | 72 | 3.756 | 62.980 | −0.997 | 0.50 | 22.76 | O |
| ATOM | 1193 | C | SER | A | 72 | 3.265 | 59.578 | −2.293 | 1.00 | 18.71 | C |
| ATOM | 1194 | O | SER | A | 72 | 2.617 | 58.625 | −1.872 | 1.00 | 18.18 | O |
| ATOM | 1195 | N | THR | A | 73 | 4.370 | 59.433 | −3.007 | 1.00 | 17.03 | N |
| ATOM | 1197 | CA | THR | A | 73 | 4.832 | 58.125 | −3.427 | 1.00 | 16.16 | C |
| ATOM | 1199 | CB | THR | A | 73 | 4.716 | 58.017 | −4.951 | 1.00 | 15.82 | C |
| ATOM | 1201 | OG1 | THR | A | 73 | 3.331 | 58.095 | −5.342 | 1.00 | 13.69 | O |
| ATOM | 1203 | CG2 | THR | A | 73 | 5.210 | 56.665 | −5.449 | 1.00 | 15.20 | C |
| ATOM | 1207 | C | THR | A | 73 | 6.259 | 57.847 | −3.005 | 1.00 | 16.42 | C |
| ATOM | 1208 | O | THR | A | 73 | 7.169 | 58.685 | −3.169 | 1.00 | 15.32 | O |
| ATOM | 1209 | N | LEU | A | 74 | 6.458 | 56.641 | −2.488 | 1.00 | 16.48 | N |
| ATOM | 1211 | CA | LEU | A | 74 | 7.755 | 56.208 | −2.023 | 1.00 | 16.72 | C |
| ATOM | 1213 | CB | LEU | A | 74 | 7.613 | 54.842 | −1.399 | 1.00 | 17.31 | C |
| ATOM | 1216 | CG | LEU | A | 74 | 8.845 | 54.309 | −0.712 | 1.00 | 19.67 | C |
| ATOM | 1218 | CD1 | LEU | A | 74 | 8.986 | 55.021 | 0.604 | 1.00 | 22.08 | C |
| ATOM | 1222 | CD2 | LEU | A | 74 | 8.677 | 52.824 | −0.507 | 1.00 | 23.17 | C |
| ATOM | 1226 | C | LEU | A | 74 | 8.757 | 56.146 | −3.155 | 1.00 | 16.59 | C |
| ATOM | 1227 | O | LEU | A | 74 | 8.453 | 55.638 | −4.230 | 1.00 | 15.98 | O |
| ATOM | 1228 | N | SER | A | 75 | 9.965 | 56.626 | −2.883 | 1.00 | 16.71 | N |
| ATOM | 1230 | CA | SER | A | 75 | 11.020 | 56.701 | −3.864 | 1.00 | 17.09 | C |
| ATOM | 1232 | CB | SER | A | 75 | 11.152 | 58.152 | −4.359 | 1.00 | 17.22 | C |
| ATOM | 1235 | OG | SER | A | 75 | 12.363 | 58.340 | −5.075 | 1.00 | 15.74 | O |
| ATOM | 1237 | C | SER | A | 75 | 12.354 | 56.275 | −3.290 | 1.00 | 18.53 | C |
| ATOM | 1238 | O | SER | A | 75 | 12.638 | 56.491 | −2.105 | 1.00 | 19.00 | O |
| ATOM | 1239 | N | CYS | A | 76 | 13.196 | 55.665 | −4.100 | 1.00 | 19.50 | N |
| ATOM | 1241 | CA | CYS | A | 76 | 14.527 | 55.369 | −3.594 | 1.00 | 21.42 | C |
| ATOM | 1243 | CB | CYS | A | 76 | 14.787 | 53.892 | −3.555 | 1.00 | 21.92 | C |
| ATOM | 1246 | SG | CYS | A | 76 | 14.533 | 53.116 | −5.113 | 1.00 | 26.94 | S |
| ATOM | 1247 | C | CYS | A | 76 | 15.631 | 56.111 | −4.349 | 1.00 | 21.61 | C |
| ATOM | 1248 | O | CYS | A | 76 | 16.777 | 55.678 | −4.398 | 1.00 | 21.33 | O |
| ATOM | 1249 | N | GLU | A | 77 | 15.280 | 57.257 | −4.910 | 1.00 | 22.66 | N |
| ATOM | 1251 | CA | GLU | A | 77 | 16.255 | 58.060 | −5.618 | 1.00 | 23.70 | C |
| ATOM | 1253 | CB | GLU | A | 77 | 15.678 | 59.418 | −5.978 | 1.00 | 24.40 | C |
| ATOM | 1256 | CG | GLU | A | 77 | 16.667 | 60.248 | −6.796 | 1.00 | 27.41 | C |
| ATOM | 1259 | CD | GLU | A | 77 | 16.161 | 61.617 | −7.190 | 1.00 | 30.89 | C |
| ATOM | 1260 | OE1 | GLU | A | 77 | 16.844 | 62.266 | −8.022 | 1.00 | 35.70 | O |
| ATOM | 1261 | OE2 | GLU | A | 77 | 15.105 | 62.051 | −6.689 | 1.00 | 33.74 | O |
| ATOM | 1262 | C | GLU | A | 77 | 17.498 | 58.261 | −4.752 | 1.00 | 23.98 | C |
| ATOM | 1263 | O | GLU | A | 77 | 17.391 | 58.482 | −3.542 | 1.00 | 22.55 | O |
| ATOM | 1264 | N | ASN | A | 78 | 18.666 | 58.162 | −5.386 | 1.00 | 24.68 | N |
| ATOM | 1266 | CA | ASN | A | 78 | 19.950 | 58.344 | −4.722 | 1.00 | 25.56 | C |
| ATOM | 1268 | CB | ASN | A | 78 | 20.070 | 59.764 | −4.153 | 1.00 | 26.17 | C |
| ATOM | 1271 | CG | ASN | A | 78 | 20.049 | 60.832 | −5.243 | 1.00 | 28.42 | C |
| ATOM | 1272 | OD1 | ASN | A | 78 | 19.688 | 61.980 | −4.992 | 1.00 | 33.38 | O |
| ATOM | 1273 | ND2 | ASN | A | 78 | 20.418 | 60.450 | −6.460 | 1.00 | 30.26 | N |
| ATOM | 1276 | C | ASN | A | 78 | 20.165 | 57.304 | −3.637 | 1.00 | 25.79 | C |
| ATOM | 1277 | O | ASN | A | 78 | 20.868 | 57.549 | −2.664 | 1.00 | 25.20 | O |
| ATOM | 1278 | N | LYS | A | 79 | 19.549 | 56.139 | −3.832 | 1.00 | 26.08 | N |
| ATOM | 1280 | CA | LYS | A | 79 | 19.638 | 55.018 | −2.915 | 1.00 | 26.95 | C |
| ATOM | 1282 | CB | LYS | A | 79 | 21.065 | 54.437 | −2.891 | 1.00 | 27.51 | C |
| ATOM | 1285 | CG | LYS | A | 79 | 21.557 | 53.889 | −4.238 | 1.00 | 29.89 | C |
| ATOM | 1288 | CD | LYS | A | 79 | 22.986 | 53.341 | −4.137 | 1.00 | 32.67 | C |
| ATOM | 1291 | CE | LYS | A | 79 | 23.482 | 52.764 | −5.455 | 1.00 | 34.42 | C |
| ATOM | 1294 | NZ | LYS | A | 79 | 24.788 | 52.032 | −5.321 | 1.00 | 35.62 | N |
| ATOM | 1298 | C | LYS | A | 79 | 19.184 | 55.368 | −1.500 | 1.00 | 26.68 | C |
| ATOM | 1299 | O | LYS | A | 79 | 19.651 | 54.793 | −0.554 | 1.00 | 26.91 | O |
| ATOM | 1300 | N | ILE | A | 80 | 18.279 | 56.313 | −1.359 | 1.00 | 27.19 | N |
| ATOM | 1302 | CA | ILE | A | 80 | 17.770 | 56.677 | −0.052 | 1.00 | 28.15 | C |
| ATOM | 1304 | CB | ILE | A | 80 | 18.224 | 58.089 | 0.330 | 1.00 | 28.96 | C |

TABLE I-continued

The atomic coordinates of an altered human IL-18 structure; SEQ ID No: 1 with a C38S substitution.
(P6₁) a = 71.4°, b = 71.4°, c = 88.7°, α,β = 90° and γ = 120°

| ATOM | 1306 | CG1 | ILE | A | 80 | 17.751 | 58.436 | 1.720 | 1.00 | 31.62 | C |
|---|---|---|---|---|---|---|---|---|---|---|---|
| ATOM | 1309 | CD1 | ILE | A | 80 | 18.388 | 59.696 | 2.208 | 1.00 | 34.47 | C |
| ATOM | 1313 | CG2 | ILE | A | 80 | 17.599 | 59.113 | −0.542 | 1.00 | 30.48 | C |
| ATOM | 1317 | C | ILE | A | 80 | 16.262 | 56.661 | −0.118 | 1.00 | 27.36 | C |
| ATOM | 1318 | O | ILE | A | 80 | 15.698 | 56.961 | −1.164 | 1.00 | 26.85 | O |
| ATOM | 1319 | N | ILE | A | 81 | 15.619 | 56.316 | 0.987 | 1.00 | 26.61 | N |
| ATOM | 1321 | CA | ILE | A | 81 | 14.167 | 56.358 | 1.044 | 1.00 | 26.49 | C |
| ATOM | 1323 | CB | ILE | A | 81 | 13.660 | 55.473 | 2.187 | 1.00 | 26.75 | C |
| ATOM | 1325 | CG1 | ILE | A | 81 | 14.009 | 54.011 | 1.927 | 1.00 | 27.58 | C |
| ATOM | 1328 | CD1 | ILE | A | 81 | 13.408 | 53.480 | 0.678 | 1.00 | 29.35 | C |
| ATOM | 1332 | CG2 | ILE | A | 81 | 12.164 | 55.638 | 2.330 | 1.00 | 27.41 | C |
| ATOM | 1336 | C | ILE | A | 81 | 13.612 | 57.751 | 1.278 | 1.00 | 25.97 | C |
| ATOM | 1337 | O | ILE | A | 81 | 14.008 | 58.440 | 2.208 | 1.00 | 25.07 | O |
| ATOM | 1338 | N | SER | A | 82 | 12.645 | 58.151 | 0.461 | 1.00 | 25.49 | N |
| ATOM | 1340 | CA | SER | A | 82 | 11.967 | 59.416 | 0.654 | 1.00 | 25.49 | C |
| ATOM | 1342 | CB | SER | A | 82 | 12.760 | 60.528 | −0.033 | 1.00 | 25.97 | C |
| ATOM | 1345 | OG | SER | A | 82 | 12.788 | 60.309 | −1.451 | 1.00 | 25.78 | O |
| ATOM | 1347 | C | SER | A | 82 | 10.599 | 59.314 | −0.004 | 1.00 | 25.52 | C |
| ATOM | 1348 | O | SER | A | 82 | 10.288 | 58.304 | −0.646 | 1.00 | 24.44 | O |
| ATOM | 1349 | N | PHE | A | 83 | 9.784 | 60.348 | 0.155 | 1.00 | 25.53 | N |
| ATOM | 1351 | CA | PHE | A | 83 | 8.516 | 60.407 | −0.543 | 1.00 | 26.14 | C |
| ATOM | 1353 | CB | PHE | A | 83 | 7.396 | 60.678 | 0.420 | 1.00 | 26.66 | C |
| ATOM | 1356 | CG | PHE | A | 83 | 6.986 | 59.472 | 1.166 | 1.00 | 27.86 | C |
| ATOM | 1357 | CD1 | PHE | A | 83 | 7.569 | 59.171 | 2.380 | 1.00 | 30.53 | C |
| ATOM | 1359 | CE1 | PHE | A | 83 | 7.213 | 58.035 | 3.058 | 1.00 | 30.18 | C |
| ATOM | 1361 | CZ | PHE | A | 83 | 6.281 | 57.192 | 2.521 | 1.00 | 30.58 | C |
| ATOM | 1363 | CE2 | PHE | A | 83 | 5.704 | 57.485 | 1.309 | 1.00 | 29.81 | C |
| ATOM | 1365 | CD2 | PHE | A | 83 | 6.058 | 58.604 | 0.638 | 1.00 | 29.19 | C |
| ATOM | 1367 | C | PHE | A | 83 | 8.507 | 61.464 | −1.625 | 1.00 | 26.10 | C |
| ATOM | 1368 | O | PHE | A | 83 | 8.831 | 62.619 | −1.376 | 1.00 | 27.01 | O |
| ATOM | 1369 | N | LYS | A | 84 | 8.171 | 61.060 | −2.839 | 1.00 | 25.29 | N |
| ATOM | 1371 | CA | LYS | A | 84 | 8.028 | 62.003 | −3.936 | 1.00 | 25.20 | C |
| ATOM | 1373 | CB | LYS | A | 84 | 8.220 | 61.299 | −5.281 | 1.00 | 25.91 | C |
| ATOM | 1376 | CG | LYS | A | 84 | 9.461 | 61.685 | −6.053 | 1.00 | 28.54 | C |
| ATOM | 1379 | CD | LYS | A | 84 | 9.249 | 61.534 | −7.571 | 1.00 | 31.41 | C |
| ATOM | 1382 | CE | LYS | A | 84 | 10.361 | 62.265 | −8.363 | 1.00 | 34.15 | C |
| ATOM | 1385 | NZ | LYS | A | 84 | 10.094 | 62.387 | −9.800 | 1.00 | 32.15 | N |
| ATOM | 1389 | C | LYS | A | 84 | 6.618 | 62.578 | −3.836 | 1.00 | 24.05 | C |
| ATOM | 1390 | O | LYS | A | 84 | 5.665 | 61.836 | −3.581 | 1.00 | 22.96 | O |
| ATOM | 1391 | N | GLU | A | 85 | 6.481 | 63.884 | −4.051 | 1.00 | 23.01 | N |
| ATOM | 1393 | CA | GLU | A | 85 | 5.185 | 64.550 | −3.981 | 1.00 | 22.72 | C |
| ATOM | 1395 | CB | GLU | A | 85 | 5.354 | 66.047 | −3.705 | 1.00 | 23.58 | C |
| ATOM | 1398 | CG | GLU | A | 85 | 6.046 | 66.346 | −2.389 | 1.00 | 27.04 | C |
| ATOM | 1401 | CD | GLU | A | 85 | 5.170 | 66.090 | −1.183 | 1.00 | 31.68 | C |
| ATOM | 1402 | OE1 | GLU | A | 85 | 5.730 | 65.709 | −0.132 | 1.00 | 38.63 | O |
| ATOM | 1403 | OE2 | GLU | A | 85 | 3.929 | 66.263 | −1.262 | 1.00 | 35.20 | O |
| ATOM | 1404 | C | GLU | A | 85 | 4.430 | 64.344 | −5.281 | 1.00 | 21.30 | C |
| ATOM | 1405 | O | GLU | A | 85 | 4.342 | 65.241 | −6.122 | 1.00 | 20.65 | O |
| ATOM | 1406 | N | MET | A | 86 | 3.888 | 63.148 | −5.447 | 1.00 | 19.77 | N |
| ATOM | 1408 | CA | MET | A | 86 | 3.207 | 62.792 | −6.677 | 1.00 | 19.20 | C |
| ATOM | 1410 | CB | MET | A | 86 | 4.220 | 62.395 | −7.757 | 1.00 | 19.02 | C |
| ATOM | 1413 | CG | MET | A | 86 | 4.969 | 61.093 | −7.477 | 1.00 | 19.07 | C |
| ATOM | 1416 | SD | MET | A | 86 | 6.203 | 60.635 | −8.742 | 1.00 | 19.48 | S |
| ATOM | 1417 | CE | MET | A | 86 | 5.127 | 60.071 | −9.966 | 1.00 | 20.83 | C |
| ATOM | 1421 | C | MET | A | 86 | 2.270 | 61.614 | −6.456 | 1.00 | 18.53 | C |
| ATOM | 1422 | O | MET | A | 86 | 2.508 | 60.780 | −5.579 | 1.00 | 17.44 | O |
| ATOM | 1423 | N | ASN | A | 87 | 1.205 | 61.593 | −7.253 | 1.00 | 18.15 | N |
| ATOM | 1425 | CA | ASN | A | 87 | 0.309 | 60.464 | −7.344 | 1.00 | 17.91 | C |
| ATOM | 1427 | CB | ASN | A | 87 | −0.961 | 60.840 | −8.130 | 1.00 | 18.22 | C |
| ATOM | 1430 | CG | ASN | A | 87 | −1.787 | 61.927 | −7.453 | 1.00 | 19.32 | C |
| ATOM | 1431 | OD1 | ASN | A | 87 | −1.529 | 62.311 | −6.312 | 1.00 | 21.74 | O |
| ATOM | 1432 | ND2 | ASN | A | 87 | −2.772 | 62.441 | −8.170 | 1.00 | 20.57 | N |
| ATOM | 1435 | C | ASN | A | 87 | 1.040 | 59.380 | −8.135 | 1.00 | 17.63 | C |
| ATOM | 1436 | O | ASN | A | 87 | 1.931 | 59.669 | −8.920 | 1.00 | 17.03 | O |
| ATOM | 1437 | N | PRO | A | 88 | 0.656 | 58.131 | −7.944 | 1.00 | 17.44 | N |
| ATOM | 1438 | CA | PRO | A | 88 | 1.208 | 57.053 | −8.751 | 1.00 | 17.30 | C |
| ATOM | 1440 | CB | PRO | A | 88 | 0.520 | 55.801 | −8.214 | 1.00 | 17.52 | C |
| ATOM | 1443 | CG | PRO | A | 88 | −0.272 | 56.205 | −7.082 | 1.00 | 18.64 | C |
| ATOM | 1446 | CD | PRO | A | 88 | −0.366 | 57.670 | −6.998 | 1.00 | 17.66 | C |
| ATOM | 1449 | C | PRO | A | 88 | 0.754 | 57.323 | −10.186 | 1.00 | 16.55 | C |
| ATOM | 1450 | O | PRO | A | 88 | −0.418 | 57.560 | −10.386 | 1.00 | 16.30 | O |
| ATOM | 1451 | N | PRO | A | 89 | 1.656 | 57.290 | −11.156 | 1.00 | 16.34 | N |
| ATOM | 1452 | CA | PRO | A | 89 | 1.322 | 57.661 | −12.534 | 1.00 | 16.31 | C |
| ATOM | 1454 | CB | PRO | A | 89 | 2.690 | 57.900 | −13.158 | 1.00 | 16.34 | C |
| ATOM | 1457 | CG | PRO | A | 89 | 3.613 | 56.984 | −12.418 | 1.00 | 16.09 | C |

TABLE I-continued

The atomic coordinates of an altered human IL-18 structure; SEQ ID No: 1 with a C38S substitution.
(P6₁)a = 71.4°, b = 71.4°, c = 88.7°, α,β = 90° and γ = 120°

| ATOM | 1460 | CD  | PRO | A | 89 | 3.068  | 56.908 | −11.006 | 1.00 | 15.95 | C |
|------|------|-----|-----|---|----|--------|--------|---------|------|-------|---|
| ATOM | 1463 | C   | PRO | A | 89 | 0.594  | 56.578 | −13.320 | 1.00 | 16.81 | C |
| ATOM | 1464 | O   | PRO | A | 89 | 0.684  | 55.401 | −12.971 | 1.00 | 16.72 | O |
| ATOM | 1465 | N   | ASP | A | 90 | −0.104 | 56.970 | −14.382 | 1.00 | 16.66 | N |
| ATOM | 1467 | CA  | ASP | A | 90 | −0.786 | 55.993 | −15.228 | 1.00 | 16.97 | C |
| ATOM | 1469 | CB  | ASP | A | 90 | −1.794 | 56.650 | −16.146 | 1.00 | 17.34 | C |
| ATOM | 1472 | CG  | ASP | A | 90 | −2.910 | 57.279 | −15.396 | 1.00 | 19.82 | C |
| ATOM | 1473 | OD1 | ASP | A | 90 | −3.399 | 56.719 | −14.391 | 1.00 | 23.87 | O |
| ATOM | 1474 | OD2 | ASP | A | 90 | −3.364 | 58.356 | −15.751 | 1.00 | 24.07 | O |
| ATOM | 1475 | C   | ASP | A | 90 | 0.177  | 55.247 | −16.085 | 1.00 | 16.16 | C |
| ATOM | 1476 | O   | ASP | A | 90 | −0.050 | 54.103 | −16.356 | 1.00 | 15.59 | O |
| ATOM | 1477 | N   | ASN | A | 91 | 1.239  | 55.903 | −16.521 | 1.00 | 16.99 | N |
| ATOM | 1479 | CA  | ASN | A | 91 | 2.219  | 55.277 | −17.396 | 1.00 | 17.75 | C |
| ATOM | 1481 | CB  | ASN | A | 91 | 1.943  | 55.637 | −18.861 | 1.00 | 18.43 | C |
| ATOM | 1484 | CG  | ASN | A | 91 | 0.623  | 55.090 | −19.349 | 1.00 | 20.34 | C |
| ATOM | 1485 | OD1 | ASN | A | 91 | 0.507  | 53.899 | −19.642 | 1.00 | 21.93 | O |
| ATOM | 1486 | ND2 | ASN | A | 91 | −0.392 | 55.946 | −19.402 | 1.00 | 20.01 | N |
| ATOM | 1489 | C   | ASN | A | 91 | 3.597  | 55.744 | −17.052 | 1.00 | 18.08 | C |
| ATOM | 1490 | O   | ASN | A | 91 | 3.754  | 56.894 | −16.650 | 1.00 | 18.65 | O |
| ATOM | 1491 | N   | ILE | A | 92 | 4.593  | 54.882 | −17.237 | 1.00 | 17.65 | N |
| ATOM | 1493 | CA  | ILE | A | 92 | 5.991  | 55.236 | −17.022 | 1.00 | 17.66 | C |
| ATOM | 1495 | CB  | ILE | A | 92 | 6.547  | 54.583 | −15.744 | 1.00 | 17.40 | C |
| ATOM | 1497 | CG1 | ILE | A | 92 | 5.853  | 55.134 | −14.506 | 1.00 | 16.97 | C |
| ATOM | 1500 | CD1 | ILE | A | 92 | 6.186  | 54.375 | −13.204 | 1.00 | 16.36 | C |
| ATOM | 1504 | CG2 | ILE | A | 92 | 8.031  | 54.791 | −15.643 | 1.00 | 17.36 | C |
| ATOM | 1508 | C   | ILE | A | 92 | 6.728  | 54.729 | −18.245 | 1.00 | 18.49 | C |
| ATOM | 1509 | O   | ILE | A | 92 | 6.680  | 53.535 | −18.557 | 1.00 | 17.20 | O |
| ATOM | 1510 | N   | LYS | A | 93 | 7.401  | 55.638 | −18.943 | 1.00 | 19.65 | N |
| ATOM | 1512 | CA  | LYS | A | 93 | 8.048  | 55.309 | −20.214 | 1.00 | 21.53 | C |
| ATOM | 1514 | CB  | LYS | A | 93 | 8.331  | 56.599 | −21.012 | 1.00 | 22.25 | C |
| ATOM | 1517 | CG  | LYS | A | 93 | 7.081  | 57.281 | −21.541 | 1.00 | 26.39 | C |
| ATOM | 1520 | CD  | LYS | A | 93 | 7.411  | 58.593 | −22.282 | 1.00 | 30.93 | C |
| ATOM | 1523 | CE  | LYS | A | 93 | 6.140  | 59.348 | −22.682 | 1.00 | 33.76 | C |
| ATOM | 1526 | NZ  | LYS | A | 93 | 6.438  | 60.689 | −23.279 | 1.00 | 37.26 | N |
| ATOM | 1530 | C   | LYS | A | 93 | 9.337  | 54.478 | −20.119 | 1.00 | 20.78 | C |
| ATOM | 1531 | O   | LYS | A | 93 | 9.603  | 53.679 | −21.000 | 1.00 | 21.45 | O |
| ATOM | 1532 | N   | ASP | A | 94 | 10.143 | 54.660 | −19.085 | 1.00 | 20.83 | N |
| ATOM | 1534 | CA  | ASP | A | 94 | 11.408 | 53.916 | −18.992 | 1.00 | 21.01 | C |
| ATOM | 1536 | CB  | ASP | A | 94 | 12.419 | 54.672 | −18.113 | 1.00 | 22.05 | C |
| ATOM | 1539 | CG  | ASP | A | 94 | 13.870 | 54.247 | −18.385 | 1.00 | 26.32 | C |
| ATOM | 1540 | OD1 | ASP | A | 94 | 14.167 | 53.837 | −19.535 | 1.00 | 30.63 | O |
| ATOM | 1541 | OD2 | ASP | A | 94 | 14.779 | 54.261 | −17.516 | 1.00 | 33.43 | O |
| ATOM | 1542 | C   | ASP | A | 94 | 11.193 | 52.501 | −18.439 | 1.00 | 19.94 | C |
| ATOM | 1543 | O   | ASP | A | 94 | 10.089 | 52.161 | −18.016 | 1.00 | 18.21 | O |
| ATOM | 1544 | N   | THR | A | 95 | 12.252 | 51.692 | −18.449 | 1.00 | 19.38 | N |
| ATOM | 1546 | CA  | THR | A | 95 | 12.204 | 50.335 | −17.914 | 1.00 | 19.69 | C |
| ATOM | 1548 | CB  | THR | A | 95 | 13.134 | 49.398 | −18.670 | 1.00 | 19.65 | C |
| ATOM | 1550 | OG1 | THR | A | 95 | 14.452 | 49.951 | −18.684 | 1.00 | 19.63 | O |
| ATOM | 1552 | CG2 | THR | A | 95 | 12.754 | 49.261 | −20.128 | 1.00 | 20.76 | C |
| ATOM | 1556 | C   | THR | A | 95 | 12.620 | 50.276 | −16.452 | 1.00 | 19.43 | C |
| ATOM | 1557 | O   | THR | A | 95 | 12.561 | 49.215 | −15.855 | 1.00 | 19.07 | O |
| ATOM | 1558 | N   | LYS | A | 96 | 13.085 | 51.396 | −15.907 | 1.00 | 19.31 | N |
| ATOM | 1560 | CA  | LYS | A | 96 | 13.451 | 51.497 | −14.504 | 1.00 | 19.73 | C |
| ATOM | 1562 | CB  | LYS | A | 96 | 14.962 | 51.493 | −14.337 | 1.00 | 20.55 | C |
| ATOM | 1565 | CG  | LYS | A | 96 | 15.645 | 50.230 | −14.804 | 1.00 | 24.38 | C |
| ATOM | 1568 | CD  | LYS | A | 96 | 17.157 | 50.457 | −14.852 | 1.00 | 29.05 | C |
| ATOM | 1571 | CE  | LYS | A | 96 | 17.911 | 49.261 | −15.397 | 1.00 | 32.09 | C |
| ATOM | 1574 | NZ  | LYS | A | 96 | 17.856 | 48.101 | −14.448 | 1.00 | 35.50 | N |
| ATOM | 1578 | C   | LYS | A | 96 | 12.896 | 52.808 | −13.963 | 1.00 | 18.61 | C |
| ATOM | 1579 | O   | LYS | A | 96 | 12.733 | 53.777 | −14.710 | 1.00 | 18.81 | O |
| ATOM | 1580 | N   | SER | A | 97 | 12.624 | 52.852 | −12.669 | 1.00 | 17.12 | N |
| ATOM | 1582 | CA  | SER | A | 97 | 12.101 | 54.061 | −12.056 | 1.00 | 16.69 | C |
| ATOM | 1584 | CB  | SER | A | 97 | 10.606 | 54.179 | −12.308 | 1.00 | 16.53 | C |
| ATOM | 1587 | OG  | SER | A | 97 | 10.035 | 55.180 | −11.490 | 1.00 | 15.88 | O |
| ATOM | 1589 | C   | SER | A | 97 | 12.343 | 54.056 | −10.561 | 1.00 | 16.60 | C |
| ATOM | 1590 | O   | SER | A | 97 | 12.147 | 53.019 | −9.898  | 1.00 | 15.71 | O |
| ATOM | 1591 | N   | ASP | A | 98 | 12.745 | 55.213 | −10.033 | 1.00 | 16.12 | N |
| ATOM | 1593 | CA  | ASP | A | 98 | 12.958 | 55.385 | −8.599  | 1.00 | 16.77 | C |
| ATOM | 1595 | CB  | ASP | A | 98 | 13.420 | 56.810 | −8.288  | 1.00 | 17.52 | C |
| ATOM | 1598 | CG  | ASP | A | 98 | 14.836 | 57.100 | −8.780  | 1.00 | 20.61 | C |
| ATOM | 1599 | OD1 | ASP | A | 98 | 15.595 | 56.159 | −9.082  | 1.00 | 23.09 | O |
| ATOM | 1600 | OD2 | ASP | A | 98 | 15.267 | 58.264 | −8.903  | 1.00 | 26.80 | O |
| ATOM | 1601 | C   | ASP | A | 98 | 11.707 | 55.073 | −7.745  | 1.00 | 15.80 | C |
| ATOM | 1602 | O   | ASP | A | 98 | 11.835 | 54.865 | −6.543  | 1.00 | 16.33 | O |
| ATOM | 1603 | N   | ILE | A | 99 | 10.516 | 55.055 | −8.347  | 1.00 | 14.68 | N |

TABLE I-continued

The atomic coordinates of an altered human IL-18 structure; SEQ ID No: 1 with a C38S substitution. ($P6_1$)a = 71.4°, b = 71.4°, c = 88.7°, α,β = 90° and γ = 120°

| | | | | | | | | | | | |
|---|---|---|---|---|---|---|---|---|---|---|---|
| ATOM | 1605 | CA | ILE | A | 99 | 9.285 | 54.718 | −7.608 | 1.00 | 13.94 | C |
| ATOM | 1607 | CB | ILE | A | 99 | 8.184 | 55.748 | −7.843 | 1.00 | 13.90 | C |
| ATOM | 1609 | CG1 | ILE | A | 99 | 7.784 | 55.789 | −9.314 | 1.00 | 15.06 | C |
| ATOM | 1612 | CD1 | ILE | A | 99 | 6.509 | 56.521 | −9.523 | 1.00 | 16.61 | C |
| ATOM | 1616 | CG2 | ILE | A | 99 | 8.611 | 57.133 | −7.322 | 1.00 | 13.31 | C |
| ATOM | 1620 | C | ILE | A | 99 | 8.740 | 53.306 | −7.900 | 1.00 | 13.36 | C |
| ATOM | 1621 | O | ILE | A | 99 | 7.748 | 52.872 | −7.321 | 1.00 | 12.61 | O |
| ATOM | 1622 | N | ILE | A | 100 | 9.398 | 52.562 | −8.766 | 1.00 | 12.80 | N |
| ATOM | 1624 | CA | ILE | A | 100 | 8.914 | 51.229 | −9.058 | 1.00 | 12.44 | C |
| ATOM | 1626 | CB | ILE | A | 100 | 8.900 | 50.948 | −10.574 | 1.00 | 12.60 | C |
| ATOM | 1628 | CG1 | ILE | A | 100 | 7.762 | 51.701 | −11.254 | 1.00 | 12.35 | C |
| ATOM | 1631 | CD1 | ILE | A | 100 | 6.408 | 51.100 | −10.984 | 1.00 | 13.67 | C |
| ATOM | 1635 | CG2 | ILE | A | 100 | 8.795 | 49.424 | −10.850 | 1.00 | 12.45 | C |
| ATOM | 1639 | C | ILE | A | 100 | 9.791 | 50.215 | −8.364 | 1.00 | 12.45 | C |
| ATOM | 1640 | O | ILE | A | 100 | 11.016 | 50.256 | −8.487 | 1.00 | 12.10 | O |
| ATOM | 1641 | N | PHE | A | 101 | 9.145 | 49.322 | −7.625 | 1.00 | 12.17 | N |
| ATOM | 1643 | CA | PHE | A | 101 | 9.812 | 48.163 | −7.017 | 1.00 | 12.36 | C |
| ATOM | 1645 | CB | PHE | A | 101 | 9.500 | 48.115 | −5.534 | 1.00 | 12.44 | C |
| ATOM | 1648 | CG | PHE | A | 101 | 10.006 | 49.293 | −4.797 | 1.00 | 13.57 | C |
| ATOM | 1649 | CD1 | PHE | A | 101 | 9.281 | 50.467 | −4.768 | 1.00 | 15.70 | C |
| ATOM | 1651 | CE1 | PHE | A | 101 | 9.783 | 51.592 | −4.109 | 1.00 | 16.59 | C |
| ATOM | 1653 | CZ | PHE | A | 101 | 11.001 | 51.523 | −3.481 | 1.00 | 15.46 | C |
| ATOM | 1655 | CE2 | PHE | A | 101 | 11.741 | 50.349 | −3.530 | 1.00 | 14.93 | C |
| ATOM | 1657 | CD2 | PHE | A | 101 | 11.249 | 49.255 | −4.189 | 1.00 | 15.36 | C |
| ATOM | 1659 | C | PHE | A | 101 | 9.267 | 46.894 | −7.620 | 1.00 | 12.29 | C |
| ATOM | 1660 | O | PHE | A | 101 | 8.111 | 46.876 | −8.051 | 1.00 | 13.32 | O |
| ATOM | 1661 | N | PHE | A | 102 | 10.074 | 45.836 | −7.637 | 1.00 | 12.07 | N |
| ATOM | 1663 | CA | PHE | A | 102 | 9.614 | 44.514 | −8.048 | 1.00 | 11.87 | C |
| ATOM | 1665 | CB | PHE | A | 102 | 10.650 | 43.789 | −8.904 | 1.00 | 12.23 | C |
| ATOM | 1668 | CG | PHE | A | 102 | 10.994 | 44.513 | −10.170 | 1.00 | 12.55 | C |
| ATOM | 1669 | CD1 | PHE | A | 102 | 10.010 | 44.844 | −11.074 | 1.00 | 12.71 | C |
| ATOM | 1671 | CE1 | PHE | A | 102 | 10.310 | 45.534 | −12.251 | 1.00 | 12.56 | C |
| ATOM | 1673 | CZ | PHE | A | 102 | 11.603 | 45.883 | −12.526 | 1.00 | 12.26 | C |
| ATOM | 1675 | CE2 | PHE | A | 102 | 12.608 | 45.569 | −11.628 | 1.00 | 13.73 | C |
| ATOM | 1677 | CD2 | PHE | A | 102 | 12.298 | 44.881 | −10.444 | 1.00 | 13.67 | C |
| ATOM | 1679 | C | PHE | A | 102 | 9.322 | 43.692 | −6.804 | 1.00 | 12.04 | C |
| ATOM | 1680 | O | PHE | A | 102 | 10.238 | 43.372 | −6.008 | 1.00 | 10.74 | O |
| ATOM | 1681 | N | GLN | A | 103 | 8.040 | 43.379 | −6.634 | 1.00 | 12.14 | N |
| ATOM | 1683 | CA | GLN | A | 103 | 7.569 | 42.594 | −5.498 | 1.00 | 12.54 | C |
| ATOM | 1685 | CB | GLN | A | 103 | 6.150 | 43.027 | −5.067 | 1.00 | 12.77 | C |
| ATOM | 1688 | CG | GLN | A | 103 | 5.586 | 42.242 | −3.874 | 1.00 | 13.09 | C |
| ATOM | 1691 | CD | GLN | A | 103 | 4.110 | 42.519 | −3.613 | 1.00 | 15.81 | C |
| ATOM | 1692 | OE1 | GLN | A | 103 | 3.644 | 43.636 | −3.842 | 1.00 | 14.73 | O |
| ATOM | 1693 | NE2 | GLN | A | 103 | 3.380 | 41.509 | −3.117 | 1.00 | 12.31 | N |
| ATOM | 1696 | C | GLN | A | 103 | 7.558 | 41.129 | −5.904 | 1.00 | 12.68 | C |
| ATOM | 1697 | O | GLN | A | 103 | 6.936 | 40.759 | −6.924 | 1.00 | 11.91 | O |
| ATOM | 1698 | N | ARG | A | 104 | 8.246 | 40.309 | −5.115 | 1.00 | 12.59 | N |
| ATOM | 1700 | CA | ARG | A | 104 | 8.312 | 38.882 | −5.356 | 1.00 | 12.69 | C |
| ATOM | 1702 | CB | ARG | A | 104 | 9.641 | 38.520 | −5.995 | 1.00 | 13.11 | C |
| ATOM | 1705 | CG | ARG | A | 104 | 9.971 | 39.273 | −7.249 | 1.00 | 12.76 | C |
| ATOM | 1708 | CD | ARG | A | 104 | 11.322 | 38.865 | −7.780 | 1.00 | 13.77 | C |
| ATOM | 1711 | NE | ARG | A | 104 | 11.823 | 39.587 | −8.948 | 1.00 | 12.44 | N |
| ATOM | 1713 | CZ | ARG | A | 104 | 12.619 | 40.640 | −8.900 | 1.00 | 14.71 | C |
| ATOM | 1714 | NH1 | ARG | A | 104 | 12.980 | 41.176 | −7.737 | 1.00 | 15.15 | N |
| ATOM | 1717 | NH2 | ARG | A | 104 | 13.068 | 41.168 | −10.027 | 1.00 | 16.82 | N |
| ATOM | 1720 | C | ARG | A | 104 | 8.208 | 38.127 | −4.034 | 1.00 | 13.39 | C |
| ATOM | 1721 | O | ARG | A | 104 | 8.637 | 38.623 | −2.994 | 1.00 | 12.61 | O |
| ATOM | 1722 | N | SER | A | 105 | 7.655 | 36.922 | −4.084 | 1.00 | 13.60 | N |
| ATOM | 1724 | CA | SER | A | 105 | 7.547 | 36.095 | −2.888 | 1.00 | 14.97 | C |
| ATOM | 1726 | CB | SER | A | 105 | 6.381 | 35.125 | −3.024 | 1.00 | 14.57 | C |
| ATOM | 1729 | OG | SER | A | 105 | 6.630 | 34.230 | −4.085 | 1.00 | 19.33 | O |
| ATOM | 1731 | C | SER | A | 105 | 8.864 | 35.346 | −2.630 | 1.00 | 15.36 | C |
| ATOM | 1732 | O | SER | A | 105 | 9.699 | 35.198 | −3.532 | 1.00 | 14.86 | O |
| ATOM | 1733 | N | VAL | A | 106 | 9.027 | 34.905 | −1.385 | 1.00 | 15.75 | N |
| ATOM | 1735 | CA | VAL | A | 106 | 10.179 | 34.148 | −0.919 | 1.00 | 16.79 | C |
| ATOM | 1737 | CB | VAL | A | 106 | 10.325 | 34.302 | 0.612 | 1.00 | 16.88 | C |
| ATOM | 1739 | CG1 | VAL | A | 106 | 11.369 | 33.302 | 1.212 | 1.00 | 18.13 | C |
| ATOM | 1743 | CG2 | VAL | A | 106 | 10.739 | 35.725 | 0.967 | 1.00 | 17.82 | C |
| ATOM | 1747 | C | VAL | A | 106 | 9.967 | 32.661 | −1.261 | 1.00 | 17.26 | C |
| ATOM | 1748 | O | VAL | A | 106 | 8.890 | 32.128 | −1.014 | 1.00 | 16.36 | O |
| ATOM | 1749 | N | PRO | A | 107 | 10.989 | 31.991 | −1.787 | 1.00 | 18.48 | N |
| ATOM | 1750 | CA | PRO | A | 107 | 10.880 | 30.569 | −2.122 | 1.00 | 19.71 | C |
| ATOM | 1752 | CB | PRO | A | 107 | 12.324 | 30.167 | −2.458 | 1.00 | 20.21 | C |
| ATOM | 1755 | CG | PRO | A | 107 | 13.024 | 31.427 | −2.795 | 1.00 | 20.09 | C |
| ATOM | 1758 | CD | PRO | A | 107 | 12.340 | 32.513 | −2.039 | 1.00 | 19.23 | C |

TABLE I-continued

The atomic coordinates of an altered human IL-18 structure; SEQ ID No: 1 with a C38S substitution.
(P6₁)a = 71.4°, b = 71.4°, c = 88.7°, α,β = 90° and γ = 120°

| ATOM | 1761 | C   | PRO | A | 107 | 10.362 | 29.762 | -0.934 | 1.00 | 20.35 | C |
|------|------|-----|-----|---|-----|--------|--------|--------|------|-------|---|
| ATOM | 1762 | O   | PRO | A | 107 | 10.827 | 29.941 | 0.180  | 1.00 | 20.97 | O |
| ATOM | 1763 | N   | GLY | A | 108 | 9.358  | 28.937 | -1.156 | 1.00 | 21.08 | N |
| ATOM | 1765 | CA  | GLY | A | 108 | 8.796  | 28.126 | -0.093 | 1.00 | 21.86 | C |
| ATOM | 1768 | C   | GLY | A | 108 | 7.875  | 28.915 | 0.824  | 1.00 | 22.31 | C |
| ATOM | 1769 | O   | GLY | A | 108 | 7.304  | 28.362 | 1.768  | 1.00 | 22.33 | O |
| ATOM | 1770 | N   | HIS | A | 109 | 7.726  | 30.215 | 0.581  | 1.00 | 21.77 | N |
| ATOM | 1772 | CA  | HIS | A | 109 | 6.893  | 31.023 | 1.473  | 1.00 | 22.02 | C |
| ATOM | 1774 | CB  | HIS | A | 109 | 7.775  | 31.695 | 2.523  | 1.00 | 22.31 | C |
| ATOM | 1777 | CG  | HIS | A | 109 | 8.517  | 30.730 | 3.395  | 1.00 | 25.08 | C |
| ATOM | 1778 | ND1 | HIS | A | 109 | 7.907  | 30.025 | 4.410  | 1.00 | 27.83 | N |
| ATOM | 1780 | CE1 | HIS | A | 109 | 8.797  | 29.242 | 4.996  | 1.00 | 28.02 | C |
| ATOM | 1782 | NE2 | HIS | A | 109 | 9.962  | 29.417 | 4.401  | 1.00 | 27.77 | N |
| ATOM | 1784 | CD2 | HIS | A | 109 | 9.813  | 30.336 | 3.389  | 1.00 | 27.14 | C |
| ATOM | 1786 | C   | HIS | A | 109 | 6.149  | 32.096 | 0.682  | 1.00 | 21.47 | C |
| ATOM | 1787 | O   | HIS | A | 109 | 6.548  | 33.248 | 0.656  | 1.00 | 21.06 | O |
| ATOM | 1788 | N   | ASP | A | 110 | 5.050  | 31.687 | 0.079  | 1.00 | 20.80 | N |
| ATOM | 1790 | CA  | ASP | A | 110 | 4.313  | 32.526 | -0.862 | 1.00 | 20.89 | C |
| ATOM | 1792 | CB  | ASP | A | 110 | 3.156  | 31.734 | -1.471 | 1.00 | 20.71 | C |
| ATOM | 1795 | CG  | ASP | A | 110 | 3.628  | 30.630 | -2.420 | 1.00 | 21.84 | C |
| ATOM | 1796 | OD1 | ASP | A | 110 | 4.833  | 30.566 | -2.752 | 1.00 | 21.04 | O |
| ATOM | 1797 | OD2 | ASP | A | 110 | 2.851  | 29.779 | -2.895 | 1.00 | 24.11 | O |
| ATOM | 1798 | C   | ASP | A | 110 | 3.793  | 33.844 | -0.286 | 1.00 | 20.30 | C |
| ATOM | 1799 | O   | ASP | A | 110 | 3.680  | 34.824 | -1.002 | 1.00 | 20.42 | O |
| ATOM | 1800 | N   | ASN | A | 111 | 3.502  | 33.868 | 0.997  | 1.00 | 19.82 | N |
| ATOM | 1802 | CA  | ASN | A | 111 | 2.993  | 35.067 | 1.631  | 1.00 | 20.23 | C |
| ATOM | 1804 | CB  | ASN | A | 111 | 2.242  | 34.648 | 2.881  | 1.00 | 21.26 | C |
| ATOM | 1807 | CG  | ASN | A | 111 | 3.125  | 33.856 | 3.828  | 1.00 | 25.09 | C |
| ATOM | 1808 | OD1 | ASN | A | 111 | 3.862  | 32.934 | 3.401  | 1.00 | 29.93 | O |
| ATOM | 1809 | ND2 | ASN | A | 111 | 3.073  | 34.203 | 5.117  | 1.00 | 30.79 | N |
| ATOM | 1812 | C   | ASN | A | 111 | 4.071  | 36.062 | 2.056  | 1.00 | 19.06 | C |
| ATOM | 1813 | O   | ASN | A | 111 | 3.765  | 37.179 | 2.460  | 1.00 | 18.64 | O |
| ATOM | 1814 | N   | LYS | A | 112 | 5.325  | 35.647 | 2.025  | 1.00 | 17.77 | N |
| ATOM | 1816 | CA  | LYS | A | 112 | 6.400  | 36.535 | 2.415  | 1.00 | 17.52 | C |
| ATOM | 1818 | CB  | LYS | A | 112 | 7.486  | 35.767 | 3.147  | 1.00 | 18.06 | C |
| ATOM | 1821 | CG  | LYS | A | 112 | 6.995  | 35.139 | 4.476  | 1.00 | 20.76 | C |
| ATOM | 1824 | CD  | LYS | A | 112 | 8.137  | 34.434 | 5.175  | 1.00 | 26.65 | C |
| ATOM | 1827 | CE  | LYS | A | 112 | 7.791  | 34.031 | 6.621  | 1.00 | 30.48 | C |
| ATOM | 1830 | NZ  | LYS | A | 112 | 8.979  | 33.389 | 7.293  | 1.00 | 32.51 | N |
| ATOM | 1834 | C   | LYS | A | 112 | 6.949  | 37.208 | 1.164  | 1.00 | 16.43 | C |
| ATOM | 1835 | O   | LYS | A | 112 | 7.365  | 36.528 | 0.211  | 1.00 | 16.35 | O |
| ATOM | 1836 | N   | MET | A | 113 | 6.948  | 38.528 | 1.186  | 1.00 | 15.04 | N |
| ATOM | 1838 | CA  | MET | A | 113 | 7.370  | 39.344 | 0.053  | 1.00 | 14.21 | C |
| ATOM | 1840 | CB  | MET | A | 113 | 6.189  | 40.262 | -0.305 | 1.00 | 13.98 | C |
| ATOM | 1843 | CG  | MET | A | 113 | 4.922  | 39.491 | -0.557 | 1.00 | 13.92 | C |
| ATOM | 1846 | SD  | MET | A | 113 | 4.959  | 38.666 | -2.121 | 1.00 | 13.76 | S |
| ATOM | 1847 | CE  | MET | A | 113 | 3.272  | 37.917 | -2.118 | 1.00 | 16.42 | C |
| ATOM | 1851 | C   | MET | A | 113 | 8.621  | 40.218 | 0.248  | 1.00 | 13.87 | C |
| ATOM | 1852 | O   | MET | A | 113 | 8.915  | 40.713 | 1.356  | 1.00 | 14.54 | O |
| ATOM | 1853 | N   | GLN | A | 114 | 9.360  | 40.416 | -0.849 | 1.00 | 13.03 | N |
| ATOM | 1855 | CA  | GLN | A | 114 | 10.529 | 41.289 | -0.867 | 1.00 | 13.01 | C |
| ATOM | 1857 | CB  | GLN | A | 114 | 11.823 | 40.493 | -1.094 | 1.00 | 12.49 | C |
| ATOM | 1860 | CG  | GLN | A | 114 | 12.016 | 39.398 | -0.064 | 1.00 | 13.98 | C |
| ATOM | 1863 | CD  | GLN | A | 114 | 13.271 | 38.583 | -0.249 | 1.00 | 12.98 | C |
| ATOM | 1864 | OE1 | GLN | A | 114 | 13.707 | 38.380 | -1.368 | 1.00 | 16.00 | O |
| ATOM | 1865 | NE2 | GLN | A | 114 | 13.836 | 38.081 | 0.865  | 1.00 | 13.37 | N |
| ATOM | 1868 | C   | GLN | A | 114 | 10.319 | 42.283 | -2.007 | 1.00 | 12.07 | C |
| ATOM | 1869 | O   | GLN | A | 114 | 9.772  | 41.923 | -3.052 | 1.00 | 12.02 | O |
| ATOM | 1870 | N   | PHE | A | 115 | 10.792 | 43.501 | -1.806 | 1.00 | 11.94 | N |
| ATOM | 1872 | CA  | PHE | A | 115 | 10.632 | 44.605 | -2.755 | 1.00 | 11.72 | C |
| ATOM | 1874 | CB  | PHE | A | 115 | 9.881  | 45.780 | -2.108 | 1.00 | 11.68 | C |
| ATOM | 1877 | CG  | PHE | A | 115 | 8.477  | 45.457 | -1.659 | 1.00 | 11.29 | C |
| ATOM | 1878 | CD1 | PHE | A | 115 | 8.228  | 45.040 | -0.373 | 1.00 | 13.40 | C |
| ATOM | 1880 | CE1 | PHE | A | 115 | 6.930  | 44.747 | 0.052  | 1.00 | 13.23 | C |
| ATOM | 1882 | CZ  | PHE | A | 115 | 5.863  | 44.889 | -0.838 | 1.00 | 11.77 | C |
| ATOM | 1884 | CE2 | PHE | A | 115 | 6.109  | 45.310 | -2.115 | 1.00 | 11.16 | C |
| ATOM | 1886 | CD2 | PHE | A | 115 | 7.407  | 45.593 | -2.527 | 1.00 | 10.60 | C |
| ATOM | 1888 | C   | PHE | A | 115 | 12.004 | 45.086 | -3.183 | 1.00 | 11.91 | C |
| ATOM | 1889 | O   | PHE | A | 115 | 12.724 | 45.735 | -2.400 | 1.00 | 11.30 | O |
| ATOM | 1890 | N   | GLU | A | 116 | 12.366 | 44.761 | -4.420 | 1.00 | 12.11 | N |
| ATOM | 1892 | CA  | GLU | A | 116 | 13.645 | 45.155 | -4.978 | 1.00 | 12.59 | C |
| ATOM | 1894 | CB  | GLU | A | 116 | 14.211 | 44.048 | -5.855 | 1.00 | 12.65 | C |
| ATOM | 1897 | CG  | GLU | A | 116 | 15.623 | 44.359 | -6.297 | 1.00 | 13.88 | C |
| ATOM | 1900 | CD  | GLU | A | 116 | 16.307 | 43.210 | -6.996 | 1.00 | 17.12 | C |
| ATOM | 1901 | OE1 | GLU | A | 116 | 15.651 | 42.174 | -7.263 | 1.00 | 16.35 | O |

TABLE I-continued

The atomic coordinates of an altered human IL-18 structure; SEQ ID No: 1 with a C38S substitution.
(P6₁) a = 71.4°, b = 71.4°, c = 88.7°, α,β = 90° and γ = 120°

| ATOM | 1902 | OE2 | GLU | A | 116 | 17.516 | 43.370 | −7.278 | 1.00 | 18.56 | O |
|---|---|---|---|---|---|---|---|---|---|---|---|
| ATOM | 1903 | C | GLU | A | 116 | 13.509 | 46.436 | −5.806 | 1.00 | 12.91 | C |
| ATOM | 1904 | O | GLU | A | 116 | 12.596 | 46.556 | −6.614 | 1.00 | 12.73 | O |
| ATOM | 1905 | N | SER | A | 117 | 14.408 | 47.393 | −5.592 | 1.00 | 13.50 | N |
| ATOM | 1907 | CA | SER | A | 117 | 14.411 | 48.620 | −6.384 | 1.00 | 14.35 | C |
| ATOM | 1909 | CB | SER | A | 117 | 15.515 | 49.569 | −5.892 | 1.00 | 15.10 | C |
| ATOM | 1912 | OG | SER | A | 117 | 15.714 | 50.667 | −6.788 | 1.00 | 14.74 | O |
| ATOM | 1914 | C | SER | A | 117 | 14.631 | 48.296 | −7.867 | 1.00 | 14.72 | C |
| ATOM | 1915 | O | SER | A | 117 | 15.538 | 47.538 | −8.208 | 1.00 | 15.22 | O |
| ATOM | 1916 | N | SER | A | 118 | 13.778 | 48.830 | −8.740 | 1.00 | 15.09 | N |
| ATOM | 1918 | CA | SER | A | 118 | 13.978 | 48.678 | −10.171 | 1.00 | 14.99 | C |
| ATOM | 1920 | CB | SER | A | 118 | 12.705 | 49.022 | −10.946 | 1.00 | 15.09 | C |
| ATOM | 1923 | OG | SER | A | 118 | 12.451 | 50.426 | −11.012 | 1.00 | 11.74 | O |
| ATOM | 1925 | C | SER | A | 118 | 15.136 | 49.578 | −10.636 | 1.00 | 16.66 | C |
| ATOM | 1926 | O | SER | A | 118 | 15.805 | 49.276 | −11.606 | 1.00 | 16.60 | O |
| ATOM | 1927 | N | SER | A | 119 | 15.344 | 50.706 | −9.960 | 1.00 | 17.88 | N |
| ATOM | 1929 | CA | SER | A | 119 | 16.457 | 51.595 | −10.288 | 1.00 | 19.19 | C |
| ATOM | 1931 | CB | SER | A | 119 | 16.272 | 52.944 | −9.598 | 1.00 | 19.61 | C |
| ATOM | 1934 | OG | SER | A | 119 | 15.222 | 53.666 | −10.200 | 1.00 | 22.09 | O |
| ATOM | 1936 | C | SER | A | 119 | 17.814 | 51.035 | −9.863 | 1.00 | 19.56 | C |
| ATOM | 1937 | O | SER | A | 119 | 18.805 | 51.193 | −10.556 | 1.00 | 19.51 | O |
| ATOM | 1938 | N | TYR | A | 120 | 17.850 | 50.394 | −8.707 | 1.00 | 19.94 | N |
| ATOM | 1940 | CA | TYR | A | 120 | 19.100 | 49.907 | −8.155 | 1.00 | 20.38 | C |
| ATOM | 1942 | CB | TYR | A | 120 | 19.450 | 50.716 | −6.912 | 1.00 | 20.58 | C |
| ATOM | 1945 | CG | TYR | A | 120 | 19.531 | 52.193 | −7.167 | 1.00 | 22.52 | C |
| ATOM | 1946 | CD1 | TYR | A | 120 | 20.598 | 52.743 | −7.862 | 1.00 | 24.80 | C |
| ATOM | 1948 | CE1 | TYR | A | 120 | 20.673 | 54.100 | −8.093 | 1.00 | 25.50 | C |
| ATOM | 1950 | CZ | TYR | A | 120 | 19.673 | 54.911 | −7.625 | 1.00 | 27.56 | C |
| ATOM | 1951 | OH | TYR | A | 120 | 19.709 | 56.273 | −7.831 | 1.00 | 30.87 | O |
| ATOM | 1953 | CE2 | TYR | A | 120 | 18.612 | 54.375 | −6.928 | 1.00 | 26.60 | C |
| ATOM | 1955 | CD2 | TYR | A | 120 | 18.551 | 53.037 | −6.707 | 1.00 | 24.11 | C |
| ATOM | 1957 | C | TYR | A | 120 | 19.029 | 48.419 | −7.812 | 1.00 | 20.60 | C |
| ATOM | 1958 | O | TYR | A | 120 | 18.608 | 48.032 | −6.720 | 1.00 | 19.19 | O |
| ATOM | 1959 | N | GLU | A | 121 | 19.458 | 47.594 | −8.765 | 1.00 | 21.07 | N |
| ATOM | 1961 | CA | GLU | A | 121 | 19.440 | 46.159 | −8.612 | 1.00 | 21.63 | C |
| ATOM | 1963 | CB | GLU | A | 121 | 20.069 | 45.522 | −9.845 | 1.00 | 22.73 | C |
| ATOM | 1966 | CG | GLU | A | 121 | 19.781 | 44.044 | −9.995 | 1.00 | 26.38 | C |
| ATOM | 1969 | CD | GLU | A | 121 | 20.300 | 43.492 | −11.314 | 1.00 | 32.06 | C |
| ATOM | 1970 | OE1 | GLU | A | 121 | 21.219 | 44.116 | −11.897 | 1.00 | 35.93 | O |
| ATOM | 1971 | OE2 | GLU | A | 121 | 19.796 | 42.431 | −11.759 | 1.00 | 35.78 | O |
| ATOM | 1972 | C | GLU | A | 121 | 20.235 | 45.795 | −7.363 | 1.00 | 20.72 | C |
| ATOM | 1973 | O | GLU | A | 121 | 21.236 | 46.429 | −7.070 | 1.00 | 20.21 | O |
| ATOM | 1974 | N | GLY | A | 122 | 19.776 | 44.799 | −6.614 | 1.00 | 19.88 | N |
| ATOM | 1976 | CA | GLY | A | 122 | 20.480 | 44.377 | −5.418 | 1.00 | 19.28 | C |
| ATOM | 1979 | C | GLY | A | 122 | 20.122 | 45.173 | −4.174 | 1.00 | 18.88 | C |
| ATOM | 1980 | O | GLY | A | 122 | 20.586 | 44.843 | −3.074 | 1.00 | 19.51 | O |
| ATOM | 1981 | N | TYR | A | 123 | 19.304 | 46.207 | −4.334 | 1.00 | 17.36 | N |
| ATOM | 1983 | CA | TYR | A | 123 | 18.830 | 46.995 | −3.210 | 1.00 | 17.27 | C |
| ATOM | 1985 | CB | TYR | A | 123 | 19.013 | 48.481 | −3.472 | 1.00 | 17.67 | C |
| ATOM | 1988 | CG | TYR | A | 123 | 20.445 | 48.940 | −3.412 | 1.00 | 19.94 | C |
| ATOM | 1989 | CD1 | TYR | A | 123 | 21.364 | 48.553 | −4.384 | 1.00 | 22.10 | C |
| ATOM | 1991 | CE1 | TYR | A | 123 | 22.686 | 48.980 | −4.334 | 1.00 | 23.22 | C |
| ATOM | 1993 | CZ | TYR | A | 123 | 23.090 | 49.814 | −3.306 | 1.00 | 23.86 | C |
| ATOM | 1994 | OH | TYR | A | 123 | 24.383 | 50.248 | −3.249 | 1.00 | 26.72 | O |
| ATOM | 1996 | CE2 | TYR | A | 123 | 22.204 | 50.214 | −2.334 | 1.00 | 23.71 | C |
| ATOM | 1998 | CD2 | TYR | A | 123 | 20.879 | 49.777 | −2.395 | 1.00 | 22.89 | C |
| ATOM | 2000 | C | TYR | A | 123 | 17.360 | 46.711 | −2.926 | 1.00 | 16.35 | C |
| ATOM | 2001 | O | TYR | A | 123 | 16.541 | 46.652 | −3.858 | 1.00 | 15.82 | O |
| ATOM | 2002 | N | PHE | A | 124 | 17.030 | 46.582 | −1.643 | 1.00 | 14.95 | N |
| ATOM | 2004 | CA | PHE | A | 124 | 15.686 | 46.193 | −1.217 | 1.00 | 14.48 | C |
| ATOM | 2006 | CB | PHE | A | 124 | 15.677 | 44.725 | −0.735 | 1.00 | 14.44 | C |
| ATOM | 2009 | CG | PHE | A | 124 | 16.008 | 43.690 | −1.802 | 1.00 | 14.62 | C |
| ATOM | 2010 | CD1 | PHE | A | 124 | 17.315 | 43.465 | −2.196 | 1.00 | 14.70 | C |
| ATOM | 2012 | CE1 | PHE | A | 124 | 17.625 | 42.498 | −3.141 | 1.00 | 15.20 | C |
| ATOM | 2014 | CZ | PHE | A | 124 | 16.617 | 41.736 | −3.720 | 1.00 | 15.64 | C |
| ATOM | 2016 | CE2 | PHE | A | 124 | 15.314 | 41.941 | −3.330 | 1.00 | 15.03 | C |
| ATOM | 2018 | CD2 | PHE | A | 124 | 15.010 | 42.915 | −2.367 | 1.00 | 13.83 | C |
| ATOM | 2020 | C | PHE | A | 124 | 15.174 | 47.040 | −0.051 | 1.00 | 14.20 | C |
| ATOM | 2021 | O | PHE | A | 124 | 15.941 | 47.599 | 0.748 | 1.00 | 13.50 | O |
| ATOM | 2022 | N | LEU | A | 125 | 13.855 | 47.111 | 0.046 | 1.00 | 13.56 | N |
| ATOM | 2024 | CA | LEU | A | 125 | 13.214 | 47.690 | 1.194 | 1.00 | 14.11 | C |
| ATOM | 2026 | CB | LEU | A | 125 | 11.709 | 47.752 | 0.999 | 1.00 | 14.06 | C |
| ATOM | 2029 | CG | LEU | A | 125 | 11.236 | 48.727 | −0.070 | 1.00 | 15.16 | C |
| ATOM | 2031 | CD1 | LEU | A | 125 | 9.739 | 48.789 | −0.067 | 1.00 | 14.42 | C |
| ATOM | 2035 | CD2 | LEU | A | 125 | 11.849 | 50.138 | 0.192 | 1.00 | 15.65 | C |

TABLE I-continued

The atomic coordinates of an altered human IL-18 structure; SEQ ID No: 1 with a C38S substitution.
(P6₁) a = 71.4°, b = 71.4°, c = 88.7°, α,β = 90° and γ = 120°

| ATOM | 2039 | C | LEU | A | 125 | 13.549 | 46.778 | 2.370 | 1.00 | 14.51 | C |
|---|---|---|---|---|---|---|---|---|---|---|---|
| ATOM | 2040 | O | LEU | A | 125 | 13.493 | 45.547 | 2.249 | 1.00 | 14.05 | O |
| ATOM | 2041 | N | ALA | A | 126 | 13.884 | 47.379 | 3.500 | 1.00 | 15.24 | N |
| ATOM | 2043 | CA | ALA | A | 126 | 14.255 | 46.625 | 4.680 | 1.00 | 15.67 | C |
| ATOM | 2045 | CB | ALA | A | 126 | 15.737 | 46.388 | 4.686 | 1.00 | 16.08 | C |
| ATOM | 2049 | C | ALA | A | 126 | 13.851 | 47.335 | 5.963 | 1.00 | 16.61 | C |
| ATOM | 2050 | O | ALA | A | 126 | 13.628 | 48.551 | 5.982 | 1.00 | 15.79 | O |
| ATOM | 2051 | N | CYS | A | 127 | 13.730 | 46.549 | 7.027 | 1.00 | 16.97 | N |
| ATOM | 2053 | CA | CYS | A | 127 | 13.480 | 47.091 | 8.343 | 1.00 | 18.16 | C |
| ATOM | 2055 | CB | CYS | A | 127 | 12.465 | 46.245 | 9.111 | 1.00 | 17.89 | C |
| ATOM | 2058 | SG | CYS | A | 127 | 12.136 | 46.914 | 10.744 | 1.00 | 17.43 | S |
| ATOM | 2059 | C | CYS | A | 127 | 14.806 | 47.070 | 9.080 | 1.00 | 19.26 | C |
| ATOM | 2060 | O | CYS | A | 127 | 15.488 | 46.049 | 9.098 | 1.00 | 17.87 | O |
| ATOM | 2061 | N | GLU | A | 128 | 15.173 | 48.193 | 9.669 | 1.00 | 21.56 | N |
| ATOM | 2063 | CA | GLU | A | 128 | 16.411 | 48.272 | 10.430 | 1.00 | 24.21 | C |
| ATOM | 2065 | CB | GLU | A | 128 | 17.484 | 49.021 | 9.651 | 1.00 | 24.99 | C |
| ATOM | 2068 | CG | GLU | A | 128 | 18.782 | 49.161 | 10.429 | 1.00 | 28.30 | C |
| ATOM | 2071 | CD | GLU | A | 128 | 19.923 | 49.638 | 9.561 | 1.00 | 32.20 | C |
| ATOM | 2072 | OE1 | GLU | A | 128 | 20.405 | 48.843 | 8.720 | 1.00 | 34.84 | O |
| ATOM | 2073 | OE2 | GLU | A | 128 | 20.322 | 50.808 | 9.713 | 1.00 | 35.17 | O |
| ATOM | 2074 | C | GLU | A | 128 | 16.179 | 48.983 | 11.747 | 1.00 | 25.58 | C |
| ATOM | 2075 | O | GLU | A | 128 | 15.650 | 50.086 | 11.790 | 1.00 | 25.14 | O |
| ATOM | 2076 | N | LYS | A | 129 | 16.561 | 48.339 | 12.834 | 1.00 | 28.08 | N |
| ATOM | 2078 | CA | LYS | A | 129 | 16.439 | 48.977 | 14.134 | 1.00 | 30.46 | C |
| ATOM | 2080 | CB | LYS | A | 129 | 16.544 | 47.962 | 15.276 | 1.00 | 30.82 | C |
| ATOM | 2083 | CG | LYS | A | 129 | 16.381 | 48.600 | 16.659 | 1.00 | 32.18 | C |
| ATOM | 2086 | CD | LYS | A | 129 | 16.068 | 47.583 | 17.744 | 1.00 | 34.34 | C |
| ATOM | 2089 | CE | LYS | A | 129 | 15.662 | 48.291 | 19.048 | 1.00 | 35.70 | C |
| ATOM | 2092 | NZ | LYS | A | 129 | 15.241 | 47.344 | 20.119 | 1.00 | 37.60 | N |
| ATOM | 2096 | C | LYS | A | 129 | 17.545 | 50.036 | 14.248 | 1.00 | 32.32 | C |
| ATOM | 2097 | O | LYS | A | 129 | 18.691 | 49.789 | 13.874 | 1.00 | 31.88 | O |
| ATOM | 2098 | N | GLU | A | 130 | 17.189 | 51.227 | 14.697 | 1.00 | 34.59 | N |
| ATOM | 2100 | CA | GLU | A | 130 | 18.178 | 52.264 | 14.919 | 1.00 | 37.12 | C |
| ATOM | 2102 | CB | GLU | A | 130 | 18.159 | 53.334 | 13.836 | 1.00 | 37.73 | C |
| ATOM | 2105 | CG | GLU | A | 130 | 19.219 | 54.410 | 14.035 | 1.00 | 40.54 | C |
| ATOM | 2108 | CD | GLU | A | 130 | 19.308 | 55.377 | 12.870 | 1.00 | 44.06 | C |
| ATOM | 2109 | OE1 | GLU | A | 130 | 18.410 | 56.253 | 12.754 | 1.00 | 46.60 | O |
| ATOM | 2110 | OE2 | GLU | A | 130 | 20.277 | 55.260 | 12.071 | 1.00 | 47.05 | O |
| ATOM | 2111 | C | GLU | A | 130 | 17.831 | 52.836 | 16.268 | 1.00 | 38.44 | C |
| ATOM | 2112 | O | GLU | A | 130 | 16.839 | 53.560 | 16.419 | 1.00 | 38.52 | O |
| ATOM | 2113 | N | ARG | A | 131 | 18.633 | 52.454 | 17.256 | 1.00 | 40.25 | N |
| ATOM | 2115 | CA | ARG | A | 131 | 18.379 | 52.807 | 18.633 | 1.00 | 41.48 | C |
| ATOM | 2117 | CB | ARG | A | 131 | 18.299 | 54.320 | 18.806 | 1.00 | 42.02 | C |
| ATOM | 2120 | CG | ARG | A | 131 | 19.653 | 54.994 | 18.747 | 1.00 | 45.34 | C |
| ATOM | 2123 | CD | ARG | A | 131 | 19.585 | 56.508 | 18.564 | 1.00 | 49.71 | C |
| ATOM | 2126 | NE | ARG | A | 131 | 19.061 | 57.195 | 19.747 | 1.00 | 53.66 | N |
| ATOM | 2128 | CZ | ARG | A | 131 | 18.894 | 58.514 | 19.832 | 1.00 | 57.36 | C |
| ATOM | 2129 | NH1 | ARG | A | 131 | 19.206 | 59.294 | 18.800 | 1.00 | 58.89 | N |
| ATOM | 2132 | NH2 | ARG | A | 131 | 18.411 | 59.061 | 20.946 | 1.00 | 58.63 | N |
| ATOM | 2135 | C | ARG | A | 131 | 17.070 | 52.163 | 18.997 | 1.00 | 41.33 | C |
| ATOM | 2136 | O | ARG | A | 131 | 16.872 | 50.957 | 18.955 | 1.00 | 41.59 | O |
| ATOM | 2137 | OXT | ARG | A | 131 | 16.139 | 52.864 | 19.330 | 1.00 | 41.93 | O |
| ATOM | 2138 | N | ASP | A | 132 | 15.684 | 53.375 | 19.402 | 1.00 | 34.96 | N |
| ATOM | 2140 | CA | ASP | A | 132 | 14.434 | 52.731 | 19.877 | 1.00 | 34.75 | C |
| ATOM | 2142 | CB | ASP | A | 132 | 13.824 | 53.590 | 20.981 | 1.00 | 35.47 | C |
| ATOM | 2145 | CG | ASP | A | 132 | 14.588 | 53.488 | 22.290 | 1.00 | 38.55 | C |
| ATOM | 2146 | OD1 | ASP | A | 132 | 14.659 | 52.373 | 22.851 | 1.00 | 43.85 | O |
| ATOM | 2147 | OD2 | ASP | A | 132 | 15.147 | 54.467 | 22.839 | 1.00 | 43.35 | O |
| ATOM | 2148 | C | ASP | A | 132 | 13.462 | 52.584 | 18.703 | 1.00 | 32.91 | C |
| ATOM | 2149 | O | ASP | A | 132 | 12.388 | 52.027 | 18.858 | 1.00 | 33.17 | O |
| ATOM | 2152 | N | LEU | A | 133 | 13.815 | 53.182 | 17.571 | 1.00 | 30.94 | N |
| ATOM | 2154 | CA | LEU | A | 133 | 13.060 | 53.071 | 16.326 | 1.00 | 29.27 | C |
| ATOM | 2156 | CB | LEU | A | 133 | 13.230 | 54.379 | 15.555 | 1.00 | 29.34 | C |
| ATOM | 2159 | CG | LEU | A | 133 | 13.010 | 55.632 | 16.413 | 1.00 | 30.29 | C |
| ATOM | 2161 | CD1 | LEU | A | 133 | 13.148 | 56.893 | 15.603 | 1.00 | 31.03 | C |
| ATOM | 2165 | CD2 | LEU | A | 133 | 11.644 | 55.594 | 17.084 | 1.00 | 31.79 | C |
| ATOM | 2169 | C | LEU | A | 133 | 13.371 | 51.884 | 15.386 | 1.00 | 27.63 | C |
| ATOM | 2170 | O | LEU | A | 133 | 14.487 | 51.349 | 15.335 | 1.00 | 26.59 | O |
| ATOM | 2171 | N | PHE | A | 134 | 12.333 | 51.507 | 14.641 | 1.00 | 25.38 | N |
| ATOM | 2173 | CA | PHE | A | 134 | 12.388 | 50.493 | 13.603 | 1.00 | 23.86 | C |
| ATOM | 2175 | CB | PHE | A | 134 | 11.371 | 49.409 | 13.902 | 1.00 | 23.84 | C |
| ATOM | 2178 | CG | PHE | A | 134 | 11.672 | 48.632 | 15.140 | 1.00 | 23.81 | C |
| ATOM | 2179 | CD1 | PHE | A | 134 | 12.532 | 47.555 | 15.102 | 1.00 | 24.83 | C |
| ATOM | 2181 | CE1 | PHE | A | 134 | 12.812 | 46.827 | 16.248 | 1.00 | 25.46 | C |
| ATOM | 2183 | CZ | PHE | A | 134 | 12.239 | 47.179 | 17.438 | 1.00 | 24.86 | C |

TABLE I-continued

The atomic coordinates of an altered human IL-18 structure; SEQ
ID No: 1 with a C38S substitution.
(P6₁)a = 71.4°, b = 71.4°, c = 88.7°, α,β = 90° and γ = 120°

| ATOM | 2185 | CE2 | PHE | A | 134 | 11.389 | 48.250 | 17.496 | 1.00 | 25.34 | C |
|---|---|---|---|---|---|---|---|---|---|---|---|
| ATOM | 2187 | CD2 | PHE | A | 134 | 11.102 | 48.978 | 16.343 | 1.00 | 24.26 | C |
| ATOM | 2189 | C | PHE | A | 134 | 12.036 | 51.216 | 12.304 | 1.00 | 22.99 | C |
| ATOM | 2190 | O | PHE | A | 134 | 10.884 | 51.568 | 12.063 | 1.00 | 22.39 | O |
| ATOM | 2191 | N | LYS | A | 135 | 13.026 | 51.442 | 11.465 | 1.00 | 22.01 | N |
| ATOM | 2193 | CA | LYS | A | 135 | 12.784 | 52.222 | 10.260 | 1.00 | 21.96 | C |
| ATOM | 2195 | CB | LYS | A | 135 | 13.736 | 53.408 | 10.174 | 1.00 | 22.55 | C |
| ATOM | 2198 | CG | LYS | A | 135 | 15.114 | 53.150 | 10.614 | 1.00 | 27.17 | C |
| ATOM | 2201 | CD | LYS | A | 135 | 15.752 | 54.440 | 11.190 | 1.00 | 31.21 | C |
| ATOM | 2204 | CE | LYS | A | 135 | 15.641 | 55.625 | 10.238 | 1.00 | 34.01 | C |
| ATOM | 2207 | NZ | LYS | A | 135 | 16.573 | 56.760 | 10.608 | 1.00 | 38.74 | N |
| ATOM | 2211 | C | LYS | A | 135 | 12.834 | 51.428 | 8.982 | 1.00 | 19.95 | C |
| ATOM | 2212 | O | LYS | A | 135 | 13.459 | 50.371 | 8.905 | 1.00 | 19.00 | O |
| ATOM | 2213 | N | LEU | A | 136 | 12.125 | 51.954 | 7.996 | 1.00 | 18.98 | N |
| ATOM | 2215 | CA | LEU | A | 136 | 12.140 | 51.402 | 6.659 | 1.00 | 18.68 | C |
| ATOM | 2217 | CB | LEU | A | 136 | 10.849 | 51.738 | 5.911 | 1.00 | 18.73 | C |
| ATOM | 2220 | CG | LEU | A | 136 | 10.766 | 51.191 | 4.480 | 1.00 | 17.71 | C |
| ATOM | 2222 | CD1 | LEU | A | 136 | 10.502 | 49.701 | 4.505 | 1.00 | 18.75 | C |
| ATOM | 2226 | CD2 | LEU | A | 136 | 9.678 | 51.889 | 3.686 | 1.00 | 17.40 | C |
| ATOM | 2230 | C | LEU | A | 136 | 13.305 | 52.066 | 5.969 | 1.00 | 18.53 | C |
| ATOM | 2231 | O | LEU | A | 136 | 13.397 | 53.281 | 5.945 | 1.00 | 18.21 | O |
| ATOM | 2232 | N | ILE | A | 137 | 14.211 | 51.274 | 5.434 | 1.00 | 17.97 | N |
| ATOM | 2234 | CA | ILE | A | 137 | 15.321 | 51.821 | 4.702 | 1.00 | 18.57 | C |
| ATOM | 2236 | CB | ILE | A | 137 | 16.638 | 51.658 | 5.504 | 1.00 | 18.88 | C |
| ATOM | 2238 | CG1 | ILE | A | 137 | 16.971 | 50.179 | 5.667 | 1.00 | 19.36 | C |
| ATOM | 2241 | CD1 | ILE | A | 137 | 18.369 | 49.924 | 6.185 | 1.00 | 21.77 | C |
| ATOM | 2245 | CG2 | ILE | A | 137 | 16.524 | 52.287 | 6.883 | 1.00 | 19.34 | C |
| ATOM | 2249 | C | ILE | A | 137 | 15.438 | 51.065 | 3.396 | 1.00 | 18.91 | C |
| ATOM | 2250 | O | ILE | A | 137 | 14.756 | 50.052 | 3.171 | 1.00 | 17.82 | O |
| ATOM | 2251 | N | LEU | A | 138 | 16.311 | 51.567 | 2.538 | 1.00 | 19.23 | N |
| ATOM | 2253 | CA | LEU | A | 138 | 16.684 | 50.842 | 1.352 | 1.00 | 20.34 | C |
| ATOM | 2255 | CB | LEU | A | 138 | 16.762 | 51.754 | 0.150 | 1.00 | 20.52 | C |
| ATOM | 2258 | CG | LEU | A | 138 | 17.104 | 51.009 | −1.132 | 1.00 | 21.99 | C |
| ATOM | 2260 | CD1 | LEU | A | 138 | 15.894 | 50.326 | −1.683 | 1.00 | 22.14 | C |
| ATOM | 2264 | CD2 | LEU | A | 138 | 17.676 | 51.971 | −2.172 | 1.00 | 24.33 | C |
| ATOM | 2268 | C | LEU | A | 138 | 18.049 | 50.308 | 1.630 | 1.00 | 21.00 | C |
| ATOM | 2269 | O | LEU | A | 138 | 18.937 | 51.066 | 1.974 | 1.00 | 20.84 | O |
| ATOM | 2270 | N | LYS | A | 139 | 18.257 | 49.017 | 1.484 | 1.00 | 21.81 | N |
| ATOM | 2272 | CA | LYS | A | 139 | 19.588 | 48.549 | 1.722 | 1.00 | 22.88 | C |
| ATOM | 2274 | CB | LYS | A | 139 | 19.710 | 47.968 | 3.124 | 1.00 | 24.00 | C |
| ATOM | 2277 | CG | LYS | A | 139 | 19.222 | 46.582 | 3.278 | 1.00 | 26.46 | C |
| ATOM | 2280 | CD | LYS | A | 139 | 19.697 | 46.037 | 4.612 | 1.00 | 28.74 | C |
| ATOM | 2283 | CE | LYS | A | 139 | 19.184 | 44.649 | 4.858 | 1.00 | 29.57 | C |
| ATOM | 2286 | NZ | LYS | A | 139 | 19.522 | 44.134 | 6.236 | 1.00 | 29.04 | N |
| ATOM | 2290 | C | LYS | A | 139 | 20.078 | 47.566 | 0.707 | 1.00 | 22.74 | C |
| ATOM | 2291 | O | LYS | A | 139 | 19.302 | 46.814 | 0.115 | 1.00 | 21.42 | O |
| ATOM | 2292 | N | LYS | A | 140 | 21.387 | 47.599 | 0.487 | 1.00 | 22.53 | N |
| ATOM | 2294 | CA | LYS | A | 140 | 22.000 | 46.675 | −0.432 | 1.00 | 23.48 | C |
| ATOM | 2296 | CB | LYS | A | 140 | 23.437 | 47.080 | −0.768 | 1.00 | 23.90 | C |
| ATOM | 2299 | CG | LYS | A | 140 | 24.109 | 46.147 | −1.755 | 1.00 | 26.16 | C |
| ATOM | 2302 | CD | LYS | A | 140 | 25.510 | 46.642 | −2.168 | 1.00 | 29.72 | C |
| ATOM | 2305 | CE | LYS | A | 140 | 26.077 | 45.822 | −3.335 | 1.00 | 32.07 | C |
| ATOM | 2308 | NZ | LYS | A | 140 | 25.928 | 44.344 | −3.151 | 1.00 | 35.10 | N |
| ATOM | 2312 | C | LYS | A | 140 | 21.979 | 45.356 | 0.292 | 1.00 | 23.49 | C |
| ATOM | 2313 | O | LYS | A | 140 | 22.503 | 45.261 | 1.379 | 1.00 | 23.51 | O |
| ATOM | 2314 | N | GLU | A | 141 | 21.400 | 44.342 | −0.305 | 1.00 | 23.54 | N |
| ATOM | 2316 | CA | GLU | A | 141 | 21.287 | 43.068 | 0.357 | 1.00 | 24.75 | C |
| ATOM | 2318 | CB | GLU | A | 141 | 19.825 | 42.816 | 0.709 | 1.00 | 24.91 | C |
| ATOM | 2321 | CG | GLU | A | 141 | 19.589 | 41.464 | 1.352 | 1.00 | 27.12 | C |
| ATOM | 2324 | CD | GLU | A | 141 | 20.296 | 41.339 | 2.679 | 1.00 | 28.59 | C |
| ATOM | 2325 | OE1 | GLU | A | 141 | 21.302 | 40.621 | 2.760 | 1.00 | 23.69 | O |
| ATOM | 2326 | OE2 | GLU | A | 141 | 19.829 | 41.977 | 3.642 | 1.00 | 33.25 | O |
| ATOM | 2327 | C | GLU | A | 141 | 21.775 | 41.963 | −0.531 | 1.00 | 24.90 | C |
| ATOM | 2328 | O | GLU | A | 141 | 21.195 | 41.698 | −1.583 | 1.00 | 25.79 | O |
| ATOM | 2329 | N | ASP | A | 142 | 22.822 | 41.284 | −0.114 | 1.00 | 24.81 | N |
| ATOM | 2331 | CA | ASP | A | 142 | 23.311 | 40.174 | −0.915 | 1.00 | 25.28 | C |
| ATOM | 2333 | CB | ASP | A | 142 | 24.832 | 40.085 | −0.833 | 1.00 | 26.35 | C |
| ATOM | 2336 | CG | ASP | A | 142 | 25.497 | 41.343 | −1.326 | 1.00 | 29.58 | C |
| ATOM | 2337 | OD1 | ASP | A | 142 | 25.182 | 41.792 | −2.457 | 1.00 | 34.14 | O |
| ATOM | 2338 | OD2 | ASP | A | 142 | 26.317 | 41.976 | −0.643 | 1.00 | 35.96 | O |
| ATOM | 2339 | C | ASP | A | 142 | 22.674 | 38.851 | −0.510 | 1.00 | 24.08 | C |
| ATOM | 2340 | O | ASP | A | 142 | 22.721 | 37.883 | −1.271 | 1.00 | 23.79 | O |
| ATOM | 2341 | N | GLU | A | 143 | 22.036 | 38.818 | 0.655 | 1.00 | 22.40 | N |
| ATOM | 2343 | CA | GLU | A | 143 | 21.439 | 37.576 | 1.138 | 1.00 | 21.65 | C |
| ATOM | 2345 | CB | GLU | A | 143 | 21.944 | 37.254 | 2.536 | 1.00 | 21.75 | C |

TABLE I-continued

The atomic coordinates of an altered human IL-18 structure; SEQ ID No: 1 with a C38S substitution.
(P6$_1$)a = 71.4°, b = 71.4°, c = 88.7°, α,β = 90° and γ = 120°

| ATOM | 2348 | CG  | GLU | A | 143 | 23.433 | 36.965 | 2.596  | 1.00 | 22.62 | C |
|------|------|-----|-----|---|-----|--------|--------|--------|------|-------|---|
| ATOM | 2351 | CD  | GLU | A | 143 | 23.848 | 35.809 | 1.708  | 1.00 | 22.90 | C |
| ATOM | 2352 | OE1 | GLU | A | 143 | 23.037 | 34.908 | 1.464  | 1.00 | 21.42 | O |
| ATOM | 2353 | OE2 | GLU | A | 143 | 25.017 | 35.785 | 1.272  | 1.00 | 26.11 | O |
| ATOM | 2354 | C   | GLU | A | 143 | 19.929 | 37.623 | 1.134  | 1.00 | 21.12 | C |
| ATOM | 2355 | O   | GLU | A | 143 | 19.303 | 38.268 | 1.984  | 1.00 | 20.40 | O |
| ATOM | 2356 | N   | LEU | A | 144 | 19.339 | 36.915 | 0.187  | 1.00 | 20.66 | N |
| ATOM | 2358 | CA  | LEU | A | 144 | 17.900 | 36.955 | 0.034  | 1.00 | 21.04 | C |
| ATOM | 2360 | CB  | LEU | A | 144 | 17.484 | 36.338 | −1.298 | 1.00 | 21.46 | C |
| ATOM | 2363 | CG  | LEU | A | 144 | 17.253 | 37.308 | −2.456 | 1.00 | 24.60 | C |
| ATOM | 2365 | CD1 | LEU | A | 144 | 18.245 | 38.440 | −2.516 | 1.00 | 25.92 | C |
| ATOM | 2369 | CD2 | LEU | A | 144 | 17.199 | 36.518 | −3.775 | 1.00 | 26.20 | C |
| ATOM | 2373 | C   | LEU | A | 144 | 17.196 | 36.250 | 1.183  | 1.00 | 20.25 | C |
| ATOM | 2374 | O   | LEU | A | 144 | 15.998 | 36.444 | 1.381  | 1.00 | 19.65 | O |
| ATOM | 2375 | N   | GLY | A | 145 | 17.950 | 35.468 | 1.955  | 1.00 | 19.06 | N |
| ATOM | 2377 | CA  | GLY | A | 145 | 17.387 | 34.748 | 3.081  | 1.00 | 18.63 | C |
| ATOM | 2380 | C   | GLY | A | 145 | 17.220 | 35.624 | 4.307  | 1.00 | 18.10 | C |
| ATOM | 2381 | O   | GLY | A | 145 | 16.716 | 35.168 | 5.323  | 1.00 | 18.03 | O |
| ATOM | 2382 | N   | ASP | A | 146 | 17.630 | 36.883 | 4.205  | 1.00 | 17.78 | N |
| ATOM | 2384 | CA  | ASP | A | 146 | 17.529 | 37.829 | 5.308  | 1.00 | 18.41 | C |
| ATOM | 2386 | CB  | ASP | A | 146 | 18.382 | 39.046 | 5.008  | 1.00 | 19.11 | C |
| ATOM | 2389 | CG  | ASP | A | 146 | 18.651 | 39.902 | 6.233  | 1.00 | 22.22 | C |
| ATOM | 2390 | OD1 | ASP | A | 146 | 17.793 | 40.025 | 7.130  | 1.00 | 22.44 | O |
| ATOM | 2391 | OD2 | ASP | A | 146 | 19.725 | 40.512 | 6.373  | 1.00 | 29.90 | O |
| ATOM | 2392 | C   | ASP | A | 146 | 16.084 | 38.269 | 5.559  | 1.00 | 18.16 | C |
| ATOM | 2393 | O   | ASP | A | 146 | 15.470 | 38.924 | 4.723  | 1.00 | 17.37 | O |
| ATOM | 2394 | N   | ARG | A | 147 | 15.567 | 37.909 | 6.727  | 1.00 | 18.11 | N |
| ATOM | 2396 | CA  | ARG | A | 147 | 14.201 | 38.211 | 7.117  | 1.00 | 18.48 | C |
| ATOM | 2398 | CB  | ARG | A | 147 | 13.861 | 37.561 | 8.457  | 1.00 | 18.61 | C |
| ATOM | 2401 | CG  | ARG | A | 147 | 13.558 | 36.104 | 8.369  | 1.00 | 20.73 | C |
| ATOM | 2404 | CD  | ARG | A | 147 | 13.348 | 35.404 | 9.744  | 1.00 | 23.31 | C |
| ATOM | 2407 | NE  | ARG | A | 147 | 14.011 | 34.154 | 9.564  | 1.00 | 27.87 | N |
| ATOM | 2409 | CZ  | ARG | A | 147 | 15.110 | 33.753 | 10.172 | 1.00 | 27.13 | C |
| ATOM | 2410 | NH1 | ARG | A | 147 | 15.654 | 34.419 | 11.194 | 1.00 | 28.07 | N |
| ATOM | 2413 | NH2 | ARG | A | 147 | 15.620 | 32.618 | 9.769  | 1.00 | 27.24 | N |
| ATOM | 2416 | C   | ARG | A | 147 | 13.944 | 39.696 | 7.232  | 1.00 | 17.88 | C |
| ATOM | 2417 | O   | ARG | A | 147 | 12.798 | 40.128 | 7.157  | 1.00 | 18.18 | O |
| ATOM | 2418 | N   | SER | A | 148 | 14.992 | 40.482 | 7.418  | 1.00 | 17.16 | N |
| ATOM | 2420 | CA  | SER | A | 148 | 14.822 | 41.919 | 7.551  | 1.00 | 17.22 | C |
| ATOM | 2422 | CB  | SER | A | 148 | 16.129 | 42.604 | 7.962  | 1.00 | 17.56 | C |
| ATOM | 2425 | OG  | SER | A | 148 | 17.131 | 42.385 | 6.983  | 1.00 | 20.70 | O |
| ATOM | 2427 | C   | SER | A | 148 | 14.275 | 42.563 | 6.275  | 1.00 | 16.43 | C |
| ATOM | 2428 | O   | SER | A | 148 | 13.790 | 43.699 | 6.336  | 1.00 | 16.13 | O |
| ATOM | 2429 | N   | ILE | A | 149 | 14.365 | 41.869 | 5.132  | 1.00 | 15.25 | N |
| ATOM | 2431 | CA  | ILE | A | 149 | 13.809 | 42.403 | 3.886  | 1.00 | 14.90 | C |
| ATOM | 2433 | CB  | ILE | A | 149 | 14.823 | 42.397 | 2.745  | 1.00 | 15.35 | C |
| ATOM | 2435 | CG1 | ILE | A | 149 | 15.226 | 40.981 | 2.346  | 1.00 | 14.55 | C |
| ATOM | 2438 | CD1 | ILE | A | 149 | 15.824 | 40.952 | 0.958  | 1.00 | 17.24 | C |
| ATOM | 2442 | CG2 | ILE | A | 149 | 16.068 | 43.200 | 3.121  | 1.00 | 15.79 | C |
| ATOM | 2446 | C   | ILE | A | 149 | 12.540 | 41.662 | 3.477  | 1.00 | 14.46 | C |
| ATOM | 2447 | O   | ILE | A | 149 | 12.119 | 41.736 | 2.338  | 1.00 | 13.29 | O |
| ATOM | 2448 | N   | MET | A | 150 | 11.934 | 40.966 | 4.432  | 1.00 | 14.06 | N |
| ATOM | 2450 | CA  | MET | A | 150 | 10.728 | 40.211 | 4.180  | 1.00 | 14.01 | C |
| ATOM | 2452 | CB  | MET | A | 150 | 10.881 | 38.785 | 4.689  | 1.00 | 14.32 | C |
| ATOM | 2455 | CG  | MET | A | 150 | 11.968 | 38.009 | 3.970  | 1.00 | 14.36 | C |
| ATOM | 2458 | SD  | MET | A | 150 | 11.979 | 36.322 | 4.490  | 1.00 | 15.53 | S |
| ATOM | 2459 | CE  | MET | A | 150 | 13.509 | 35.730 | 3.646  | 1.00 | 15.34 | C |
| ATOM | 2463 | C   | MET | A | 150 | 9.526  | 40.889 | 4.853  | 1.00 | 14.00 | C |
| ATOM | 2464 | O   | MET | A | 150 | 9.632  | 41.407 | 5.975  | 1.00 | 14.37 | O |
| ATOM | 2465 | N   | PHE | A | 151 | 8.407  | 40.922 | 4.137  | 1.00 | 13.04 | N |
| ATOM | 2467 | CA  | PHE | A | 151 | 7.192  | 41.556 | 4.628  | 1.00 | 12.74 | C |
| ATOM | 2469 | CB  | PHE | A | 151 | 7.057  | 42.963 | 4.032  | 1.00 | 12.76 | C |
| ATOM | 2472 | CG  | PHE | A | 151 | 8.241  | 43.827 | 4.276  | 1.00 | 13.14 | C |
| ATOM | 2473 | CD1 | PHE | A | 151 | 8.337  | 44.557 | 5.435  | 1.00 | 14.08 | C |
| ATOM | 2475 | CE1 | PHE | A | 151 | 9.445  | 45.336 | 5.677  | 1.00 | 15.32 | C |
| ATOM | 2477 | CZ  | PHE | A | 151 | 10.471 | 45.383 | 4.753  | 1.00 | 14.93 | C |
| ATOM | 2479 | CE2 | PHE | A | 151 | 10.383 | 44.670 | 3.598  | 1.00 | 13.48 | C |
| ATOM | 2481 | CD2 | PHE | A | 151 | 9.281  | 43.872 | 3.369  | 1.00 | 14.58 | C |
| ATOM | 2483 | C   | PHE | A | 151 | 5.980  | 40.780 | 4.203  | 1.00 | 12.85 | C |
| ATOM | 2484 | O   | PHE | A | 151 | 6.049  | 39.983 | 3.278  | 1.00 | 14.01 | O |
| ATOM | 2485 | N   | THR | A | 152 | 4.860  | 41.019 | 4.875  | 1.00 | 12.94 | N |
| ATOM | 2487 | CA  | THR | A | 152 | 3.578  | 40.523 | 4.415  | 1.00 | 13.01 | C |
| ATOM | 2489 | CB  | THR | A | 152 | 2.829  | 39.760 | 5.502  | 1.00 | 13.46 | C |
| ATOM | 2491 | OG1 | THR | A | 152 | 2.664  | 40.602 | 6.649  | 1.00 | 12.42 | O |
| ATOM | 2493 | CG2 | THR | A | 152 | 3.660  | 38.562 | 5.997  | 1.00 | 14.76 | C |

TABLE I-continued

The atomic coordinates of an altered human IL-18 structure; SEQ ID No: 1 with a C38S substitution.

TABLE I-continued

The atomic coordinates of an altered human IL-18 structure; SEQ ID No: 1 with a C38S substitution.
(P6$_1$)a = 71.4°, b = 71.4°, c = 88.7°, α,β = 90° and γ = 120°

| ATOM | 2681 | O | HOH | W | 196 | −4.690 | 40.058 | 2.272 | 1.00 | 25.95 | O |
|---|---|---|---|---|---|---|---|---|---|---|---|
| ATOM | 2684 | O | HOH | W | 197 | 8.430 | 28.376 | −3.973 | 1.00 | 37.40 | O |
| ATOM | 2687 | O | HOH | W | 198 | −3.634 | 58.669 | −7.708 | 1.00 | 34.27 | O |
| ATOM | 2690 | O | HOH | W | 199 | 16.894 | 46.819 | −12.407 | 1.00 | 24.91 | O |
| ATOM | 2693 | O | HOH | W | 200 | 4.198 | 39.902 | 8.744 | 1.00 | 34.44 | O |
| ATOM | 2696 | O | HOH | W | 201 | 14.854 | 34.185 | 0.057 | 1.00 | 28.32 | O |
| ATOM | 2699 | O | HOH | W | 202 | 14.294 | 41.383 | −19.006 | 1.00 | 36.69 | O |
| ATOM | 2702 | O | HOH | W | 203 | −7.460 | 46.312 | −0.048 | 1.00 | 23.37 | O |
| ATOM | 2705 | O | HOH | W | 205 | 16.445 | 31.061 | 3.569 | 1.00 | 30.69 | O |
| ATOM | 2708 | O | HOH | W | 206 | 20.610 | 48.824 | −11.130 | 1.00 | 37.46 | O |
| ATOM | 2711 | O | HOH | W | 207 | 4.554 | 54.054 | −20.941 | 1.00 | 34.43 | O |
| ATOM | 2714 | O | HOH | W | 208 | 22.716 | 49.620 | 2.171 | 1.00 | 44.73 | O |
| ATOM | 2717 | O | HOH | W | 209 | −3.777 | 59.118 | 21.276 | 1.00 | 27.67 | O |
| ATOM | 2720 | O | HOH | W | 210 | 1.193 | 38.163 | 15.220 | 1.00 | 39.78 | O |
| ATOM | 2723 | O | HOH | W | 211 | 4.511 | 58.756 | −19.600 | 1.00 | 39.54 | O |
| ATOM | 2726 | O | HOH | W | 212 | 0.825 | 47.701 | −22.991 | 1.00 | 32.59 | O |
| ATOM | 2729 | O | HOH | W | 213 | 1.022 | 44.133 | −3.659 | 1.00 | 23.31 | O |
| ATOM | 2732 | O | HOH | W | 214 | −1.440 | 41.646 | 13.910 | 1.00 | 27.10 | O |
| ATOM | 2735 | O | HOH | W | 215 | 3.952 | 48.442 | 23.775 | 1.00 | 27.10 | O |
| ATOM | 2738 | O | HOH | W | 216 | 15.459 | 33.255 | −5.580 | 1.00 | 33.32 | O |
| ATOM | 2741 | O | HOH | W | 217 | 5.420 | 30.640 | 5.291 | 1.00 | 48.75 | O |
| ATOM | 2744 | O | HOH | W | 218 | −8.242 | 49.779 | 4.040 | 1.00 | 43.18 | O |
| ATOM | 2747 | O | HOH | W | 219 | 7.431 | 50.241 | 18.373 | 1.00 | 48.35 | O |
| ATOM | 2750 | O | HOH | W | 220 | 18.011 | 46.044 | 12.605 | 1.00 | 28.37 | O |
| ATOM | 2753 | O | HOH | W | 221 | 12.789 | 55.627 | 8.288 | 1.00 | 35.75 | O |
| ATOM | 2756 | O | HOH | W | 222 | 5.835 | 41.030 | 17.983 | 1.00 | 81.64 | O |
| ATOM | 2759 | O | HOH | W | 224 | −4.461 | 43.343 | −23.800 | 1.00 | 37.43 | O |
| ATOM | 2762 | O | HOH | W | 225 | −1.665 | 52.565 | −19.349 | 1.00 | 33.20 | O |
| ATOM | 2765 | O | HOH | W | 226 | −1.205 | 48.642 | −19.463 | 1.00 | 41.74 | O |
| ATOM | 2768 | O | HOH | W | 227 | 12.301 | 62.613 | −2.979 | 1.00 | 38.97 | O |
| ATOM | 2771 | O | HOH | W | 228 | 16.655 | 41.020 | −16.375 | 1.00 | 39.48 | O |
| ATOM | 2774 | O | HOH | W | 229 | 11.528 | 44.224 | 14.664 | 1.00 | 31.66 | O |
| ATOM | 2777 | O | HOH | W | 230 | −6.936 | 53.638 | −3.765 | 1.00 | 67.47 | O |
| ATOM | 2780 | O | HOH | W | 231 | 6.936 | 58.398 | −18.190 | 1.00 | 23.19 | O |
| ATOM | 2783 | O | HOH | W | 232 | 27.067 | 53.984 | −3.068 | 1.00 | 63.58 | O |
| ATOM | 2786 | O | HOH | W | 233 | 9.786 | 51.563 | 18.320 | 1.00 | 44.43 | O |
| ATOM | 2789 | O | HOH | W | 234 | −0.115 | 58.692 | −19.029 | 1.00 | 38.37 | O |
| ATOM | 2792 | O | HOH | W | 235 | 18.778 | 54.022 | 9.782 | 1.00 | 82.22 | O |
| ATOM | 2795 | O | HOH | W | 236 | 23.671 | 47.969 | 11.644 | 1.00 | 73.89 | O |
| ATOM | 2798 | O | HOH | W | 237 | 11.756 | 32.735 | 5.883 | 1.00 | 43.37 | O |
| ATOM | 2801 | O | HOH | W | 238 | 8.089 | 25.977 | 2.891 | 1.00 | 51.09 | O |
| ATOM | 2804 | O | HOH | W | 239 | 10.237 | 57.042 | −17.293 | 1.00 | 21.75 | O |
| ATOM | 2807 | O | HOH | W | 240 | 10.289 | 47.280 | −23.281 | 1.00 | 23.32 | O |
| ATOM | 2810 | O | HOH | W | 241 | −6.000 | 51.764 | −10.955 | 1.00 | 59.04 | O |
| ATOM | 2813 | O | HOH | W | 242 | 12.600 | 55.868 | −21.300 | 1.00 | 54.68 | O |
| ATOM | 2816 | O | HOH | W | 243 | 13.305 | 30.107 | 1.090 | 1.00 | 32.20 | O |
| ATOM | 2819 | O | HOH | W | 244 | 13.639 | 60.367 | −8.857 | 1.00 | 39.30 | O |
| ATOM | 2822 | O | HOH | W | 245 | 10.018 | 65.972 | 4.559 | 1.00 | 65.65 | O |
| ATOM | 2825 | O | HOH | W | 246 | −7.160 | 54.898 | 3.843 | 1.00 | 37.98 | O |
| ATOM | 2828 | O | HOH | W | 248 | 14.798 | 43.742 | 11.446 | 1.00 | 44.58 | O |
| ATOM | 2831 | O | HOH | W | 249 | 11.344 | 43.768 | 17.684 | 1.00 | 43.94 | O |
| ATOM | 2834 | O | HOH | W | 250 | 4.159 | 28.986 | 0.597 | 1.00 | 29.63 | O |
| ATOM | 2837 | O | HOH | W | 251 | 18.107 | 58.024 | −8.569 | 1.00 | 42.42 | O |
| ATOM | 2840 | O | HOH | W | 252 | 17.168 | 56.125 | 7.711 | 1.00 | 38.97 | O |
| ATOM | 2843 | O | HOH | W | 253 | 5.575 | 27.738 | −1.350 | 1.00 | 63.72 | O |
| ATOM | 2846 | O | HOH | W | 254 | 14.064 | 32.232 | 7.272 | 1.00 | 23.52 | O |
| ATOM | 2849 | O | HOH | W | 255 | 7.205 | 31.672 | −3.143 | 1.00 | 20.29 | O |
| ATOM | 2852 | O | HOH | W | 256 | 20.379 | 34.105 | 1.634 | 1.00 | 17.16 | O |
| ATOM | 2855 | O | HOH | W | 257 | −2.052 | 56.203 | 23.818 | 1.00 | 23.02 | O |
| ATOM | 2858 | O | HOH | W | 259 | 1.620 | 49.332 | −20.602 | 1.00 | 21.91 | O |
| ATOM | 2861 | O | HOH | W | 260 | 22.845 | 34.062 | −1.085 | 1.00 | 22.09 | O |
| ATOM | 2864 | O | HOH | W | 261 | 28.445 | 38.320 | −0.263 | 1.00 | 22.98 | O |
| ATOM | 2867 | O | HOH | W | 262 | −1.709 | 57.495 | 20.049 | 1.00 | 26.80 | O |
| ATOM | 2870 | O | HOH | W | 263 | 8.157 | 54.423 | 16.370 | 1.00 | 26.04 | O |
| ATOM | 2873 | O | HOH | W | 264 | −2.564 | 42.928 | −25.602 | 1.00 | 28.10 | O |
| ATOM | 2876 | O | HOH | W | 265 | 11.093 | 43.070 | 7.633 | 1.00 | 21.20 | O |
| ATOM | 2879 | O | HOH | W | 266 | 0.138 | 39.356 | −0.268 | 1.00 | 32.98 | O |
| ATOM | 2882 | O | HOH | W | 267 | 16.045 | 42.245 | −12.562 | 1.00 | 38.36 | O |
| ATOM | 2885 | O | HOH | W | 268 | −3.787 | 56.629 | −6.218 | 1.00 | 27.65 | O |
| ATOM | 2888 | O | HOH | W | 270 | 16.150 | 45.707 | −14.627 | 1.00 | 23.75 | O |
| ATOM | 2891 | O | HOH | W | 271 | 2.128 | 48.235 | −25.659 | 1.00 | 37.19 | O |
| ATOM | 2894 | O | HOH | W | 272 | −3.094 | 56.367 | 2.257 | 1.00 | 26.14 | O |
| ATOM | 2897 | O | HOH | W | 273 | 10.697 | 62.331 | 1.963 | 1.00 | 33.95 | O |
| ATOM | 2900 | O | HOH | W | 274 | 22.653 | 48.364 | −8.018 | 1.00 | 31.60 | O |
| ATOM | 2903 | O | HOH | W | 275 | 8.398 | 53.786 | −23.582 | 1.00 | 37.67 | O |

TABLE I-continued

The atomic coordinates of an altered human IL-18 structure; SEQ ID No: 1 with a C38S substitution.
(

TABLE I-continued

The atomic coordinates of an altered human IL-18 structure; SEQ ID No: 1 with a C38S substitution. $(P6_1)a = 71.4°, b = 71.4°, c = 88.7°, \alpha,\beta = 90°$ and $\gamma = 120°$

| | | | | | | | | | | | |
|---|---|---|---|---|---|---|---|---|---|---|---|
| ATOM | 3131 | O | HOH | W | 413 | 20.096 | 46.863 | 8.617 | 1.00 | 40.83 | O |
| ATOM | 3134 | O | HOH | W | 415 | 8.692 | 59.349 | 15.091 | 1.00 | 28.12 | O |
| ATOM | 3137 | O | HOH | W | 420 | 16.735 | 56.070 | 3.791 | 1.00 | 41.20 | O |
| ATOM | 3140 | O | HOH | W | 421 | 6.718 | 44.005 | −24.075 | 1.00 | 31.26 | O |
| ATOM | 3143 | O | HOH | W | 422 | 3.982 | 44.239 | 26.463 | 1.00 | 51.23 | O |
| ATOM | 3146 | O | HOH | W | 425 | 4.101 | 36.325 | 12.237 | 1.00 | 51.25 | O |
| ATOM | 3149 | O | HOH | W | 427 | 5.836 | 53.907 | −23.829 | 1.00 | 36.87 | O |
| ATOM | 3152 | O | HOH | W | 428 | 0.815 | 62.667 | 0.840 | 1.00 | 41.62 | O |
| ATOM | 3155 | O | HOH | W | 429 | −4.430 | 57.682 | 4.200 | 1.00 | 40.20 | O |
| ATOM | 3158 | O | HOH | W | 430 | −0.075 | 39.402 | 10.982 | 1.00 | 37.90 | O |
| ATOM | 3161 | O | HOH | W | 431 | 12.525 | 60.939 | −5.748 | 1.00 | 49.35 | O |
| ATOM | 3164 | O | HOH | W | 433 | 24.502 | 50.238 | −7.371 | 1.00 | 50.44 | O |
| ATOM | 3167 | O | HOH | W | 434 | 12.218 | 42.640 | 10.614 | 1.00 | 48.43 | O |
| ATOM | 3170 | O | HOH | W | 437 | 0.408 | 59.563 | 20.080 | 1.00 | 45.61 | O |
| ATOM | 3173 | O | HOH | W | 438 | 5.015 | 43.535 | 17.595 | 1.00 | 43.03 | O |
| ATOM | 3176 | O | HOH | W | 439 | 3.707 | 65.537 | 8.611 | 1.00 | 58.11 | O |
| ATOM | 3179 | O | HOH | W | 440 | 15.448 | 41.840 | −21.554 | 1.00 | 51.86 | O |
| ATOM | 3182 | O | HOH | W | 443 | 0.656 | 39.927 | −11.904 | 1.00 | 59.54 | O |

What is claimed is:

1. A composition comprising human IL-18 protein in a crystalline form, wherein said protein has a cysteine to serine substitution at residue 38 of SEQ ID No: 1, and wherein the protein crystal is a primitive hexagonal ($P6_1$) crystal with unit cell dimensions a=71.4°, b=71.4°, c=88.7° $\alpha,\beta$=90° and $\gamma$=120°.

2. The composition according to claim 1 wherein said human IL-1B protein is characterized by a $\beta$-trefoil fold.

3. A process of identifying an agonist or an antagonist of human IL-18 selected from the group consisting of: a peptide, a non-peptide and a small molecule;
   wherein said agonist or antagonist is capable of enhancing, eliciting or blocking the interaction between human IL-18 and its receptor;
   wherein said process comprises:
   a) crystallizing the composition of claim 1 and determining the three-dimensional structural coordinates defined in Table 1;
   b) introducing into a suitable computer program, said three-dimensional structural coordinates and having the program display said coordinates;
   c) creating a three-dimensional model of a test compound in said computer program;
   d) displaying and superimposing the model of said test compound onto the three-dimensional structural coordinates of the IL-18 protein;
   e) assessing whether said test compound model is capable of affecting the interaction between IL-18 and its receptor; and
   f) incorporating said test compound in an IL-18 activity assay and determining whether said test compound inhibits or enhances the biological activity of human IL-18 wherein said compounds are identified as agonists or antagonists.

4. A process of identifying an agonist or an antagonist capable of modifying the biological activity of the composition of claim 1, wherein said process comprises:
   carrying out an in vitro assay by introducing said compound into an IL-18 activity assay mixture; and determining whether said test compound inhibits or enhances the biological activity of human IL-18 receptor, wherein said compounds are identified as agonists or antagonists.

* * * * *

SEQUENCE LISTING

```
<160> NUMBER OF SEQ ID NOS: 1

<210> SEQ ID NO 1
<211> LENGTH: 156
<212> TYPE: PRT
<213> ORGANISM: Homo sapiens

<400> SEQUENCE: 1

Tyr Phe Gly Lys Leu Glu Ser Lys Leu Ser Val Ile Arg Asn Leu Asn
 1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Met Tyr Lys Asp Ser Gln Pro Arg Gly Met Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Gly Tyr Phe Leu Ala Cys Glu Lys
        115                 120                 125

Glu Arg Asp Leu Phe Lys Leu Ile Leu Lys Lys Glu Asp Glu Leu Gly
    130                 135                 140

Asp Arg Ser Ile Met Phe Thr Val Gln Asn Glu Asp
145                 150                 155
```